(12) United States Patent
Cheng et al.

(10) Patent No.: US 8,889,683 B2
(45) Date of Patent: Nov. 18, 2014

(54) SUBSTITUTED QUINOXALINES AS INHIBITORS OF FATTY ACID BINDING PROTEIN

(75) Inventors: Clifford Cheng, Cambridge, MA (US); Gerald W. Shipps, Jr., Stoneham, MA (US); Xiaohua Huang, Brookline, MA (US); Ying Huang, Berkeley Heights, NJ (US); Ning Shao, Watchung, NJ (US); Ashwin Rao, Morganville, NJ (US); Anandan Palani, Bridgewater, NJ (US); Peter Orth, New York, NY (US); Johannes H. Voigt, Cranford, NJ (US); Robert J. Herr, Voorheesville, NY (US); Lana Michele Rossiter, Clifton Park, NY (US); Qi Zeng, Delmar, NY (US); Xianfeng Sun, Guilderland, NY (US)

(73) Assignee: Merck Sharp & Dohme Corp., Rahway, NJ (US)

(*) Notice: Subject to any disclaimer, the term of this patent is extended or adjusted under 35 U.S.C. 154(b) by 70 days.

(21) Appl. No.: 13/242,426

(22) Filed: Sep. 23, 2011

(65) Prior Publication Data

US 2012/0122837 A1    May 17, 2012

Related U.S. Application Data

(60) Provisional application No. 61/386,786, filed on Sep. 27, 2010.

(51) Int. Cl.
| | |
|---|---|
| *A61K 31/498* | (2006.01) |
| *C07D 241/44* | (2006.01) |
| *C07D 401/14* | (2006.01) |
| *C07D 403/14* | (2006.01) |
| *C07D 413/06* | (2006.01) |
| *C07D 401/06* | (2006.01) |
| *C07D 403/12* | (2006.01) |
| *C07D 403/06* | (2006.01) |

(52) U.S. Cl.
CPC ............ *C07D 403/06* (2013.01); *C07D 401/14* (2013.01); *C07D 403/14* (2013.01); *C07D 413/06* (2013.01); *C07D 241/44* (2013.01); *C07D 401/06* (2013.01); *C07D 403/12* (2013.01)
USPC ........... 514/249; 540/607; 544/355; 546/245; 546/268.1; 548/492; 548/518; 548/953

(58) Field of Classification Search
CPC ............................ A61K 31/498; C07D 241/44
USPC ........... 514/249; 540/607; 544/355; 546/245, 546/268.1; 548/492, 518, 953
See application file for complete search history.

(56) References Cited

U.S. PATENT DOCUMENTS 7,053,104 B2 * 5/2006 Van Wagenen et al. ...... 514/311

FOREIGN PATENT DOCUMENTS

| WO | WO 92/11245 | * 7/1992 |
| WO | 2010/056631 | 5/2010 |
| WO | 2011/043994 | 4/2011 |

OTHER PUBLICATIONS

Ahmad, et al. Bulletin of the Chemical Society of Japan, 38(10), 1965, 1659-1663.*
Hoffmann, et al. Journal of Organic Chemistry, 56(22), 1991, 6435-6439.*
Gervais et al., "Pharmacological characterization of MK-7246 . . . ", Molecular Pharmacology (2011), vol. 79, pp. 69-76.
Lan et al., "Small-molecule inhibitors of FABP4/5 ameliorate . . . ", J. Lipid Research (2011), vol. 52, pp. 646-656.
Furuhashi et al., "Treatment of diabetes and atherosclerosis . . . ", Nature (2007), vol. 447, pp. 959-965.
Roden, "Blocking fatty acids' mystery tour . . . ", Cell Metabolism (2007), vol. 6, pp. 89-91.
Makowski et al., "The role of fatty acid binding proteins . . . ", Curr. Opin. Lipidology (2005), vol. 16, pp. 543-548.

* cited by examiner

*Primary Examiner* — Douglas M Willis
(74) *Attorney, Agent, or Firm* — Anna L. Cocuzzo; Catherine D. Fitch

(57) ABSTRACT

The present invention relates to novel quinoxaline compounds of Formula I:

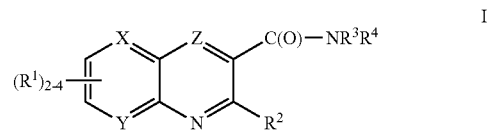

as Fatty Acid Binding Protein ("FABP") inhibitors, pharmaceutical compositions comprising the quinoxaline compounds and the use of the quinoxaline compounds for treating or preventing a cardiovascular disease, a metabolic disorder, obesity or an obesity-related disorder, diabetes, dyslipidemia, a diabetic complication, impaired glucose tolerance or impaired fasting glucose.

9 Claims, No Drawings

SUBSTITUTED QUINOXALINES AS INHIBITORS OF FATTY ACID BINDING PROTEIN

FIELD OF THE INVENTION

The present invention relates to compounds useful as Fatty Acid Binding Protein ("FABP") inhibitors, pharmaceutical compositions containing the compounds, and methods of treatment using the compounds and compositions to treat or prevent various diseases including cardiovascular disease, metabolic disorder, dyslipedemia, obesity and diabetes (e.g., Type 2 diabetes).

BACKGROUND OF THE INVENTION

The global prevalence of obesity is increasing epidemically. Obesity causes an array of health problems, reduces life expectancy, and costs over US $100 billion annually. More than a quarter of the population suffers from an aggregation of co-morbidities, including obesity, atherosclerosis, insulin resistance, dyslipidemias, coagulapathies, hypertension, and a pro-inflammatory state known as the metabolic syndrome. Patients with metabolic syndrome have high risk of atherosclerosis as well as type 2 diabetes and other health problems. Like obesity, atherosclerosis has very limited therapeutic options.

Atherosclerosis is the leading cause of death in the United States. At the core of this syndrome is the dysregulation of lipid metabolism and aberrant inflammatory responses. Although mechanistic roles for fatty acids have been put forward in the formation of obesity and diabetes by modifying glucose and lipid metabolism as well as inflammatory cascades, little is known about the mechanisms that link fatty acids or other lipid signals to inflammatory responses and the formation of atherosclerotic lesions. The biology of fatty acid binding proteins (FABPs) in several mouse models with targeted mutations in adipocyte/macrophage isoforms of these proteins has been investigated. Although serum fatty acid levels are not reduced in these FABP-deficient models, they are strikingly and paradoxically protected from obesity, insulin resistance, type 2 diabetes, fatty liver disease and atherosclerosis. This phenotype emphasizes the fact that total fatty acids may not be the primary pathogenic indicator, and that individual fatty acid or metabolite action at the intracellular level and the specific responses evoked by these signals are more relevant to the pathophysiology and outcomes of atherosclerotic disease than parameters classically measured.

Lipids and lipid signals are critical in the integration of metabolic and integration of metabolic and inflammatory response systems and consequently play significant parts in the pathogenesis of a cluster of chronic metabolic diseases, including type 2 diabetes, fatty liver disease and atherosclerosis. However, how lipids couple to target signaling pathways or metabolic processes and how their intracellular trafficking is regulated are poorly understood. Cytoplasmic fatty-acid-binding proteins (FABPs) are a family of 14-15-kDa proteins that bind with high affinity to hydrophobic ligands such as saturated and unsaturated long-chain fatty acids and eicosanoids such as hydroxyeicosatetra-enoic acid, leukotrienes and prostaglandins. The adipocyte FABP, aP2 (FABP4), is highly expressed in adipocytes and regulated by peroxisome-proliferator-activated receptor-γ (PPAR γ) agonists, insulin and fatty acids.

Impared insulin action at its target tissues, a phenomenon termed insulin resistance, is typical in obesity, type 2 diabetes, and associated atherosclerosis but also occurs during inflammatory and neoplastic processes. The development of insulin resistance has been linked to augmented availability of lipids and other nutrients. Specifically, plasma concentrations of free fatty acids (FFAs) are elevated in insulin resistance and even predict type 2 diabetes. Over past years, evidence has accumulated that FFAs induce insulin resistance by raising intracellular lipid metabolites.

The concentrations of FFAs can increase either in the circulating blood due to high-fat diet and release by adipocytes or within cells consequent to lipolysis or de novo synthesis. FFAs traffic through the body mainly while bound to fatty acid transport proteins, whereas fatty acid-binding proteins (FABPs) regulate their intracellular fate. In this regard, FABPs include, for example FABP2, FABP3, FABP4, FABP5, etc. Specifically, the adipocyte-specific isoform (FABP4, A-FABP, ALBP or aP2) has gained attention for its proposed role in metabolic disorders and atherosclerosis.

There is a need for additional ways of treating diseases associated metabolic syndrome such as, for example, dyslipedemia, obesity and diabetes (e.g., Type 2 diabetes).

Furthermore, Fatty acid binding proteins integrate metabolic and immune responses and link the inflammatory and lipid-mediated pathways that are critical in the metabolic syndrome.

The link between FABPs and the various diseases stated above is discussed by Roden et al, *Cell Metabolism* (2007) 6, pp. 89-91; Furuhashi et al, *Nature* (2007) 447, pp. 959-965; and Makowski et al, *Current Opinion Lipidology* (2005) 16, pp. 543-547.

A need exits in the art for FABP inhibitors, especially FABP4 inhibitors, that are effective for the treatment of metabolic disorders such as obesity, type II diabetes mellitus and metabolic syndrome.

A need exits in the art for FABP inhibitors, especially FABP5 inhibitors, that are effective for the treatment of metabolic disorders such as obesity, type II diabetes mellitus and metabolic syndrome.

A need exits in the art for FABP inhibitors, especially FABP3 inhibitors, that that are effective for the treatment of metabolic disorders such as obesity, type II diabetes mellitus and metabolic syndrome.

A need also exits in the art for dual FABP inhibitors that have efficacy in the treatment and/or prevention of cardiovascular conditions.

SUMMARY OF THE INVENTION

The present invention relates to compounds of formula I and pharmaceutically acceptable salts thereof that are useful for the treatment of metabolic disorders such as diabetes. Pharmaceutical compositions and methods of treatment are also included.

DETAILED DESCRIPTION OF THE INVENTION

In one embodiment, the present invention relates to compounds of Formula I, or pharmaceutically acceptable salts thereof.

In another embodiment, the present invention relates to compounds of formula I:

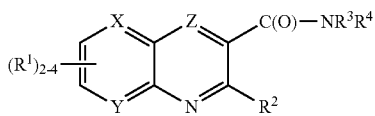

as well as the pharmaceutically acceptable salts thereof, wherein:

each of X, Y and Z represent C or N atoms;
each $R^1$ is H or is selected from the group consisting of: halo, CN, OH, $C_{1-6}$alkyl, $OC_{1-6}$alkyl, halo$C_{1-6}$alkyl, $OC_{1-6}$haloalkyl, $S(O)_x C_{1-6}$alkyl, and $S(O)_x C_{1-6}$haloalkyl, wherein x is 0, 1 or 2;

$R^2$ represents OH, halo, $C_{1-6}$alkyl, $OC_{1-6}$alkyl, $C_{1-6}$haloalkyl, $OC_{1-6}$haloalkyl, $NH_2$, $NHC_{1-6}$alkyl and $N(C_{1-6}alkyl)_2$, the alkyl portions of $NHC_{1-6}$alkyl and $N(C_{1-6}alkyl)_2$ being optionally substituted with 1-3 halo atoms;

one of $R^3$ and $R^4$ is selected from the group consisting of H and $C_{1-6}$alkyl, and the other is selected from the group consisting of:
a) $C_{1-6}$alkyl optionally substituted with 1-3 halo atoms and 1-2 $Aryl(R^a)_3$, $C_{3-7}cycloalkyl(R^a)_3$ or $Heteroaryl(R^a)_3$ groups;
b) $Cycloalkyl(R^a)_3$;
c) $Aryl(R^a)_3$ and $Heteroaryl(R^a)_3$;
wherein each $R^a$ represents H, halo, OH, $C_{1-6}$alkyl, halo$C_{1-6}$alkyl, $C_{3-7}$cycloalkyl, $OC_{1-6}$alkyl or $OC_{1-6}$halolalkyl, or 2 $R^a$ groups taken together represents a fused aromatic ring;

or $R^3$ and $R^4$ are taken together and represent a 4-7 membered ring, optionally containing 0-2 heteroatoms selected from O, S and N in addition to the N atom to which they are attached, said ring being optionally substituted with 1-3 groups selected from $R^b$;

each $R^b$ is selected from the group consisting of:
a) $C_{1-6}$alkyl optionally substituted with 1-2 Aryl, Heteroaryl, Heterocyclyl, Cycloalkyl, $O-C_{1-6}$Alkyl, O-Aryl, O-Heteroaryl, $NH-C_{1-6}$Alkyl, NH-Aryl, NH-Heteroaryl, groups, the Aryl, Heteroaryl, Heterocyclyl and Alkyl portions being further optionally substituted with 1-3 $C_{1-3}$alkyl, halo, $OC_{1-6}$alkyl, $C_{1-6}$haloalkyl and $OC_{1-6}$haloalkyl groups;
b) $CO_2C_{1-6}$Alkyl, $CO_2$-Aryl, $CO_2$-Heteroaryl, and $CO_2$ $C_{3-6}$Cycloalkyl, each being optionally substituted with 1-2 $C_{1-3}$ alkyl, halo, Aryl, Heteroaryl, Heterocyclyl, Cycloalkyl, $O-C_{1-6}$Alkyl, $NH-C_{1-6}$Alkyl, and NH-Aryl groups, the Aryl, Heteroaryl, and Heterocyclyl portions, and the alkyl portions of $O-C_{1-6}$Alkyl and $NH-C_{1-6}$Alkyl being further optionally substituted with 1-3 $C_{1-6}$alkyl, halo, $OC_{1-6}$alkyl, halo$C_{1-6}$alkyl and $OC_{1-6}$haloalkyl groups;
c) Aryl, Heteroaryl, Heterocyclyl, Cycloalkyl, $O-C_{1-6}$ Alkyl, $NH-C_{1-6}$Alkyl, NH-Aryl, each being optionally substituted with 1-3 alkyl, halo, $OC_{1-6}$alkyl, halo$C_{1-6}$alkyl and $OC_{1-6}$haloalkyl groups;
or 2 $R^b$ groups are taken together and represent a fused phenyl ring, optionally substituted with 1-3 halo atoms or $C_{1-6}$alkyl groups.

In another embodiment of the invention, a compound of formula I or a pharmaceutically acceptable salt or solvate thereof is disclosed, wherein X and Y represent carbon atoms and Z represents a nitrogen atom.

In another embodiment of the invention, a compound of formula I or a pharmaceutically acceptable salt or solvate thereof is disclosed, wherein Y represents a carbon atom and X and Z represent nitrogen atoms.

In another embodiment of the invention, a compound of formula I or a pharmaceutically acceptable salt or solvate thereof is disclosed, wherein X represents a carbon atom and Y and Z represent nitrogen atoms.

In another embodiment of the invention, a compound of formula I or a pharmaceutically acceptable salt or solvate thereof is disclosed, wherein each $R^1$ is selected from H, F, Cl and I.

In another embodiment of the invention, a compound of formula I or a pharmaceutically acceptable salt or solvate thereof is disclosed, wherein 1-2 $R^1$ groups are selected from F and Cl, and the remainder of the $R^1$ groups are selected from H, F, Cl, Br, I, CN, $C_{1-3}$alkyl, halo$C_{1-3}$alkyl, $OC_{1-3}$alkyl, $OC_{1-3}$haloalkyl, $SC_{1-3}$alkyl, $SC_{1-3}$haloalkyl, $SO_2C_{1-3}$alkyl and $SO_2C_{1-3}$haloalkyl.

In another embodiment of the invention, a compound of formula I or a pharmaceutically acceptable salt or solvate thereof is disclosed, wherein $R^2$ is selected from OH, $NH_2$, $C_1$, $C_{1-3}$alkyl and $C_{1-3}$haloalkyl.

In another embodiment of the invention, a compound of formula I or a pharmaceutically acceptable salt or solvate thereof is disclosed, wherein one of $R^3$ and $R^4$ is H or $C_{1-3}$alkyl, and the other is:
a) $C_{1-3}$alkyl optionally substituted with 1-3 halo atoms and 1 $Aryl(R^a)_3$, $C_{3-7}cycloalkyl(R^a)_3$ or $Heteroaryl(R^a)_3$ group;
and further wherein each $R^a$ represents H, halo, OH, $C_{1-4}$alkyl, halo$C_{1-3}$alkyl, $C_{3-7}$cycloalkyl, $OC_{1-3}$alkyl or $OC_{1-3}$halolalkyl.

In another embodiment of the invention, a compound of formula I or a pharmaceutically acceptable salt or solvate thereof is disclosed, wherein one of $R^3$ and $R^4$ is H or $C_{1-3}$alkyl, and the other is:
b) $Cycloalkyl(R^a)_3$;
wherein each $R^a$ represents H, halo, OH, $C_{1-6}$alkyl, halo$C_{1-6}$alkyl, $C_{3-7}$cycloalkyl, $OC_{1-6}$alkyl or $OC_{1-6}$halolalkyl, or 2 $R^a$ groups taken together represents a fused aromatic ring;

In another embodiment of the invention, a compound of formula I or a pharmaceutically acceptable salt or solvate thereof is disclosed, wherein one of $R^3$ and $R^4$ is H or $C_{1-3}$alkyl, and the other is:
c) $Aryl(R^a)_3$ or $Heteroaryl(R^a)_3$;
wherein each $R^a$ represents H, halo, OH, $C_{1-6}$alkyl, halo$C_{1-6}$alkyl, $C_{3-7}$cycloalkyl, $OC_{1-6}$alkyl or $OC_{1-6}$halolalkyl.

In another embodiment of the invention, a compound of formula I or a pharmaceutically acceptable salt or solvate thereof is disclosed, wherein $R^3$ and $R^4$ are taken together and represent a 4-7 membered ring, optionally containing 0-2 heteroatoms selected from O, S and N in addition to the N atom to which they are attached, said ring being optionally substituted with 1-3 groups selected from $R^b$;

each $R^b$ is selected from the group consisting of:
a) $C_{1-6}$alkyl optionally substituted with 1-2 Aryl, Heteroaryl, Heterocyclyl, Cycloalkyl, $O-C_{1-6}$Alkyl, O-Aryl, O-Heteroaryl, $NH-C_{1-6}$Alkyl, NH-Aryl, or NH-Heteroaryl groups, the Aryl, Heteroaryl, Heterocyclyl and Alkyl portions being further optionally substituted with 1-3 $C_{1-3}$alkyl, halo, $OC_{1-6}$alkyl, $C_{1-6}$haloalkyl and $OC_{1-6}$haloalkyl groups;
b) $CO_2C_{1-6}$Alkyl, $CO_2$-Aryl, $CO_2$-Heteroaryl, and $CO_2$ $C_{3-6}$Cycloalkyl, each being optionally substituted with 1-2 $C_{1-3}$ alkyl, halo, Aryl, Heteroaryl, Heterocyclyl, Cycloalkyl, $O-C_{1-6}$Alkyl, $NH-C_{1-6}$Alkyl, and NH-Aryl groups, the Aryl, Heteroaryl, and Heterocyclyl portions, and the Alkyl portions of $O-C_{1-6}$Alkyl and $NH-C_{1-6}$Alkyl being further optionally substituted with 1-3 $C_{1-6}$alkyl, halo, $OC_{1-6}$alkyl, halo$C_{1-6}$alkyl and $OC_{1-6}$haloalkyl groups; and c) Aryl, Heteroaryl, Heterocyclyl, Cycloalkyl, O—$C_{1-6}$Alkyl, NH—$C_{1-6}$Alkyl, NH-Aryl, each being optionally substituted with 1-3 alkyl, halo, $OC_{1-6}$alkyl, halo$C_{1-6}$alkyl and $OC_{1-6}$haloalkyl groups;

or 2 $R^b$ groups are taken together and represent a fused phenyl ring, optionally substituted with 1-3 halo atoms or $C_{1-6}$alkyl groups.

In another embodiment of the invention, a compound of formula I or a pharmaceutically acceptable salt or solvate thereof is disclosed, wherein $R^3$ and $R^4$ are taken together and represent a 4, 5, or 6 membered ring, optionally containing 0-1 heteroatom selected from O, S and N in addition to the N atom to which they are attached, said ring being optionally substituted with 1-2 groups selected from $R^b$;

each $R^b$ is selected from the group consisting of:

a) $C_{1-3}$ alkyl optionally substituted with 1 Aryl, Heteroaryl, Heterocyclyl, Cycloalkyl, NH—$C_{1-3}$Alkyl, NH-Aryl, or NH-Heteroaryl groups, the Aryl, Heteroaryl, Heterocyclyl and Alkyl portions being further optionally substituted with 1-3 $C_{1-3}$alkyl, halo, $OC_{1-3}$alkyl, $C_{1-3}$haloalkyl and $OC_{1-3}$haloalkyl groups;

b) $CO_2C_{1-3}$Alkyl, $CO_2$-Aryl, $CO_2$-Heteroaryl, and $CO_2C_{3-6}$Cycloalkyl, each being optionally substituted with 1 $C_{1-3}$Alkyl, halo, Aryl, Heteroaryl, Heterocyclyl, Cycloalkyl, O—$C_{1-3}$Alkyl, NH—$C_{1-3}$Alkyl, and NH-Aryl group, the Aryl, Heteroaryl, and Heterocyclyl portions, and the Alkyl portions of O—$C_{1-3}$Alkyl and NH—$C_{1-3}$Alkyl being further optionally substituted with 1-3 $C_{1-3}$alkyl, halo, $OC_{1-3}$ alkyl, halo$C_{1-3}$ alkyl and $OC_{1-3}$haloalkyl groups; and c) Aryl, Heteroaryl, Heterocyclyl, Cycloalkyl, O—$C_{1-3}$ Alkyl, NH—$C_{1-3}$Alkyl, NH-Aryl, each being optionally substituted with 1-3 alkyl, halo, $OC_{1-3}$ alkyl, halo$C_{1-3}$alkyl and $OC_{1-3}$haloalkyl groups;

or 2 $R^b$ groups are taken together and represent a fused phenyl ring, optionally substituted with 1-3 halo atoms.

Another aspect of the invention that is of interest relates to a compound of formula I or a pharmaceutically acceptable salt or solvate thereof wherein:

each of X, Y and Z represent C or N atoms;

each $R^1$ is selected from H, F, Cl and I, or 1-2 $R^1$ groups are selected from F and Cl, and the remainder of the $R^1$ groups are selected from H, F, Cl, Br, I, CN, $C_{1-3}$alkyl, halo$C_{1-3}$alkyl, $OC_{1-3}$alkyl, $OC_{1-3}$haloalkyl, $SC_{1-3}$alkyl, $SC_{1-3}$haloalkyl, $SO_2C_{1-3}$alkyl and $SO_2C_{1-3}$haloalkyl;

$R^2$ is selected from OH, $NH_2$, $C_1$, $C_{1-3}$alkyl and $C_{1-3}$haloalkyl;

one of $R^3$ and $R^4$ is H or $C_{1-3}$alkyl, and the other is:

a) $C_{1-3}$alkyl optionally substituted with 1-3 halo atoms and 1 Aryl($R^a$)$_3$, $C_{3-7}$cycloalkyl($R^a$)$_3$ or Heteroaryl($R^a$)$_3$ group;

and further wherein each $R^a$ represents H, halo, OH, $C_{1-4}$alkyl, halo$C_{1-3}$ alkyl, $C_{3-7}$cycloalkyl, $OC_{1-3}$ alkyl or $OC_{1-3}$halolalkyl;

b) Cycloalkyl($R^a$)$_3$;

wherein each $R^a$ represents H, halo, OH, $C_{1-6}$alkyl, halo $C_{1-6}$alkyl, $C_{3-7}$cycloalkyl, $OC_{1-6}$alkyl or $OC_{1-6}$halolalkyl, or 2 $R^a$ groups taken together represents a fused aromatic ring;

c) Aryl($R^a$)$_3$ or Heteroaryl($R^a$)$_3$;

wherein each $R^a$ represents H, halo, OH, $C_{1-6}$alkyl, halo $C_{1-6}$alkyl, $C_{3-7}$cycloalkyl, $OC_{1-6}$ alkyl or $OC_{1-6}$halolalkyl, or $R^3$ and $R^4$ are considered together and represent a 4, 5, or 6 membered ring, optionally containing 0-1 heteroatom selected from O, S and N in addition to the N atom to which they are attached, said ring being optionally substituted with 1-2 groups selected from $R^b$;

each $R^b$ is selected from the group consisting of:

a) $C_{1-3}$ alkyl optionally substituted with 1 Aryl, Heteroaryl, Heterocyclyl, Cycloalkyl, NH—$C_{1-3}$Alkyl, NH-Aryl, or NH-Heteroaryl groups, the Aryl, Heteroaryl, Heterocyclyl and Alkyl portions being further optionally substituted with 1-3 $C_{1-3}$alkyl, halo, $OC_{1-3}$alkyl, $C_{1-3}$haloalkyl and $OC_{1-3}$haloalkyl groups;

b) $CO_2C_{1-3}$Alkyl, $CO_2$-Aryl, $CO_2$-Heteroaryl, and $CO_2C_{3-6}$Cycloalkyl, each being optionally substituted with 1 $C_{1-3}$Alkyl, halo, Aryl, Heteroaryl, Heterocyclyl, Cycloalkyl, O—$C_{1-3}$Alkyl, NH—$C_{1-3}$Alkyl, and NH-Aryl group, the Aryl, Heteroaryl, and Heterocyclyl portions, and the Alkyl portions of O—$C_{1-3}$Alkyl and NH—$C_{1-3}$Alkyl being further optionally substituted with 1-3 $C_{1-3}$alkyl, halo, $OC_{1-3}$alkyl, halo$C_{1-3}$ alkyl and $OC_{1-3}$haloalkyl groups; and c) Aryl, Heteroaryl, Heterocyclyl, Cycloalkyl, O—$C_{1-3}$ Alkyl, NH—$C_{1-3}$Alkyl, NH-Aryl, each being optionally substituted with 1-3 alkyl, halo, $OC_{1-3}$alkyl, halo$C_{1-3}$alkyl and $OC_{1-3}$haloalkyl groups;

or 2 $R^b$ groups are taken together and represent a fused phenyl ring, optionally substituted with 1-3 halo atoms.

Species that are considered as part of the invention are disclosed in Tables A, B and C.

As used herein, the term "Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

As used herein, the term "Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

As used herein, the term "Alkylene" means a difunctional group obtained by removal of a hydrogen atom from an alkyl group that is defined above. Non-limiting examples of alkylene include methylene, ethylene and propylene.

As used herein, the term "Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

As used herein, the term "Aryl" means an aromatic monocyclic or multicyclic ring system comprising about 6 to about 14 carbon atoms, preferably about 6 to about 10 carbon atoms. The Aryl group can be optionally substituted with one or more "ring system substituents" which may be the same or different, and are as defined herein. Non-limiting examples of suitable aryl groups include phenyl and naphthyl.

As used herein, the term "Heteroaryl" (HAR) means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

As used herein, the term "Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the Aryl moiety is through the alkyl portion.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the Alkyl moiety is through the Aryl portion.

As used herein, the term "Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

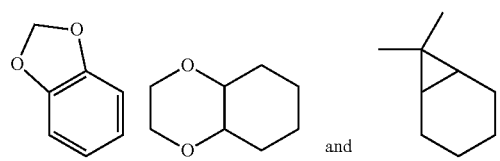

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

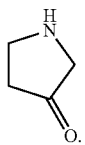

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

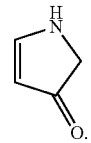

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

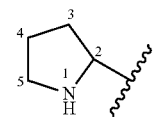

there is no —OH attached directly to carbons marked 2 and 5.
It should also be noted that tautomeric forms such as, for example, the moieties:

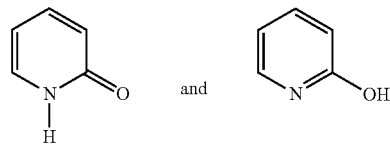 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an Alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an Aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-$SO_2$— group. The bond to the parent moiety is through the sulfonyl.

The term 'spirocyclyl' refers to a cyclic group substituted off the same carbon atom. A non-limiting example is:

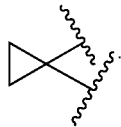 [SMILES: *C1(*)CC1]

As used above, and throughout this disclosure, the following terms, unless otherwise indicated, shall be understood to have the following meanings:

"Patient" includes both humans and animals.

"Mammal" means humans and other mammalian animals.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula I, or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I, or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoaryl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —$C(OH)C(O)OY^1$ wherein $Y^1$ is H, ($C_1$-$C_6$)alkyl or benzyl, —$C(OY^2)Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N— or di-N,N—($C_1$-$C_6$)alkylaminoalkyl, —$C(Y^4)Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and the invention includes both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, (2004) 93(3), pp. 601-611 describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, (2004) 5(1), article 12; and A. L. Bingham et al, *Chem. Commun.*, (2001) pp. 603-604. A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective" or 'therapeutically effective" is used herein, unless otherwise indicated, to describe an amount of a compound or composition which, in context, is used to produce or effect an intended result or therapeutic effect as understood in the common knowledge of those skilled in the art.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) pp. 1-19; P. Gould, *International J. of Pharmaceutics* (1986) (2001) 33 pp. 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I and salts, solvates, esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention further includes the compounds of the invention in their isolated forms.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I and of the salts, solvates, esters and prodrugs of the compounds of Formula I are intended to be included in the present invention.

The compounds according to the invention have pharmacological properties. The compounds of Formula I are inhibitors of FABP, particularly FABP4, and can be useful for the therapeutic and/or prophylactic treatment of diseases that are modulated by FABP, particularly by FABP4, such as, for example, metabolic syndrome, diabetes (e.g., Type 2 diabetes mellitus), obesity and the like.

The invention also includes methods of treating diseases that are modulated by FABP, particularly by FABP4.

The invention also includes methods of treating metabolic syndrome, diabetes (e.g., Type 2 diabetes mellitus), and obesity in a patient by administering at least one compound of Formula I to said patient.

Diabetes refers to a disease process derived from multiple causative factors and is characterized by elevated levels of plasma glucose, or hyperglycemia in the fasting state or after administration of glucose during an oral glucose tolerance test. Persistent or uncontrolled hyperglycemia is associated with increased and premature morbidity and mortality. Abnormal glucose homeostasis is associated with alterations of the lipid, lipoprotein and apolipoprotein metabolism and other metabolic and hemodynamic disease. As such, the diabetic patient is at especially increased risk of macrovascular and microvascular complications, including coronary heart disease, stroke, peripheral vascular disease, hypertension, nephropathy, neuropathy, and retinopathy. Accordingly, therapeutic control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissue (muscle, liver and adipose tissue), and the plasma insulin levels, while elevated, are insufficient to overcome the pronounced insulin resistance.

Insulin resistance is not associated with a diminished number of insulin receptors but rather to a post-insulin receptor binding defect that is not well understood. This resistance to insulin responsiveness results in insufficient insulin activation of glucose uptake, oxidation and storage in muscle, and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic [beta]-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a class of agents that can increase insulin sensitivity and bring about some degree of correction of hyperglycemia. However, the biguanides can induce lactic acidosis and nausea/diarrhea.

In another aspect, this invention provides compositions comprising at least one compound of Formula I.

In another aspect, this invention provides pharmaceutical compositions comprising at least one compound of Formula I and at least one pharmaceutically acceptable carrier.

In another aspect, this invention provides a method of treating diabetes in a patient in need of such treatment using therapeutically effective amounts of at least one compound of Formula I, or of a composition comprising at least one compound of Formula I.

In another aspect, this invention provides a method of treating diabetes in a patient in need of such treatment, e.g., Type 2 diabetes, using therapeutically effective amounts of at least one compound of Formula I, or of a composition comprising at least one compound of Formula I.

In another aspect, this invention provides a method of treating metabolic syndrome in a patient in need of such treatment, using therapeutically effective amounts of at least one compound of Formula I, or of a composition comprising at least one compound of Formula I.

In another aspect, this invention provides a method of treating dyslipidemia in a patient in need of such treatment, using therapeutically effective amounts of at least one compound of Formula I, or of a composition comprising at least one compound of Formula I.

In another aspect, this invention provides a method of treating or preventing a cardiovascular condition in a patient in need of such treatment, using therapeutically effective amounts of at least one compound of Formula I, or of a composition comprising at least one compound of Formula I.

In another aspect, this invention provides a method of treating obesity in a patient in need of such treatment, using therapeutically effective amounts of at least one compound of Formula I, or of a composition comprising at least one compound of Formula I.

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 5 ("FABP5").

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 4 ("FABP4").

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP4 and FABP5.

This invention further provides methods of using at least one compound of Formula I, or pharmaceutically acceptable salt, solvate, ester or prodrug of said compound, or pharmaceutically acceptable salt, solvate or ester of said prodrug, for inhibiting Fatty Acid Binding Protein ("FABP") inhibitors, especially Fatty Acid Binding Protein 3 ("FABP3").

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP3 and FABP4.

This invention further provides methods of using at least one compound of Formula I, or pharmaceutically acceptable salt, solvate, ester or prodrug of said compound, or pharmaceutically acceptable salt, solvate or ester of said prodrug, for inhibiting both FABP3 and FABP5.

This invention further provides methods of using at least one compound of Formula I, or pharmaceutically acceptable salt, solvate, ester or prodrug of said compound, or pharmaceutically acceptable salt, solvate or ester of said prodrug, for inhibiting FABP3, FABP4 and FABP5.

In another aspect, this invention provides a method of inhibiting FABP using therapeutically effective amounts of a composition comprising at least one compound of Formula I.

In another aspect, this invention provides a method of inhibiting FABP4, or FABP3, or FABP5, using therapeutically effective amounts of a composition comprising at least one compound of Formula I.

In another aspect, this invention provides a method of inhibiting both FABP4 and FABP5 using therapeutically effective amounts of a composition comprising at least one compound of Formula I.

In another aspect, this invention provides a method of inhibiting both FABP3 and FABP5 using therapeutically effective amounts of a composition comprising at least one compound of Formula I.

In another aspect, this invention provides a method of inhibiting both FABP3 and FABP4 using therapeutically effective amounts of a composition comprising at least one compound of Formula I.

In another aspect, this invention provides a method of inhibiting FABP3, FABP4 and FABP5 using therapeutically effective amounts of a composition comprising at least one compound of Formula I.

In another aspect, this invention provides a method of inhibiting FABP using therapeutically effective amounts of at least one compound of Formula I, and therapeutically effective amounts of at least one other therapeutic agent.

In another aspect, this invention provides a method of inhibiting FABP4, or FABP3 or FABP5, using therapeutically effective amounts of at least one compound of Formula I, and therapeutically effective amounts of at least one other therapeutic agent.

In another aspect, this invention provides a method of inhibiting both FABP4 and FABP5 using therapeutically effective amounts of a composition comprising at least one compound of Formula I, and therapeutically effective amounts of at least one other therapeutic agent.

In another aspect, this invention provides a method of inhibiting both FABP3 and FABP5 using therapeutically effective amounts of a composition comprising at least one compound of Formula I, and therapeutically effective amounts of at least one other therapeutic agent.

In another aspect, this invention provides a method of inhibiting both FABP4 and FABP3 using therapeutically effective amounts of a composition comprising at least one compound of Formula I, and therapeutically effective amounts of at least one other therapeutic agent.

In another aspect, this invention provides a method of inhibiting FABP3, FABP4 and FABP5, using therapeutically effective amounts of a composition comprising at least one compound of Formula I, and therapeutically effective amounts of at least one other therapeutic agent.

In another aspect, this invention provides a method of treating or preventing a cardiovascular condition in a patient in need of such treatment, using therapeutically effective amounts of at least one compound of Formula I, and therapeutically effective amounts of at least one other therapeutic agent.

In another aspect, this invention provides a method of treating diabetes in a patient in need of such treatment using therapeutically effective amounts of at least one compound of Formula I, and therapeutically effective amounts of at least one other therapeutic agent.

In another aspect, this invention provides a method of treating diabetes in a patient in need of such treatment, e.g., Type 2 diabetes, using therapeutically effective amounts of at least one compound of Formula I, and therapeutically effective amounts of at least one other therapeutic agent.

In another aspect, this invention provides a method of inhibiting both FABP4 and FABP5 using therapeutically effective amounts of at least one compound of Formula I, or of a composition comprising at least one compound of Formula I.

The glitazones (i.e. 5-benzylthiazolidine-2,4-diones) are a separate class of compounds with potential for the treatment of type 2 diabetes. These agents increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have been noted in some patients treated with glitazone drugs, such as troglitazone.

Additional methods of treating the disease are currently under investigation. New biochemical approaches include treatment with alpha-glucosidase inhibitors (e.g. acarbose) and protein tyrosine phosphatase-1B (PTP-1B) inhibitors. Compounds that are inhibitors of the dipeptidyl peptidase-W (DPP-IV) enzyme are also under investigation as drugs that may be useful in the treatment of diabetes, and particularly type 2 diabetes.

The invention includes compositions, e.g., pharmaceutical compositions, comprising at least one compound of Formula I. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Other carriers include Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intrathecal, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient. Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions.

Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preferably the compound is administered orally, intraperitoneally, or intravenously or intrathecally or some suitable combination(s) thereof.

Methods of administering small molecule therapeutic agents are well-known in the art.

The therapeutic agents described in the present disclosure can be administered to a subject alone or together (coadministered, optionally but not necessarily, in a single formulation) with other active agents as described herein, and are preferably administered with a pharmaceutically acceptable buffer. The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from as low as about 0.1 mg/day to as high as about 5000 mg/day, preferably about 1 mg/day to about 500 mg/day, in one to four divided doses, and more preferably about 1 mg/day to about 100 mg/day, in one or two doses per day.

Another aspect of this invention is a kit comprising a therapeutically effective amount of at least one compound of Formula I, or a pharmaceutically acceptable salt, solvate, ester or prodrug of said compound and a pharmaceutically acceptable carrier, vehicle or diluent.

Another aspect of the invention includes pharmaceutical compositions comprising at least one compound of Formula I and at least one other therapeutic agent in combination. Non-limiting examples of such combination agents are described below. The agents in the combination can be administered together as a joint administration (e.g., joint single pill), separately, one after the other in any order and the like as is well known in the art.

In the combination therapies of the present invention, an effective amount can refer to each individual agent or to the combination as a whole, wherein the amounts of all agents administered are together effective, but wherein the component agent of the combination may not be present individually in an effective amount.

Combination Therapy

Accordingly, in one embodiment, the present invention provides methods for treating a Condition in a patient, the method comprising administering to the patient one or more Compounds of Formula I or a pharmaceutically acceptable salt or solvate thereof and at least one additional therapeutic agent that is not a Compound of Formula I wherein the amounts administered are together effective to treat or prevent a Condition.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Compounds of Formula I is administered during at time when the additional therapeutic agent(s) exert their prophylactic or therapeutic effect, or vice versa.

In another embodiment, the one or more Compounds of Formula I and the additional therapeutic agent(s) are administered in doses commonly employed when such agents are used as monotherapy for treating a Condition.

In another embodiment, the one or more Compounds of Formula I and the additional therapeutic agent(s) are administered in doses lower than the doses commonly employed when such agents are used as monotherapy for treating a Condition.

In still another embodiment, the one or more Compounds of Formula I and the additional therapeutic agent(s) act synergistically and are administered in doses lower than the doses commonly employed when such agents are used as monotherapy for treating a Condition.

In one embodiment, the one or more Compounds of Formula I and the additional therapeutic agent(s) are present in the same composition. In one embodiment, this composition is suitable for oral administration. In another embodiment, this composition is suitable for intravenous administration.

The one or more Compounds of Formula I and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Compounds of Formula I and the additional therapeutic agent(s) may inhibit the resistance of a Condition to these agents.

In one embodiment, when the patient is treated for diabetes, a diabetic complication, impaired glucose tolerance or impaired fasting glucose, the other therapeutic is an antidiabetic agent which is not a Compound of Formula I. In another embodiment, when the patient is treated for pain, the other therapeutic agent is an analgesic agent which is not a Compound of Formula I.

In another embodiment, the other therapeutic agent is an agent useful for reducing any potential side effect of a Compound of Formula I. Such potential side effects include, but are not limited to, nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

Examples of antidiabetic agents useful in the present methods for treating diabetes or a diabetic complication include a sulfonylurea; an insulin sensitizer (such as a PPAR agonist, a DPP-IV inhibitor, a PTP-1B inhibitor and a glucokinase activator); a glucosidase inhibitor; an insulin secretagogue; a hepatic glucose output lowering agent; an anti-obesity agent; an antihypertensive agent; a meglitinide; an agent that slows or blocks the breakdown of starches and sugars in vivo; an histamine $H_3$ receptor antagonist; an antihypertensive agent, a sodium glucose uptake transporter 2 (SGLT-2) inhibitor; a peptide that increases insulin production; and insulin or any insulin-containing composition.

In one embodiment, the antidiabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

Non-limiting examples of insulin sensitizers include PPAR activators, such as troglitazone, rosiglitazone, pioglitazone and englitazone; biguanidines such as metformin and phenformin; DPP-IV inhibitors; PTP-1B inhibitors; and α-glucokinase activators, such as miglitol, acarbose, and voglibose.

Non-limiting examples of DPP-IV inhibitors useful in the present methods include sitagliptin (Januvia™, Merck), saxagliptin, denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of hepatic glucose output lowering agents include Glucophage and Glucophage XR.

Non-limiting examples of histamine $H_3$ receptor antagonist agents include the following compound:

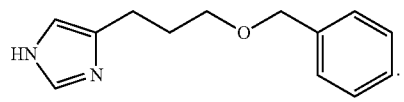 [SMILES: c1ccc(COCCCc2c[nH]cn2)cc1]

Non-limiting examples of insulin secretagogues include sulfonylurea and non-sulfonylurea drugs such as GLP-1, a GLP-1 mimetic, exendin, GIP, secretin, glipizide, chlorpropamide, nateglinide, meglitinide, glibenclamide, repaglinide and glimepiride.

Non-limiting examples of GLP-1 mimetics useful in the present methods include Byetta-Exanatide, Liraglutinide, CJC-1131 (ConjuChem, Exanatide-LAR (Amylin), BIM-51077 (Ipsen/LaRoche), ZP-10 (Zealand Pharmaceuticals), and compounds disclosed in International Publication No. WO 00/07617.

The term "insulin" as used herein, includes all pyridinones of insulin, including long acting and short acting forms of insulin.

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the antidiabetic agent is an anti-obesity agent.

Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

Non-limiting examples of antihypertensive agents useful in the present methods for treating diabetes include alpha and beta-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), and endothelin receptor antagonists (for example sitaxsentan).

Non-limiting examples of meglitinides useful in the present methods for treating diabetes include repaglinide and nateglinide.

Non-limiting examples of insulin sensitizing agents include biguanides, such as metformin, metformin hydrochloride (such as GLUCOPHAGE® from Bristol-Myers Squibb), metformin hydrochloride with glyburide (such as GLUCOVANCE™ from Bristol-Myers Squibb) and buformin; glitazones; and thiazolidinediones, such as rosiglitazone, rosiglitazone maleate (AVANDIA™ from GlaxoSmithKline), pioglitazone, pioglitazone hydrochloride (ACTOS™, from Takeda) ciglitazone and MCC-555 (Mitsubishi Chemical Co.)

In one embodiment, the insulin sensitizer is a thiazolidinedione.

In another embodiment, the insulin sensitizer is a biguanide.

In another embodiment, the insulin sensitizer is a DPP-IV inhibitor.

In a further embodiment, the antidiabetic agent is a SGLT-2 inhibitor.

Non-limiting examples of antidiabetic agents that slow or block the breakdown of starches and sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

Non-limiting examples of analgesic agents useful in the present methods for treating pain include acetaminophen, NSAIDs, opiates and tricyclic antidepressants.

In one embodiment, the other analgesic agent is acetaminophen or an NSAID.

In another embodiment, the other analgesic agent is an opiate.

In another embodiment, the other analgesic agent is a tricyclic antidepressant.

Non-limiting examples of NSAIDS useful in the present methods for treating pain include a salicylate, such as aspirin, amoxiprin, benorilate or diflunisal; an arylalkanoic acid, such as diclofenac, etodolac, indometacin, ketorolac, nabumetone, sulindac or tolmetin; a 2-arylpropionic acid (a "profen"), such as ibuprofen, carprofen, fenoprofen, flurbiprofen, loxoprofen, naproxen, tiaprofenic acid or suprofen; a fenamic acid, such as mefenamic acid or meclofenamic acid; a pyrazolidine derivative, such as phenylbutazone, azapropazone, metamizole or oxyphenbutazone; a coxib, such as celecoxib, etoricoxib, lumiracoxib or parecoxib; an oxicam, such as piroxicam, lornoxicam, meloxicam or tenoxicam; or a sulfonanilide, such as nimesulide.

Non-limiting examples of opiates useful in the present methods for treating pain include an anilidopiperidine, a phenylpiperidine, a diphenylpropylamine derivative, a benzomorphane derivative, an oripavine derivative and a morphinane derivative. Additional illustrative examples of opiates include morphine, diamorphine, heroin, buprenorphine, dipipanone, pethidine, dextromoramide, alfentanil, fentanyl, remifentanil, methadone, codeine, dihydrocodeine, tramadol, pentazocine, vicodin, oxycodone, hydrocodone, percocet, percodan, norco, dilaudid, darvocet or lorcet.

Non-limiting examples of tricyclic antidepressants useful in the present methods for treating pain include amitryptyline, carbamazepine, gabapentin or pregabalin.

The Compounds of Formula I can be combined with an $H_1$ receptor antagonist (i.e., the Compounds of Formula I can be combined with an $H_1$ receptor antagonist in a pharmaceutical composition, or the Compounds of Formula I can be administered with one or more $H_1$ receptor antagonists).

Numerous chemical substances are known to have histamine $H_1$ receptor antagonist activity and can therefore be used in the methods of this invention. Many $H_1$ receptor antagonists useful in the methods of this invention can be classified as ethanolamines, ethylenediamines, alkylamines, phenothiazines or piperidines. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine, diphenhydramine, ebastine, fexofenadine, loratadine, or norastemizole.

Even more preferably, said $H_1$ antagonist is selected from loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of a compound of Formula I is administered with a $H_1$ antagonist, the antagonists can be administered simultaneously or sequentially (first one and then the other over a period of time). In general, but not always, when the antagonists are administered sequentially, the compound of Formula I is administered first.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Compound(s) of Formula I, and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Compounds of Formula I and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

Synthesis

Purification Conditions

General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from Me$_4$Si with number of protons, multiplicities, and coupling constants in Hz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given. MS data were obtained using Agilent Technologies LC/MSD SL or 1100 series LC/MSD mass spectrometer. Final compounds were purified by Pre-pLC using the column of Varian Pursuit XRs C18 10 μm 250×21.2 mm and an eluent mixture of mobile phase A and B. The mobile phase A is composed of 0.1% TFA in H$_2$O and the mobile phase B is composed of CH$_3$CN (95%)/H$_2$O (5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 μm 150×4.6 mm column and an eluent mixture of mobile phase A and B, wherein mobile phase A is composed of 0.1% TFA in H$_2$O and the mobile phase B is composed of CH$_3$CN (95%)/H$_2$O (5%)/TFA (0.1%). The column was eluted at a flow rate of 3 mL/min at a temperature of 60° C. Intermediate compounds were characterized by LCMS using a Higgins Haisil HL C18 5 μm 50×4.6 mm column and an eluent mixture of mobile phase A and B, wherein mobile phase A is composed of 0.1% TFA in H$_2$O and the mobile phase B is composed of CH₃CN (95%)/H₂O (5%)/TFA (0.1%). The column was eluted at a flow rate of 3 mL/min at a column temperature of 60° C.

Post Purification

To each Vial was added 1 mL of acetonitrile and 1 mL of 1 N hydrochloric acid standard solution in water. The vials were shaken for few minutes and transferred into a bar-coded 4 mL scintillation vial previously tarred. The tubes were lyophilized overnight then weighed, yields were calculated.

Experimental Procedures

General Method 1

Preparation of (+/−)-[2-(3-chlorobenzyl)pyrrolidin-1-yl](6,7-difluoro-3-hydroxyquinoxalin-2-yl)methanone (1-2)

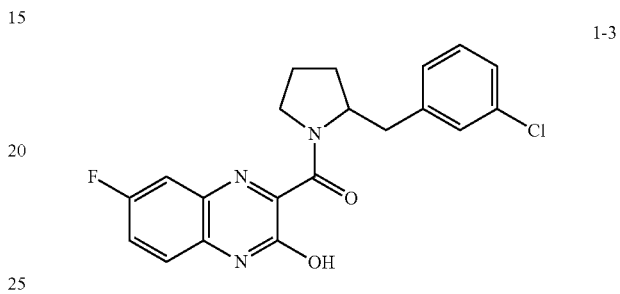

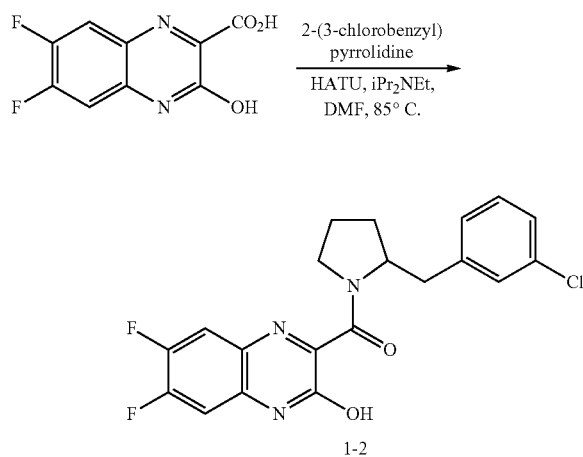 [SMILES: O=C(O)c1nc2cc(F)c(F)cc2nc1O ; O=C(c1nc2cc(F)c(F)cc2nc1O)N1CCCC1Cc1cccc(Cl)c1]

1-2

Diisopropylethylamine (0.32 mL, 1.8 mmol) was added dropwise to a mixture of 6,7-difluoro-3-hydroxyquinoxaline-2-carboxylic acid (100 mg, 0.44 mmol), racemic 2-(3-chlorobenzyl)pyrrolidine (72 mg, 0.37 mmol) and O-HATU (210 mg, 0.55 mmol) in anhydrous DMF (2.0 mL) at room temperature under nitrogen, after which the mixture was heated to 85° C. and stirred for 4 h. The cooled mixture was directly purified by flash column chromatography on silica gel, eluting with 10% concentrated ammonium hydroxide in methanol/methylene chloride (gradient from 2:98 to 10:90), to provide a yellow solid. The residue was further purified by preparative reverse phase HPLC to provide (+/−)-[2-(3-chlorobenzyl)pyrrolidin-1-yl](6,7-difluoro-3-hydroxyquinoxalin-2-yl)methanone as a light yellow solid: ¹H NMR (400 MHz, CDCl₃, ~2:1 mixture of rotamers) δ 7.72-7.63 (m, 2H, rotamers A and B), 7.38-7.21 (m, 2H, rotamers A and B), 7.10-7.03 (m, 1H, rotamers A and B), 6.90-6.79 (m, 1H, rotamers A and B), 4.63-4.56 (m, 1H, rotamers A and B), 3.89-3.82 (m, 1H, rotamer B), 3.76-3.69 (m, 1H, rotamer A), 3.56-3.47 (m, 1H, rotamers A and B), 3.33 (dd, 1H, rotamer A), 3.17 (q, 1H, rotamer B), 2.94-2.89 (m, 1H, rotamer A), 2.86-2.63 (m, 1H, rotamer B), 2.12-1.92 (m, 2H, rotamers A and B), 1.91-1.73 (m, 2H, rotamers A and B) ppm; ESI MS m/z 404 [M+H]⁺.

The following examples were prepared using General Method 1 as described above:

(+/−)-[2-(3-Chlorobenzyl)pyrrolidin-1-yl](7-fluoro-3-hydroxyquinoxalin-2-yl)methanone (1-3)

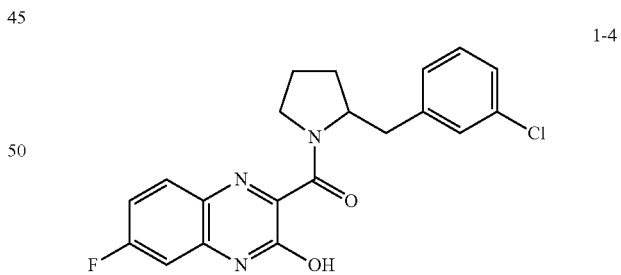

1-3

Yellow solid: ¹H NMR (400 MHz, CDCl₃, ~2:1 mixture of rotamers) δ 7.91-7.81 (m, 2H, rotamers A and B), 7.38-6.97 (m, 4H, rotamers A and B), 6.86-6.79 (m, 1H, rotamers A and B), 4.66-4.54 (m, 1H, rotamer A), 4.42 (s, 1H, rotamer B), 3.92-3.79 (m, 1H, rotamer B), 3.78-3.67 (m, 1H, rotamer B), 3.53-3.37 (m, 2H, rotamer A), 3.33 (dd, 1H, rotamer A), 2.95 (dd, 1H, rotamer A), 2.85 (dd, 1H, rotamer B), 2.65 (dd, 1H, rotamer B), 2.13-1.67 (m, 4H, rotamers A and B) ppm; ESI MS m/z 386 [M+H]⁺.

(+/−)-[2-(3-Chlorobenzyl)pyrrolidin-1-yl](6-fluoro-3-hydroxyquinoxalin-2-yl)methanone (1-4)

1-4

Yellow solid: ¹H NMR (400 MHz, CDCl₃, ~2:1 mixture of rotamers) δ 7.62-7.52 (m, 1H, rotamers A and B), 7.51-7.42 (m, 1H, rotamers A and B), 7.42-7.28 (m, 1H, rotamers A and B), 7.26-7.19 (m, 2H, rotamers A and B), 7.10-6.99 (m, 1H, rotamers A and B), 6.88-6.78 (m, 1H, rotamers A and B), 4.66-4.54 (m, 1H, rotamer A), 4.42 (s, 1H, rotamer B), 3.94-3.78 (m, 1H, rotamer B), 3.78-3.62 (m, 1H, rotamer B), 3.59-3.35 (m, 2H, rotamers A and B), 3.30 (dd, 1H, rotamer A), 3.06-2.93 (m, 1H, rotamer A), 2.86-2.57 (m, 1H, rotamer B), 2.15-1.93 (m, 2H, rotamers A and B), 1.93-1.57 (m, 1H, rotamers A and B) ppm; ESI MS m/z 386 [M+H]⁺.

31

(+/−)-[2-(3-Chlorobenzyl)pyrrolidin-1-yl](5-fluoro-3-hydroxyquinoxalin-2-yl)methanone (1-5)

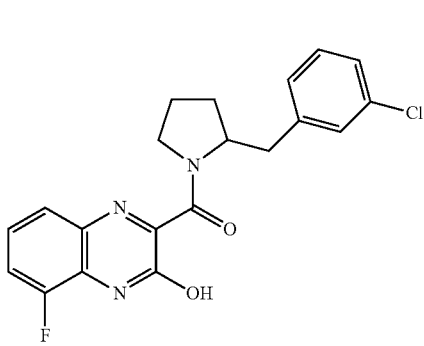

Yellow solid: $^1$H NMR (400 MHz, CD$_3$OD, ~2:1 mixture of rotamers) δ 7.69 (d, J=8.1 Hz, 1H, rotamer A), 7.64 (d, J=8.2 Hz, 1H, rotamer B), 7.54-7.43 (m, 1H, rotamers A and B), 7.43-7.30 (m, 2H, rotamers A and B and 2H, rotamer B), 7.27-7.20 (m, 1H, rotamers A and B), 7.13-7.01 (m, 1H, rotamer A), 6.86 (t, J=3.6 Hz, 1H, rotamer A), 4.54-4.41 (m, 1H, rotamer A), 4.31 (d, J=6.1 Hz, 1H, rotamer B), 3.75 (dt, J=12.4, 8.3 Hz, 1H, rotamer B), 3.65-3.55 (m, 1H, rotamer B), 3.50-3.33 (m, 3H, rotamer A), 3.24 (dd, J=13.3, 3.5 Hz, 1H, rotamer A), 3.03-2.90 (m, 1H, rotamer B), 2.88-2.66 (m, 1H, rotamer B), 2.19-1.66 (m, 4H, rotamers A and B) ppm; ESI MS m/z 386 [M+H]$^+$.

(+/−)-[2-(3-Chlorobenzyl)pyrrolidin-1-yl](5,7-difluoro-3-hydroxyquinoxalin-2-yl)methanone (1-6)

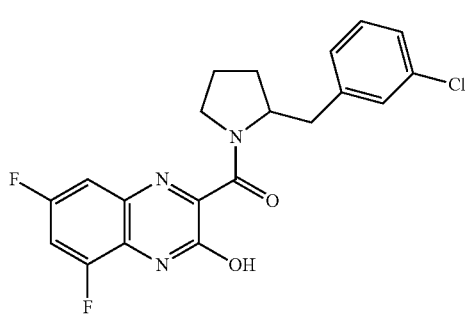

Brown solid: $^1$H NMR (400 MHz, DMSO-d$_6$, ~2:1 mixture of rotamers) δ 7.75-7.67 (m, 1H, rotamers A and B), 7.61-7.52 (m, 1H, rotamers A and B), 7.41 (s, 1H, rotamers A and B), 7.39-7.29 (m, 2H, rotamers A and B), 7.20-7.16 (m, 1H, rotamer A), 6.94 (s, 1H, rotamer B), 4.36-4.31 (m, 1H, rotamer A), 4.11-4.05 (m, 1H, rotamer B), 3.62-3.55 (m, 1H, rotamer B), 3.46-3.40 (m, 1H, rotamer B), 3.35-3.28 (m, 1H, rotamer A), 3.25-3.19 (m, 1H, rotamer A), 3.14 (d, J=12.8 Hz, 1H, rotamer A), 2.89-2.83 (m, 1H, rotamer A), 2.79-2.64 (m, 2H, rotamer A), 1.92-1.82 (m, 2H, rotamers A and B), 1.75-1.65 (m, 2H, rotamers A and B) ppm; ESI MS m/z 402 [M−H]$^−$.

32

(+/−)-[2-(3-Chlorobenzyl)pyrrolidin-1-yl](5,6-difluoro-3-hydroxyquinoxalin-2-yl)methanone (1-7)

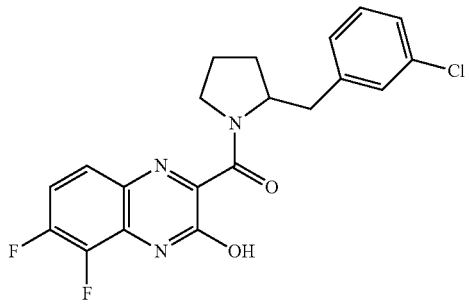

Yellow solid: $^1$H NMR (400 MHz, CD$_3$OD, ~2:1 mixture of rotamers) δ 7.72-7.68 (m, 1H, rotamer A), 7.66-7.62 (m, 1H, rotamer B), 7.40 (s, rotamer A), 7.34-7.23 (m, 1H, rotamers A and B and 4H, rotamer A), 7.10-7.07 (m, 2H, rotamer B), 6.90-6.86 (m, 2H, rotamer B), 4.51-4.49 (m, 1H, rotamer A), 4.35 (q, J=6.1 Hz, 1H, rotamer B), 3.78-3.71 (m, 1H, rotamer B), 3.63-3.57 (m, 1H, rotamer B), 3.48-3.40 (m, 1H, rotamer A), 3.37-3.29 (m, 1H, rotamer A), 3.23 (dd, J=3.9, 13.4 Hz, 1H, rotamer A), 2.95 (dd, J=8.6, 12.8 Hz, 1H, rotamer A), 2.84-2.70 (m, 2H, rotamer B), 2.10-1.73 (m, 4H, rotamers A and B) ppm; ESI MS m/z 404 [M+H]$^+$.

(+/−)-(8-Chloro-3-hydroxyquinoxalin-2-yl)[2-(3-chlorobenzyl)pyrrolidin-1-yl]methanone (1-8)

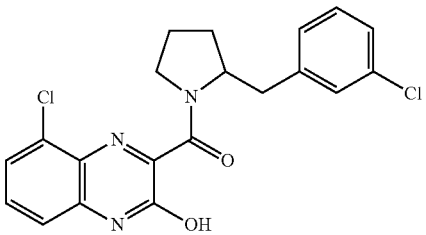

Yellow solid: $^1$H NMR (400 MHz, CD$_3$OD, ~2:1 mixture of rotamers) δ 7.60-7.54 (m, 1H, rotamers A and B), 7.53-7.46 (m, 1H, rotamers A and B), 7.41-7.24 (m, 3H, rotamers A and B), 7.09-7.04 (m, 1H, rotamers A and B), 6.91-6.86 (m, 1H, rotamers A and B), 4.55-4.45 (m, 1H, rotamer A), 4.45-4.35 (m, 1H, rotamer B), 3.80-3.69 (m, 1H, rotamer B), 3.65-3.55 (m, 1H, rotamer B), 3.51-3.35 (m, 2H, rotamer A), 3.25 (dd, 1H, rotamer A), 3.02-2.89 (m, 1H, rotamer A), 2.82-2.72 (m, 2H, rotamer B), 2.11-1.70 (m, 4H, rotamers A and B) ppm; ESI MS m/z 402 [M+H]$^+$.

33

(+/−)-(7-Chloro-3-hydroxyquinoxalin-2-yl)[2-(3-chlorobenzyl)pyrrolidin-1-yl]methanone (1-9)

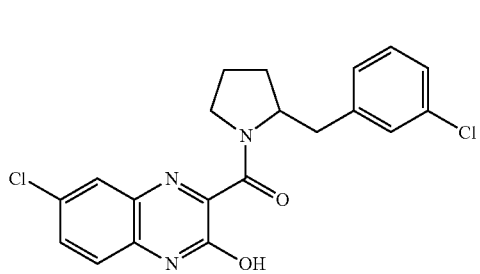

1-9

Yellow solid: $^1$H NMR (400 MHz, CD$_3$OD, ~2:1 mixture of rotamers) δ 7.90-7.85 (m, 1H, rotamer A), 7.82 (s, 1H, rotamer B), 7.66-7.60 (m, 1H, rotamers A and B), 7.40-7.18 (m, 3H, rotamers A and B), 7.09-7.05 (m, 1H, rotamers A and B), 6.89-6.84 (m, 1H, rotamers A and B), 4.52-4.44 (m, 1H, rotamer A), 4.33-4.26 (m, 1H, rotamer B), 3.80-3.70 (m, 1H, rotamer B), 3.66-3.54 (m, 1H, rotamer B), 3.50-3.33 (m, 2H, rotamer A), 3.24 (dd, 1H, rotamer A), 2.98-2.82 (m, 1H, rotamer A), 2.82-2.69 (m, 2H, rotamer B), 2.13-1.70 (m, 4H, rotamers A and B) ppm; ESI MS m/z 402 [M+H]$^+$.

(+/−)-(6-Chloro-3-hydroxyquinoxalin-2-yl)[2-(3-chlorobenzyl)pyrrolidin-1-yl]methanone (1-10)

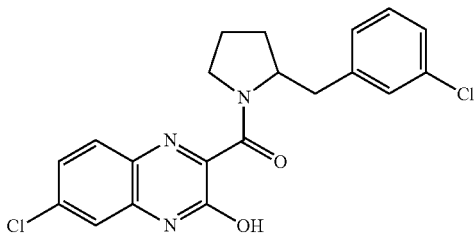

1-10

Yellow solid: $^1$H NMR (400 MHz, CD$_3$OD, ~2:1 mixture of rotamers) δ 7.83 (dd, 1H, rotamer A), 7.78 (dd, 1H, rotamer B), 7.43-7.36 (m, 2H, rotamers A and B), 7.33-7.27 (m, 1H, rotamers A and B), 7.27-7.21 (m, 1H, rotamers A and B), 7.11-7.03 (m, 1H, rotamers A and B), 6.89-6.82 (m, 1H, rotamers A and B), 4.52-4.44 (m, 1H, rotamer A), 4.33-4.25 (m, 1H, rotamer B), 3.79-3.69 (m, 1H, rotamer B), 3.64-3.56 (m, 1H, rotamer B), 3.50-3.33 (m, 2H, rotamer A), 3.23 (dd, 1H. rotamer A), 2.98-2.89 (m, 1H, rotamer A), 2.85-2.77 (m, 1H, rotamer B), 2.76-2.67 (m, 1H, rotamer B), 2.11-1.70 (m, 4H, rotamers A and B) ppm; ESI MS m/z 402 [M+H]$^+$.

34

(+/−)-(5-Chloro-3-hydroxyquinoxalin-2-yl)[2-(3-chlorobenzyl)pyrrolidin-1-yl]methanone (1-11)

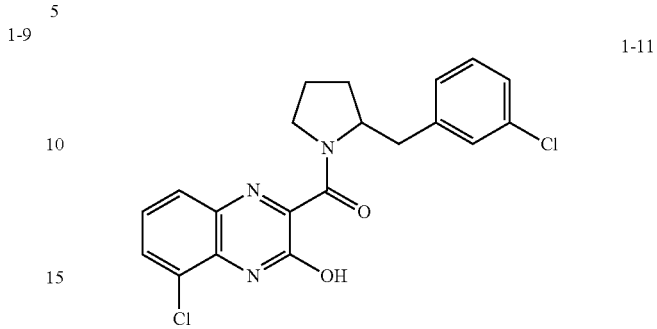

1-11

Yellow solid: $^1$H NMR (400 MHz, CD$_3$OD, ~2:1 mixture of rotamers) δ 7.83 (dd, 1H, rotamer A), 7.80-7.78 (dd, 1H, rotamer B), 7.78-7.70 (m, 1H, rotamers A and B), 7.43-7.36 (m, 1H, rotamers A and B), 7.32-7.28 (m, 1H, rotamers A and B), 7.28-7.22 (m, 1H, rotamers A and B), 7.09-7.04 (m, 1H, rotamers A and B), 6.89-6.83 (m, 1H, rotamers A and B), 4.57-4.44 (m, 1H, rotamer A), 4.39-4.26 (m, 1H, rotamer B), 3.82-3.69 (m, 1H, rotamer B), 3.67-3.56 (m, 1H, rotamer B), 3.51-3.33 (m, 2H, rotamer A), 3.24 (dd, 1H, rotamer A), 2.95 (dd, 1H, rotamer A), 2.89-2.78 (m, 1H, rotamer B), 2.73 (dd, 1H, rotamer B), 2.16-1.67 (m, 4H, rotamers A and B) ppm; ESI MS m/z 402 [M+H]$^+$.

(+/−)-(5-Chloro-3-hydroxyquinoxalin-2-yl)[2-(3,4-dimethylbenzyl)pyrrolidin-1-yl]methanone (1-12)

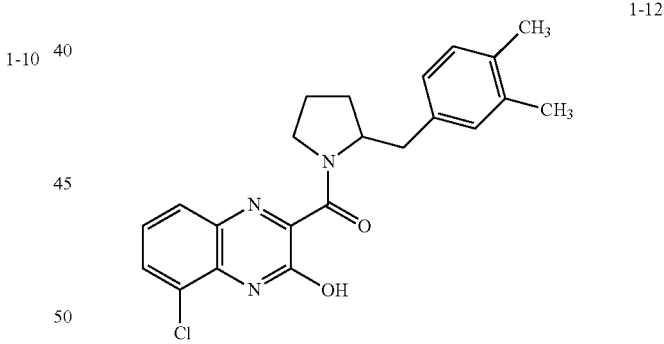

1-12

Red solid: $^1$H NMR (400 MHz, CDCl$_3$, ~2:1 mixture of rotamers) δ 7.83 (d, J=8.0 Hz, 1H, rotamer A), 7.79 (d, J=8.3 Hz, 1H, rotamer B), 7.65-7.61 (m, 1H, rotamers A and B), 7.32 (t, J=8.6 Hz, 1H, rotamers A and B), 7.14 (s, 1H, rotamer A), 7.07 (s, 2H, rotamer A), 6.84 (d, J=7.7 Hz, 1H, rotamer B), 6.60 (d, J=8.0 Hz, 1H, rotamer B), 6.54 (s, 1H, rotamer B), 4.59-4.53 (m, 1H, rotamer A), 4.37 (s, 1H, rotamer B), 3.86-3.78 (m, 1H, rotamer B), 3.77-3.70 (m, 1H, rotamer B), 3.42 (t, J=5.8 Hz, 2H, rotamer A), 3.33 (dd, J=3.1, 12.9 Hz, 1H, rotamer A), 2.82-2.75 (m, 1H, rotamers A and B), 2.62-2.56 (m, 1H, rotamer B), 2.27 (s, 3H, rotamer A), 2.24 (s, 3H, rotamer A), 2.11 (s, 3H, rotamer B), 2.05-1.77 (m, 4H, rotamers A and B), 1.95 (s, 3H, rotamer B) ppm; ESI MS m/z 394 [M−H]$^−$.

35

(+/−)-[2-(3-Chlorobenzyl)pyrrolidin-1-yl](6,7-dichloro-3-hydroxyquinoxalin-2-yl)methanone (1-13)

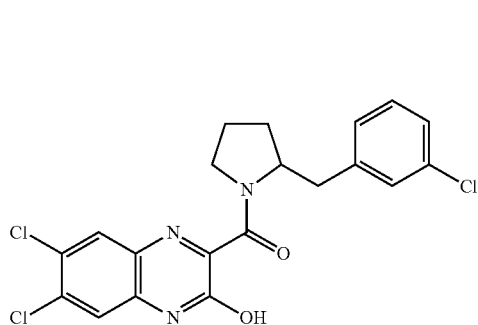

1-13

Yellow solid: ¹H NMR (400 MHz, CD₃OD, ~2:1 mixture of rotamers) δ 8.01 (s, 1H, rotamer A), 7.95 (s, 1H, rotamer B), 7.52 (s, 1H, rotamer A), 7.50 (s, 1H, rotamer B), 7.38-7.21 (m, 2H, rotamers A and B), 7.13-7.04 (m, 1H, rotamers A and B), 6.91-6.84 (m, 1H, rotamers A and B), 4.52-4.42 (m, 1H, rotamer A), 4.39-4.29 (m, 1H, rotamer B), 3.81-3.70 (m, 1H, rotamer B), 3.66-3.56 (m, 1H, rotamer B), 3.51-3.34 (m, 2H, rotamer A), 3.23 (dd, 1H, rotamer A), 2.99-2.88 (m, 1H, rotamer A), 2.83-2.66 (m, 2H, rotamer B), 2.13-1.71 (m, 4H, rotamers A and B) ppm; ESI MS m/z 434 [M−H]⁻.

(+/−)-(6,7-Dichloro-3-hydroxyquinoxalin-2-yl)[2-(3-fluorobenzyl)pyrrolidin-1-yl]methanone (1-14)

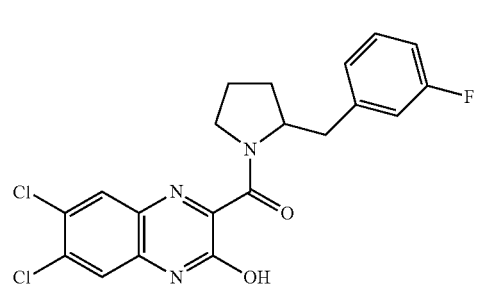

1-14

Brown solid: ¹H NMR (400 MHz, CDCl₃, ~2:1 mixture of rotamers) δ 7.94 (s, 1H, rotamer A), 7.92 (s, 1H, rotamer B), 7.60 (s, 1H, rotamer B), 7.58 (s, 1H, rotamer A), 7.29-7.23 (m, 2H, rotamer A), 7.12-7.03 (m, 1H, rotamers A and B), 6.96-6.90 (m, 1H, rotamer A), 6.83-6.77 (m, 1H, rotamer B), 6.68-6.63 (m, 2H, rotamer B), 4.63-4.56 (m, 1H, rotamer A), 4.46-4.40 (m, 1H, rotamer B), 3.89-3.81 (m, 1H, rotamer B), 3.73-3.67 (m, 1H, rotamer B), 3.48-3.36 (m, 1H, rotamer A), 3.30 (d, J=13.7 Hz, rotamer A), 3.00-2.89 (m, 2H, rotamer A), 2.85-2.78 (m, 1H, rotamer B), 2.71-2.64 (m, 1H, rotamer B), 2.08-1.67 (m, 4H, rotamers A and B) ppm; ESI MS m/z 420 [M+H]⁺.

36

(+/−)-(6,7-Dichloro-3-hydroxyquinoxalin-2-yl)[2-(3,4-dimethylbenzyl)pyrrolidin-1-yl]methanone (1-15)

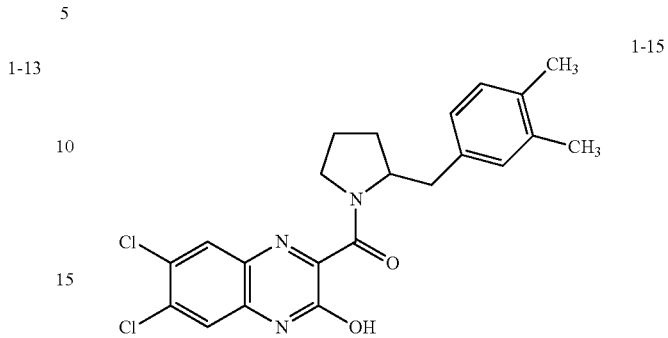

1-15

Brown solid: ¹H NMR (400 MHz, CDCl₃, ~2:1 mixture of rotamers) δ 7.94 (s, 1H, rotamer A), 7.91 (s, 1H, rotamer B), 7.60 (s, 1H, rotamer B), 2.58 (s, 1H, rotamer A), 7.10 (s, 1H, rotamer B), 7.05 (s, 1H, rotamer A), 6.86-6.80 (m, 1H, rotamers A and B), 6.62-6.56 (m, 1H, rotamers A and B), 4.60-4.54 (m, 1H, rotamer A), 4.48-4.41 (m, 1H, rotamer B), 3.87-3.71 (m, 2H, rotamer B), 3.49-3.41 (m, 1H, rotamer A), 3.31 (d, J=13.4 Hz, 1H, rotamer A), 2.89 (s, 1H, rotamer B), 2.80-2.72 (m, 2H, rotamer A), 2.63-2.56 (m, 1H, rotamer B), 2.26 (s, 3H, rotamer A), 2.23 (s, 3H, rotamer A), 2.10 (s, 3H, rotamer B), 1.98 (s, 3H, rotamer B), 2.04-1.77 (m, 4H, rotamers A and B) ppm; ESI MS m/z 428 [M−H]⁺.

(+/−)-[(6,7-Dichloro-3-hydroxyquinoxalin-2-yl)(2-(3,4-dichlorobenzyl)pyrrolidin-1-yl]methanone (1-16)

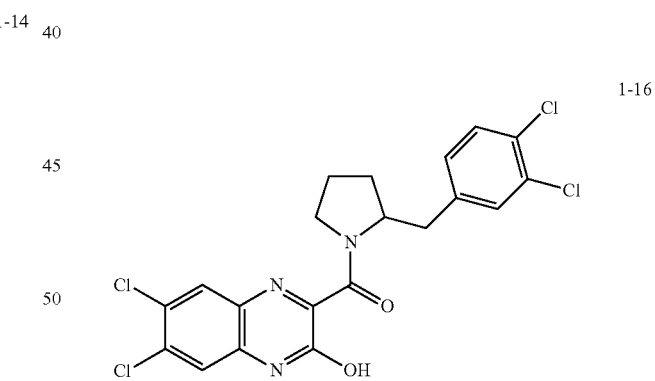

1-16

Brown solid: ¹H NMR (400 MHz, DMSO-d₆, ~2:1 mixture of rotamers) δ 12.92 (s, 1H, rotamers A and B), 8.13 (s, 1H, rotamer A), 7.94 (s, 1H, rotamer B), 7.62-7.58 (m, 1H, rotamers A and B), 7.51-7.49 (m, 1H, rotamer A), 7.38-7.33 (m, 1H, rotamer A), 7.21 (s, 1H, rotamer B), 6.99 (d, J=8.3 Hz, 1H, rotamer B), 4.36-4.30 (m, 1H, rotamer A), 4.15-4.10 (m, 1H, rotamer B), 3.66-3.59 (m, 1H, rotamer B), 3.47-3.39 (m, 1H, rotamer B), 3.34-3.18 (m, 2H, rotamer A), 3.09 (d, J=13.6 Hz, 1H, rotamer A), 2.92-2.87 (m, 1H, rotamer A), 2.78-2.72 (m, 1H, rotamer B), 2.69-2.63 (m, 1H, rotamer B), 1.93-1.83 (m, 2H, rotamers A and B), 1.75-1.64 (m, 2H, rotamers A and B) ppm; ESI MS m/z 468 [M−H]⁻.

37

(+/−)-(6,7-Dichloro-3-hydroxyquinoxalin-2-yl)[2-(4-fluorobenzyl)pyrrolidin-1-yl]methanone (1-17)

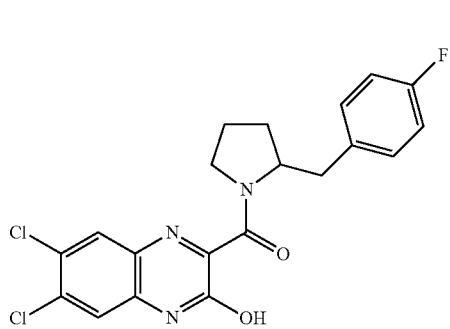

1-17

Brown solid: ¹H NMR (400 MHz, DMSO-d₆, ~2:1 mixture of rotamers) δ 12.93 (m, 1H, rotamers A and B), 8.15 (s, 1H, rotamer A), 8.07 (s, 1H, rotamer B), 7.53 (s, 1H, rotamer B), 7.51 (s, 1H, rotamer A), 7.38-7.34 (m, 1H, rotamers A and B), 7.15 (t, J=8.7 Hz, 2H, rotamers A and B), 7.01-6.96 (m, 1H, rotamers A and B), 4.33-4.27 (m, 1H, rotamer A), 4.09-4.04 (m, 1H, rotamer B), 3.61-3.54 (m, 1H, rotamer B), 3.42-3.36 (m, 1H, rotamer B), 3.34-3.27 (m, 1H, rotamer A), 3.24-3.18 (m, 1H, rotamer A), 3.11 (d, J=12.5 Hz, 1H, rotamer A), 2.85-2.79 (m, 1H, rotamers A and B), 2.76-2.61 (m, 1H, rotamer B), 1.87-1.78 (m, 2H, rotamers A and B), 1.72-1.63 (m, 2H, rotamers A and B) ppm; ESI MS m/z 418 [M−H]⁻.

(+/−)-[2-(3-Chlorobenzyl)pyrrolidin-1-yl](3-hydroxy-7-iodoquinoxalin-2-yl)methanone (1-18)

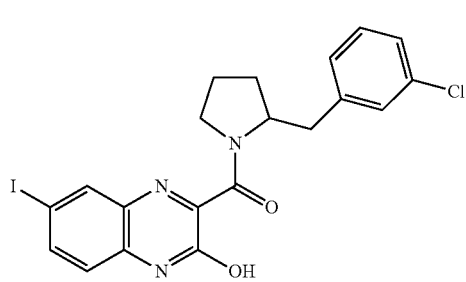

1-18

Yellow solid: ¹H NMR (400 MHz, CDCl₃, ~2:1 mixture of rotamers) δ 12.32 (s, 1H, rotamers A and B), 8.23 (d, J=14.2 Hz, 1H, rotamers A and B), 7.81 (s, 1H, rotamers A and B), 7.26-7.11 (m, 3H, rotamers A and B), 7.10-6.93 (m, 1H, rotamers A and B), 6.93 (s, 1H, rotamer A), 6.79-6.75 (m, 1H, rotamer B), 4.59 (s, 1H, rotamer A), 4.43 (s, 1H, rotamer B), 3.95-3.77 (m, 1H, rotamer B), 3.77-3.64 (m, 1H, rotamer B), 3.51-3.35 (m, 2H, rotamer A), 3.30 (d, J=12.7 Hz, 1H, rotamer A), 3.05-2.86 (m, 1H, rotamer A), 2.80 (dd, J=14.7, 4.7 Hz, 1H, rotamer B), 2.73-2.59 (m, 1H, rotamer B), 2.20-1.43 (m, 4H, rotamers A and B) ppm; ESI MS m/z 494 [M+H]⁺.

38

(+/−)-[2-(3-Chlorobenzyl)pyrrolidin-1-yl](3-hydroxy-6-iodoquinoxalin-2-yl)methanone (1-19)

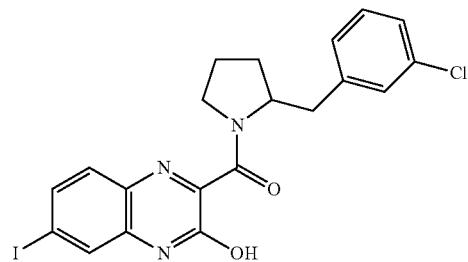

1-19

Yellow solid: ¹H NMR (400 MHz, CDCl₃, ~2:1 mixture of rotamers) δ 11.64 (s, 1H, rotamers A and B), 7.81-7.72 (m, 1H, rotamers A and B), 7.72-7.63 (m, 1H, rotamers A and B), 7.63-7.51 (m, 1H, rotamers A and B), 7.39 (s, H, rotamer B), 7.32-7.16 (m, 2H, rotamers A and B), 7.12-7.01 (m, 1H, rotamers A and B), 6.91-6.74 (m, 1H, rotamer A), 4.69-4.55 (m, 1H, rotamer A), 4.41 (s, 1H, rotamer B), 3.96-3.65 (m, 2H, rotamer B), 3.56-3.38 (m, 1H, rotamer A), 3.33 (dd, J=13.4, 3.3 Hz, 1H, rotamer A), 3.06-2.82 (m, 1H, rotamer A), 2.72-2.61 (m, 2H, rotamer B), 2.15-1.65 (m, 4H, rotamers A and B) ppm; ESI MS m/z 494 [M+H]⁺.

(+/−)-[2-(3-Chlorobenzyl)pyrrolidin-1-yl][3-hydroxy-7-(trifluoromethoxy)quinoxalin-2-yl]methanone (1-20)

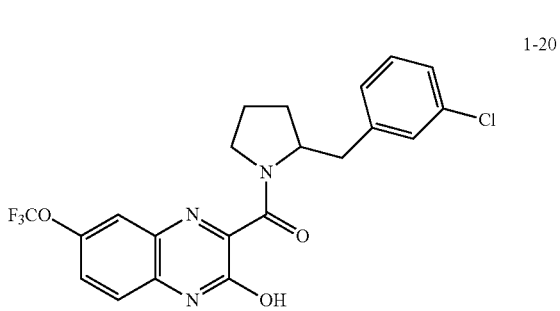

1-20

Yellow solid: ¹H NMR (400 MHz, CDCl₃, ~2:1 mixture of rotamers) δ 12.39 (s, 1H, rotamers A and B), 7.79 (s, 1H, rotamer A), 7.94 (s, 1H, rotamer B), 7.52-7.35 (m, 3H, rotamers A and B), 7.25-7.19 (m, 2H, rotamers A and B), 7.14-6.94 (m, 1H, rotamer A), 6.76-6.74 (m, 1H, rotamer B), 4.54 (s, 1H, rotamer A), 4.46 (s, 1H, rotamer B), 3.93-3.78 (m, 1H, rotamer B), 3.78-3.64 (m, 1H, rotamer B), 3.56-3.36 (m, 2H, rotamer A), 3.30 (dd, J=13.3, 3.3 Hz, 1H, rotamer A), 3.04-2.87 (m, 1H, rotamer A), 2.87-2.75 (m, 1H, rotamer B), 2.67 (dd, J=13.8, 7.7 Hz, 1H, rotamer B), 2.21-1.64 (m, 4H, rotamers A and B) ppm; ESI MS m/z 450 [M−H]⁻.

39

(+/−)-[2-(3-Chlorobenzyl)pyrrolidin-1-yl][3-hydroxy-6-(trifluoromethoxy)quinoxalin-2-yl]methanone (1-21)

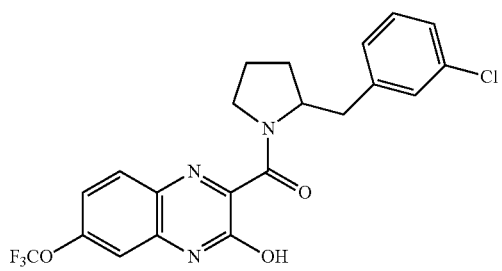

1-21

Yellow solid: ¹H NMR (400 MHz, CDCl₃, ~2:1 mixture of rotamers) δ 12.05 (s, 1H, rotamers A and B), 7.92 (d, J=8.8 Hz, 1H, rotamer A), 7.89 (d, J=8.8 Hz, 1H, rotamer B), 7.37 (s, 1H, rotamer A), 7.25-7.16 (m, 4H, rotamers A and B plus 1H, rotamer A), 7.11-6.96 (m, 1H, rotamer B), 6.90-6.75 (m, 1H, rotamer B), 4.68-4.53 (m, 1H, rotamer A), 4.44 (s, 1H, rotamer B), 3.93-3.80 (m, 1H, rotamer B), 3.78-3.65 (m, 1H, rotamer B), 3.52-3.37 (m, 2H, rotamer A), 3.33 (dd, J=13.3, 3.3 Hz, 1H, rotamer A), 2.99-2.78 (m, 1H, rotamers A and B), 2.66 (dd, J=13.7, 8.0 Hz, 1H, rotamer B), 2.15-1.66 (m, 4H, rotamers A and B) ppm; ESI MS m/z 450 [M−H]⁻.

(+/−)-[2-(3-Chlorobenzyl)pyrrolidin-1-yl][3-hydroxy-7-(trifluoromethylthio]quinoxalin-2-yl)methanone (1-22)

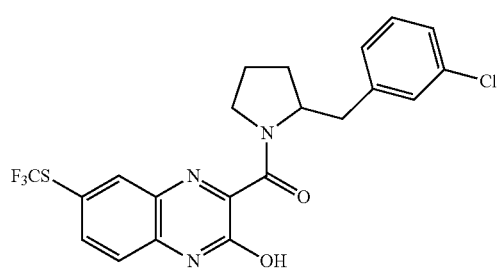

1-22

Yellow solid: ¹H NMR (400 MHz, CD₃OD, ~2:1 mixture of rotamers) δ 8.21 (d, J=1.9 Hz, 1H, rotamer A), 8.14 (d, J=1.9 Hz, 1H, rotamer B), 7.88 (dd, J=8.6, 2.1 Hz, 1H, rotamers A and B), 7.49-7.38 (m, 2H, rotamers A and B), 7.34-7.22 (m, 1H, rotamers A and B and 2H, rotamer B), 7.04 (dd, J=3.4, 1.9 Hz, 1H, rotamer A), 6.93-6.82 (m, 1H, rotamer A), 4.57-4.41 (m, 1H, rotamer A), 4.35 (d, J=6.4 Hz, 1H, rotamer B), 3.76 (dt, J=12.4, 8.4 Hz, 1H, rotamer B), 3.62 (dd, J=16.0, 8.2 Hz, 1H, rotamer B), 3.53-3.32 (m, 2H, rotamer A), 3.23 (dd, J=13.3, 3.5 Hz, 1H, rotamer A), 3.05-2.88 (m, 1H, rotamer A), 2.83-2.74 (m, 2H, rotamer B), 2.14-1.70 (m, 4H, rotamers A and B) ppm; ESI MS m/z 468 [M+H]⁺.

40

(+/−)-[2-(3-Chlorobenzyl)pyrrolidin-1-yl][3-hydroxy-6-(trifluoromethylthio]quinoxalin-2-yl)methanone (1-23)

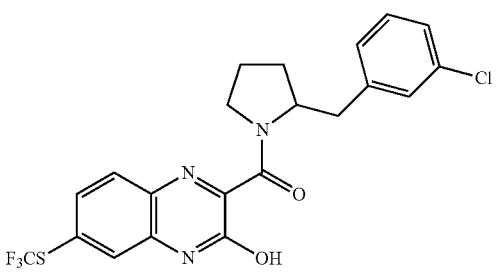

1-23

Light yellow solid: ¹H NMR (400 MHz, CD₃OD, ~2:1 mixture of rotamers) δ 7.95 (d, J=8.4 Hz, 1H, rotamer A), 7.89 (d, J=8.4 Hz, 1H, rotamer B), 7.73-7.61 (m, 2H, rotamers A and B), 7.40 (s, 1H, rotamer A), 7.37-7.19 (m, 2H, rotamers A and B), 7.11-6.99 (m, 1H, rotamer A), 6.92-6.80 (m, 2H, rotamer B), 4.59-4.43 (m, 1H, rotamer A), 4.40-4.28 (m, 1H, rotamer B), 3.84-3.70 (m, 1H, rotamer B), 3.69-3.55 (m, 1H, rotamer B), 3.51-3.34 (m, 2H, rotamer A), 3.24 (dd, J=13.3, 3.5 Hz, 1H, rotamer A), 3.00-2.84 (m, 1H, rotamer A), 2.86-2.69 (m, 2H, rotamer B), 2.17-1.69 (m, 4H, rotamers A and B) ppm; ESI MS m/z 468 [M+H]⁺.

(+/−)-[2-(3-Chlorobenzyl)pyrrolidin-1-yl][3-hydroxy-7-(trifluoromethylsulfonyl)quinoxalin-2-yl]methanone (1-24)

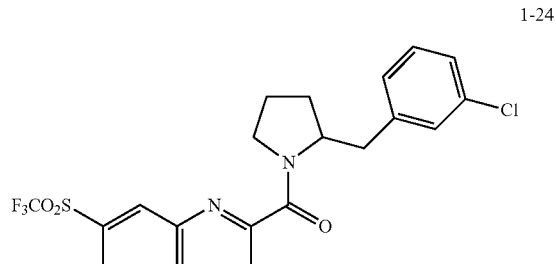

1-24

Red-brown solid: ¹H NMR (400 MHz, CDCl₃, ~2:1 mixture of rotamers) δ 8.55 (d, J=1.7 Hz, 1H, rotamer A), 8.48 (d, J=1.7 Hz, 1H, rotamer B), 8.08 (d, J=8.7 Hz, 1H, rotamers A and B), 7.68 (dd, J=8.7, 3.2 Hz, 1H, rotamers A and B), 7.33-7.11 (m, 2H, rotamers A and B and 2H, rotamer B), 7.07-6.88 (m, 1H, rotamer A), 6.84-6.71 (m, 1H, rotamer A), 4.65-4.45 (m, 1H, rotamers A and B), 3.90-3.64 (m, 2H, rotamer B), 3.53-3.34 (m, 2H, rotamer A), 3.26 (dd, J=13.3, 3.3 Hz, 1H, rotamer A), 2.90 (dd, J=13.3, 8.6 Hz, 1H, rotamer A), 2.84-2.54 (m, 2H, rotamer B), 2.15-1.70 (m, 4H, rotamers A and B) ppm; ESI MS m/z 500 [M+H]⁺.

41

(+/−)-[2-(3-Chlorobenzyl)pyrrolidin-1-yl][3-hydroxy-6-(trifluoromethylsulfonyl)quinoxalin-2-yl]methanone (1-25)

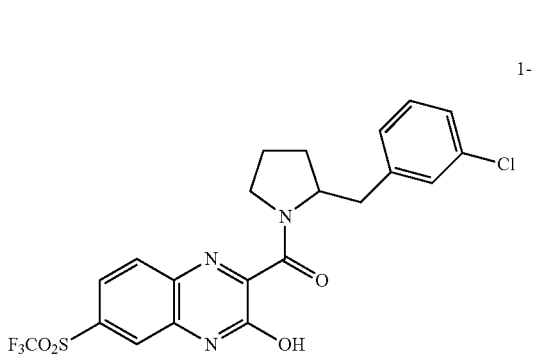

Brown solid: $^1$H NMR (400 MHz, CDCl$_3$, ~2:1 mixture of rotamers) δ 8.20-8.00 (m, 2H, rotamers A and B), 7.90 (t, J=7.0 Hz, 1H, rotamers A and B), 7.33-7.12 (m, 2H, rotamers A and B and 2H, rotamer B), 7.07-6.96 (m, 1H, rotamer A), 6.86-6.72 (m, 1H, rotamer A), 4.68-4.54 (m, 1H, rotamer A), 4.48 (s, 1H, rotamer B), 3.93-3.68 (m, 2H, rotamer B), 3.52-3.34 (m, 2H, rotamer A), 3.29 (dd, J=13.4, 3.3 Hz, 1H, rotamer A), 3.01-2.87 (m, 1H, rotamer A), 2.87-2.61 (m, 2H, rotamer B), 2.24-1.66 (m, 4H, rotamers A and B) ppm; ESI MS m/z 500 [M+H]$^+$.

(+/−)-[2-(3-Chlorobenzyl)pyrrolidin-1-yl][3-hydroxy-6-(methylsulfonyl)quinoxalin-2-yl]methanone (1-26)

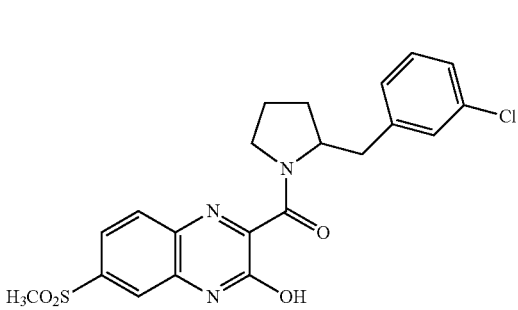

Brown solid: $^1$H NMR (400 MHz, CDCl$_3$, ~2:1 mixture of rotamers) δ 8.06-8.03 (m, 2H, rotamers A and B), 7.86 (t, J=8.2 Hz, 1H, rotamers A and B), 7.36 (s, 1H, rotamer A), 7.28-7.21 (m, 1H, rotamers A and B and 1H, rotamer A), 7.09-7.03 (m, 1H, rotamers A and B), 6.82-6.79 (m, 2H, rotamer B), 4.64-4.58 (m, 1H, rotamer A), 4.44-4.39 (m, 1H, rotamer B), 3.92-3.83 (m, 1H, rotamer B), 3.79-3.72 (m, 1H, rotamer B), 3.48-3.38 (m, 1H, rotamer A), 3.31 (d, J=13.6 Hz, 1H, rotamer A), 3.12 (s, 3H, rotamer A), 2.83 (s, 3H, rotamer B), 2.97-2.86 (m, 2H, rotamer A), 2.84-2.77 (m, 1H, rotamer B), 2.71-2.63 (m, 1H, rotamer B), 2.09-1.94 (m, 2H, rotamers A and B), 1.88-1.71 (m, 2H, rotamers A and B) ppm; ESI MS m/z 444 [M−H]$^−$.

42

(+/−)-[2-(3-Chlorobenzyl)pyrrolidin-1-yl](3-hydroxy-7-methoxyquinoxalin-2-yl)methanone (1-27)

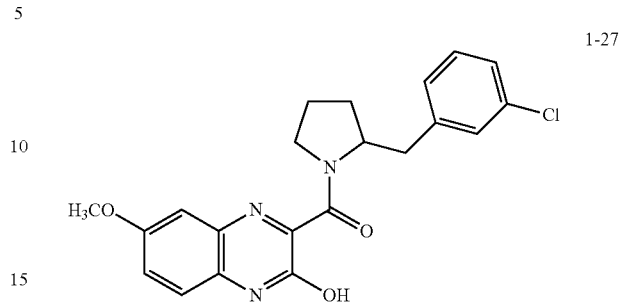

Brown solid: $^1$H NMR (400 MHz, CD$_3$OD, ~2:1 mixture of rotamers) δ 7.41 (s, 1H, rotamer A), 7.36 (s, 2H, rotamer B), 7.34-7.19 (m, 3H, rotamers A and B and 2H, rotamer A), 7.12-7.01 (m, 2H, rotamer B), 6.84 (t, J=3.8 Hz, 1H, rotamer A), 4.53-4.42 (m, 1H, rotamer A), 4.24 (dd, J=12.8, 6.2 Hz, 1H, rotamer B), 3.89 (s, 3H, rotamers A and B), 3.80-3.68 (m, 1H, rotamer B), 3.68-3.55 (m, 1H, rotamer B), 3.49-3.33 (m, 2H, rotamer A), 3.25 (dd, J=13.3, 3.5 Hz, 1H, rotamer A), 2.93 (dd, J=13.2, 8.6 Hz, 1H, rotamer A), 2.82 (dd, J=13.7, 5.2 Hz, 1H, rotamer B), 2.71 (dd, J=13.7, 8.0 Hz, 1H, rotamer B), 2.11-1.70 (m, 4H, rotamers A and B) ppm; ESI MS m/z 396 [M−H]$^−$.

(+/−)-[2-(3-Chlorobenzyl)pyrrolidin-1-yl](3-hydroxy-6-methoxyquinoxalin-2-yl)methanone (1-28)

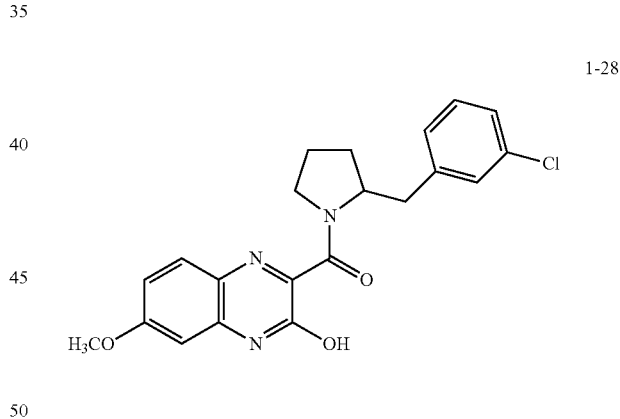

Light yellow solid: $^1$H NMR (400 MHz, CD$_3$OD, ~2:1 mixture of rotamers) δ 7.76 (d, J=9.0 Hz, 1H, rotamer A), 7.72 (d, J=9.0 Hz, 1H, rotamer B), 7.40 (s, 1H, rotamer A), 7.32-7.28 (m, 1H, rotamers A and B), 7.28-7.20 (m, 1H, rotamer B), 7.11-7.05 (m, 1H, rotamers A and B), 7.05-6.97 (m, 1H, rotamers A and B), 6.88-6.78 (m, 2H, rotamers A and B), 4.47 (td, J=8.2, 3.8 Hz, 1H, rotamer A), 4.33-4.19 (m, 1H, rotamer B), 3.92 (s, 3H, rotamers A and B), 3.78-3.65 (m, 1H, rotamer B), 3.66-3.54 (m, 1H, rotamer B), 3.49-3.33 (m, 2H, rotamer A), 3.25 (dd, J=13.2, 3.5 Hz, 1H, rotamer A), 2.92 (dd, J=13.3, 8.7 Hz, 1H, rotamer A), 2.81 (dd, J=13.6, 5.2 Hz, 1H, rotamer B), 2.70 (dd, J=13.7, 8.0 Hz, 1H, rotamer B), 2.11-1.68 (m, 4H, rotamers A and B) ppm; ESI MS m/z 396 [M−H]$^−$.

(+/−)-[2-(3,4-Dimethylbenzyl)pyrrolidin-1-yl][3-hydroxy-6-(trifluoromethyl)quinoxalin-2-yl]methanone (1-29)

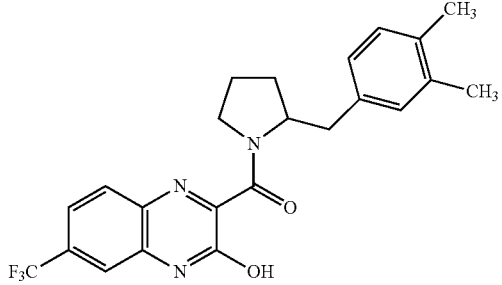

Brown solid: ¹H NMR (400 MHz, CDCl₃, ~2:1 mixture of rotamers) δ 8.00-7.94 (m, 1H, rotamers A and B), 7.68-7.66 (m, 1H, rotamers A and B), 7.61-7.57 (m, 1H, rotamers A and B), 7.13 (s, 1H, rotamer A), 7.06 (s, 1H, rotamers A and B), 6.81 (d, J=7.6 Hz, 1H, rotamer A), 6.60 (d, J=8.2 Hz, 1H, rotamer B), 6.53 (s, 1H, rotamer B), 4.63-4.57 (m, 1H, rotamer A), 4.44-4.38 (m, 1H, rotamer B), 3.89-3.81 (m, 1H, rotamer B), 3.79-3.72 (m, 1H, rotamer B), 3.48-3.13 (m, 1H, rotamer A), 3.35 (d, J=13.1 Hz, 1H, rotamer A), 2.89 (s, 1H, rotamer B), 2.81-2.75 (m, 2H, rotamer A), 2.63-2.57 (m, 1H, rotamer B), 2.26 (s, 3H, rotamer A), 2.21 (s, 3H, rotamer A), 2.07 (s, 3H, rotamer B), 2.05-1.94 (m, 2H, rotamers A and B), 1.92 (s, 3H, rotamer B), 1.91-1.78 (m, 2H, rotamers A and B) ppm; ESI MS m/z 428 [M−H]⁻.

(+/−)-[2-(3-Chlorobenzyl)pyrrolidin-1-yl][3-hydroxy-5-(trifluoromethyl)quinoxalin-2-yl]methanone (1-30)

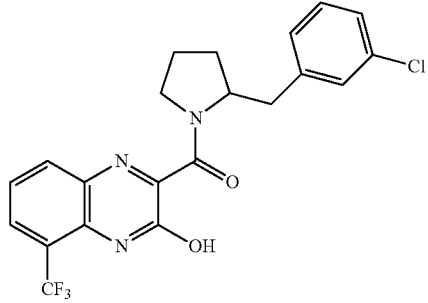

Yellow solid: ¹H NMR (400 MHz, CD₃OD, ~2:1 mixture of rotamers) δ 8.13 (d, J=7.8 Hz, 1H, rotamer A), 8.05 (d, J=7.8 Hz, 1H, rotamer B), 8.00 (d, J=7.6 Hz, 1H, rotamers A and B), 7.55 (t, J=7.8 Hz, 1H, rotamers A and B), 7.41 (s, 1H, rotamer A), 7.38-7.18 (m, 1H, rotamers A and B and 3H, rotamer B), 7.11-6.99 (m, 1H, rotamer A), 6.85 (s, 1H, rotamer A), 4.50 (s, 1H, rotamer A), 4.39 (d, J=5.7 Hz, 1H, rotamer B), 3.78-3.72 (m, 1H, rotamer B), 3.68-3.58 (m, 1H, rotamer B), 3.53-3.23 (m, 2H, rotamers A and B), 3.03-2.68 (m, 2H, rotamers A and B), 2.19-1.68 (m, 4H, rotamers A and B) ppm; ESI MS m/z 434 [M−H]⁻.

(+/−)-2-[2-(3-Chlorobenzyl)pyrrolidine-1-carbonyl]-3-hydroxyquinoxaline-6-carbonitrile (1-31)

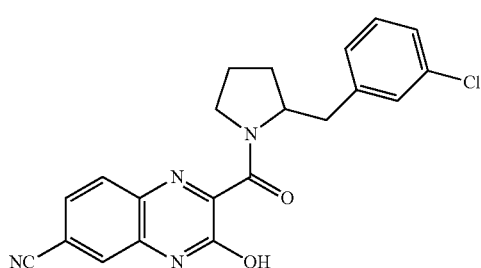

Off-white solid: ¹H NMR (400 MHz, DMSO-d₆, ~2:1 mixture of rotamers) δ 13.04 (s, 1H, rotamers A and B), 8.01 (d, J=8.3 Hz, 1H, rotamer A), 7.96 (d, J=8.3 Hz, 1H, rotamer B), 7.82-7.65 (m, 2H, rotamers A and B), 7.46-7.26 (m, 3H, rotamers A and B), 7.16 (d, J=5.1 Hz, 1H, rotamer A), 6.99-6.86 (m, 1H, rotamer B), 4.34 (s, 1H, rotamer A), 4.11 (s, 1H, rotamer B), 3.58 (s, 1H, rotamer B), 3.42 (s, 1H, rotamer B), 3.37-3.31 (m, 1H, rotamer A), 3.24 (s, 1H, rotamer A), 3.13 (dd, J=13.2, 3.3 Hz, 1H, rotamer A), 2.86 (dd, J=13.0, 8.6 Hz, 1H, rotamer A), 2.82-2.72 (m, 1H, rotamer B), 2.67 (dd, J=13.4, 8.5 Hz, 1H, rotamer B), 1.97-1.78 (m, 2H, rotamers A and B), 1.78-1.56 (m, 2H, rotamers A and B) ppm; ESI MS m/z 393 [M+H]⁺.

(+/−)-[2-(3-Chlorobenzyl)pyrrolidin-1-yl](2-hydroxypyrido[2,3-b]pyrazin-3-yl)methanone (1-32)

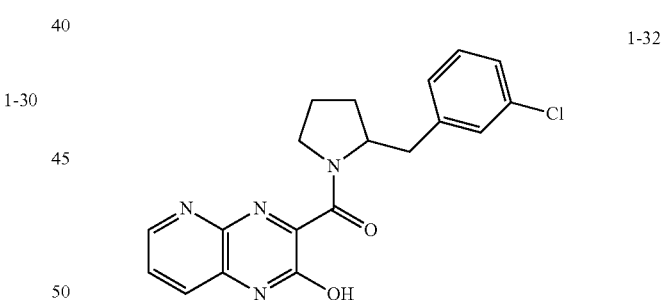

Light yellow solid: ¹H NMR (400 MHz, CD₃OD, ~2:1 mixture of rotamers) δ 8.70-8.48 (m, 1H, rotamers A and B), 7.91-7.76 (m, 1H, rotamers A and B), 7.76-7.58 (m, 1H, rotamers A and B), 7.39 (s, 1H, rotamer A), 7.36-7.28 (m, 1H, rotamers A and B and 1H, rotamer B), 7.29-7.17 (m, 2H, rotamer B), 7.11-6.96 (m, 1H, rotamer A), 6.93-6.84 (m, 1H, rotamer A), 4.59-4.35 (m, 1H, rotamers A and B), 3.84-3.68 (m, 1H, rotamer B), 3.68-3.56 (m, 1H, rotamer B), 3.56-3.37 (m, 2H, rotamer A), 2.95-2.82 (m, 2H, rotamer A), 2.76 (dd, J=13.8, 7.4 Hz, 2H, rotamer B), 2.21-1.88 (m, 2H, rotamers A and B), 1.88-1.71 (m, 2H, rotamers A and B) ppm; ESI MS m/z 369 [M+H]⁺.

(+/−)-[2-(3-Chlorobenzyl)pyrrolidin-1-yl](3-hydroxypyrido[3,2-b]pyrazin-2-yl)methanone (1-33)

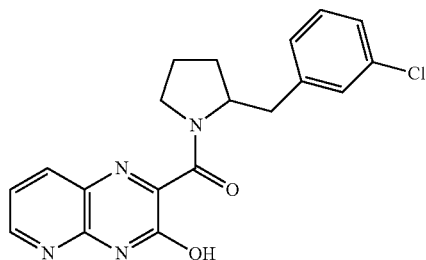

Light yellow solid: $^1$H NMR (400 MHz, CD$_3$OD, ~2:1 mixture of rotamers) δ 8.65-8.57 (m, 1H, rotamers A and B), 8.29-8.17 (m, 1H, rotamers A and B), 7.49-7.40 (m, 2H, rotamers A and B), 7.32-7.22 (m, 1H, rotamers A and B and 2H, rotamer B), 7.08 (dd, J=3.8, 1.4 Hz, 1H, rotamer A), 6.92-6.85 (m, 1H, rotamer A), 4.56-4.44 (m, 1H, rotamer A), 4.32 (d, J=7.1 Hz, 1H, rotamer B), 3.84-3.56 (m, 2H, rotamer B), 3.51-3.34 (m, 2H, rotamer A), 3.24 (dd, J=13.3, 3.5 Hz, 1H, rotamer A), 2.95 (dd, J=13.3, 8.5 Hz, 1H, rotamer A), 2.87-2.68 (m, 2H, rotamer B), 2.14-1.69 (m, 4H, rotamers A and B) ppm; ESI MS m/z 369 [M+H]$^+$.

(+/−)-[2-(3-Chlorobenzyl)pyrrolidin-1-yl](3-(trifluoromethyl)quinoxalin-2-yl)methanone (1-34)

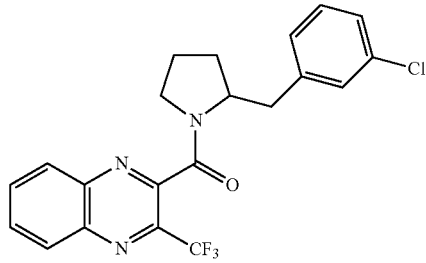

Yellow solid: $^1$H NMR (400 MHz, CD$_3$OD, ~2:1 mixture of rotamers) δ 8.42-8.20 (m, 2H, rotamers A and B), 8.19-7.99 (m, 2H, rotamers A and B), 7.44 (s, 1H, rotamer A), 7.40-7.18 (m, 2H, rotamers A and B and 1H, rotamer A), 7.12-6.87 (m, 1H, rotamer B), 6.76-6.55 (m, 1H, rotamer B), 4.57-4.46 (m, 1H, rotamer A), 4.29 (s, 1H, rotamer B), 3.90-3.59 (m, 2H, rotamer B), 3.42-3.33 (m, 1H, rotamers A and B and 1H, rotamer A), 2.97-2.81 (m, 1H, rotamer A), 2.74 (dd, J=13.7, 8.8 Hz, 1H, rotamer B), 2.24-1.65 (m, 4H, rotamers A and B) ppm; ESI MS m/z 420 [M+H]$^+$.

(+/−)-[2-(3-Chlorobenzyl)pyrrolidin-1-yl][6,7-dichloro-3-(trifluoromethyl)quinoxalin-2-yl]methanone (1-35)

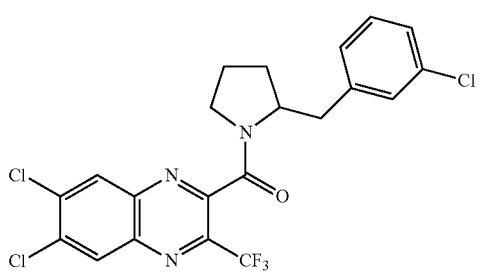

Light orange solid: $^1$H NMR (400 MHz, CD$_3$OD, ~3:1 mixture of rotamers) δ 8.51 (d, J=4.7 Hz, 1H, rotamers A and B), 8.47 (s, 1H, rotamer A), 7.42-7.21 (m, 1H, rotamers A and B and 5H, rotamer A), 7.08-6.98 (m, 2H, rotamer B), 6.83-6.66 (m, 2H, rotamer B), 4.63-4.37 (m, 1H, rotamers A and B), 3.89-3.61 (m, 2H, rotamer B), 3.48-3.32 (m, 3H, rotamer A), 2.97-2.82 (m, 1H, rotamers A and B), 2.75 (dd, J=13.8, 7.7 Hz, 1H, rotamer B), 2.17-1.93 (m, 2H, rotamers A and B), 1.93-1.71 (m, 4H, rotamers A and B) ppm; ESI MS m/z 488 [M+H]$^+$.

(+/−)-[2-(3-Chlorobenzyl)pyrrolidin-1-yl](3-chloroquinoxalin-2-yl)methanone (1-36)

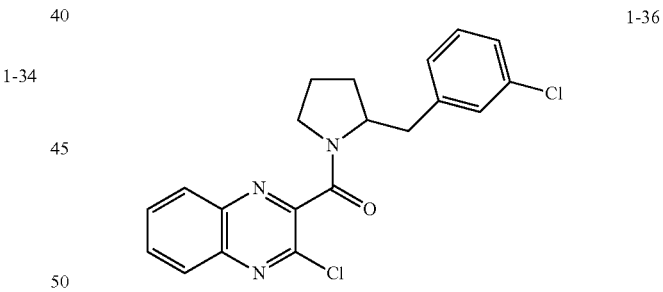

Light yellow solid: $^1$H NMR (400 MHz, CDCl$_3$, ~2:1 mixture of rotamers) δ 8.19-8.01 (m, 2H, rotamers A and B), 7.95-7.76 (m, 2H, rotamers A and B), 7.38 (s, 1H, rotamer A), 7.33-7.16 (m, 2H, rotamers A and B), 7.14-6.93 (m, 2H, rotamer B), 6.72-6.50 (m, 1H, rotamer A), 4.68-4.52 (m, 1H, rotamer A), 4.22-4.03 (m, 1H, rotamer B), 3.98-3.82 (m, 1H, rotamer B), 3.82-3.67 (m, 1H, rotamer B), 3.45 (dd, J=13.2, 3.4 Hz, 1H, rotamer A), 3.31 (t, J=6.4 Hz, 2H, rotamer A), 2.85 (dd, J=13.2, 9.1 Hz, 1H, rotamer A), 2.77 (dd, J=13.7, 4.4 Hz, 1H, rotamer B), 2.59 (dd, J=13.6, 9.1 Hz, 1H, rotamer B), 2.14-1.91 (m, 2H, rotamers A and B), 1.91-1.74 (m, 2H, rotamers A and B) ppm; ESI MS m/z 386 [M+H]$^+$.

47

(+/−)-(7-Bromo-3-hydroxyquinoxalin-2-yl)[2-(3-chlorobenzyl)pyrrolidin-1-yl]methanone (1-37)

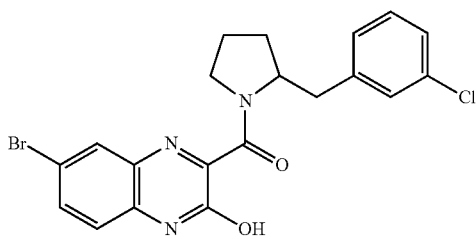

1-37

Yellow solid: ¹H NMR (400 MHz, CDCl₃, ~2:1 mixture of rotamers) δ 8.06-8.02 (m, 1H, rotamer A), 8.00 (d, 1H, rotamer B), 7.70-7.58 (m, 1H, rotamers A and B), 7.41-7.30 (m, 2H, rotamers A and B), 7.25-7.19 (m, 1H, rotamers A and B), 7.11-6.98 (m, 1H, rotamers A and B), 6.89-6.78 (m, 1H, rotamers A and B), 4.65-4.53 (m, 1H, rotamer A), 4.42 (s, 1H, rotamer B), 3.91-3.77 (m, 1H, rotamer B), 3.70 (dd, 1H, rotamer B), 3.51-3.33 (m, 2H, rotamer A), 3.29 (dd, 1H, rotamer A), 3.03-2.86 (m, 1H, rotamer A), 2.80 (dd, 1H, rotamer B), 2.70-2.59 (m, 1H, rotamer B), 2.14-1.91 (m, 2H, rotamers A and B), 1.91-1.61 (m, 2H, rotamers A and B) ppm; ESI MS m/z 446 [M+H]⁺.

(+/−)-[2-(3-Chlorobenzyl)pyrrolidin-1-yl](3-hydroxy-6,7-dimethoxyquinoxalin-2-yl)methanone (1-38)

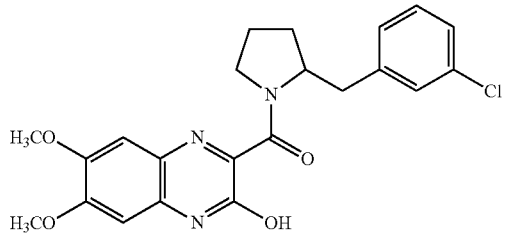

1-38

Yellow solid: ¹H NMR (400 MHz, CDCl₃, ~2:1 mixture of rotamers) δ 7.39 (s, 1H, rotamers A and B), 7.25-7.16 (m, 2H, rotamers A and B), 7.12 (d, 1H, rotamers A and B), 7.07-6.98 (m, 1H, rotamers A and B), 6.93 (s, 1H, rotamers A and B), 4.65-4.56 (m, 1H, rotamers A and B), 4.02-3.92 (m, 1H, rotamers A and B), 3.96 (s, 6H, rotamers A and B), 3.78 (s, 1H, rotamer B), 3.69 (s, 1H, rotamer A), 3.30 (dd, 1H, rotamer A), 3.06 (s, 1H, rotamer B), 2.97-2.85 (m, 1H, rotamer A), 2.70-2.60 (m, 1H, rotamer B), 2.09-1.67 (m, 4H, rotamers A and B) ppm; ESI MS m/z 428 [M+H]⁺.

48

(+/−)-[2-(3-Chlorobenzyl)pyrrolidin-1-yl][3-hydroxy-6-(trifluoromethyl)quinoxalin-2-yl]methanone (1-39)

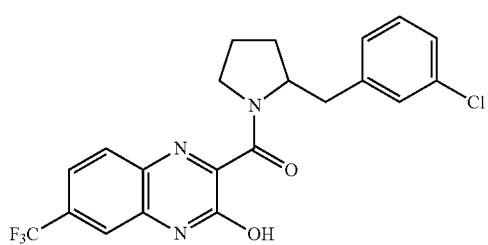

1-39

Yellow solid: ¹H NMR (400 MHz, CDCl₃, ~2:1 mixture of rotamers) δ 8.01-7.96 (m, 1H, rotamers A and B), 7.69-7.67 (m, 1H, rotamers A and B), 7.63-7.54 (m, 1H, rotamers A and B), 7.37 (s, 1H), 7.25-7.18 (m, 1H, rotamers A and B), 7.07-6.98 (m, 1H, rotamers A and B), 6.83-6.79 (m, 1H, rotamers A and B), 4.65-4.56 (m, 1H, rotamer A), 4.42 (s, 1H, rotamer B), 3.93-3.83 (m, 1H, rotamer B), 3.78-3.67 (m, 1H, rotamer B), 3.51-3.36 (m, 2H, rotamer A), 3.32 (dd, 1H, rotamer A), 2.99-2.93 (m, 1H, rotamer A), 2.91-2.62 (m, 2H, rotamer B), 2.12-1.67 (m, 4H, rotamers A and B) ppm; ESI MS m/z 434 [M−H]⁻.

(+/−)-[2-(3-Chlorobenzyl)pyrrolidin-1-yl](3-methylquinoxalin-2-yl)methanone (1-40)

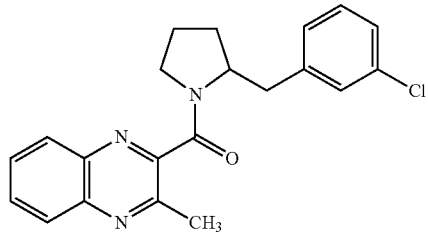

1-40

Viscous red oil: ¹H NMR (400 MHz, CD₃OD, ~3:2 mixture of rotamers) δ 8.12-8.03 (m, 2H, rotamers A and B), 7.92-7.81 (m, 2H, rotamers A and B), 7.44 (s, 1H, rotamer A), 7.30-7.26 (m, 2H, rotamers A and B), 7.02 (d, 1H, rotamer B), 6.90 (t, 1H, rotamer B), 6.60-6.57 (m, 1H, rotamer A), 4.60-4.52 (m, 1H, rotamers A and B), 3.88-3.71 (m, 1H, rotamers A and B), 3.38-3.32 (m, 2H, rotamers A and B), 2.91 (dd, 1H, rotamer A), 2.78 (s, 3H, rotamer A), 2.76-2.65 (m, 1H, rotamer B), 2.58 (s, 3H, rotamer B), 2.15-1.96 (m, 2H, rotamers A and B), 1.92-1.81 (m, 2H, rotamers A and B) ppm; ESI MS m/z 366 [M+H]⁺.

(3-Hydroxyquinoxalin-2-yl)(pyrrolidin-1-yl)methanone (1-41)

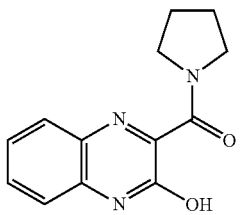

1-41

Yellow solid: ¹H NMR (400 MHz, CDCl₃) δ 11.80 (s, 1H), 7.87 (dd, 1H), 7.64-7.53 (m, 1H), 7.46-7.31 (m, 2H), 3.76 (t, 2H), 3.52 (t, 2H), 2.08-1.89 (m, 4H) ppm; ESI MS m/z 244 [M+H]⁺.

(+/−)-[2-(3,4-Dimethylbenzyl)pyrrolidin-1-yl](3-hydroxyquinoxalin-2-yl)methanone (1-42)

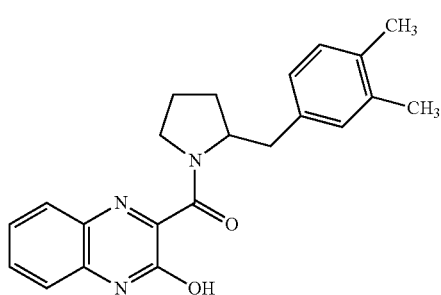

1-42

Brown solid: ¹H NMR (400 MHz, CDCl₃, ~2:1 mixture of rotamers) δ 12.02 (s, 1H, rotamers A and B), 7.89 (t, J=6.8 Hz, 1H, rotamers A and B), 7.62-7.53 (m, 1H, rotamers A and B), 7.45-7.34 (m, 2H, rotamers A and B), 7.17 (s, 1H, rotamer A), 7.09 (q, J=7.7 Hz, 2H, rotamer A), 6.82 (d, J=7.6 Hz, 1H, rotamer B), 6.60 (d, J=7.6 Hz, 1H, rotamer B), 6.51 (s, 1H, rotamer B), 4.65-4.54 (m, 1H, rotamer A), 4.37 (s, 1H, rotamer B), 3.93-3.71 (m, 2H, rotamer B), 3.52-3.39 (m, 2H, rotamer A), 3.35 (dd, J=13.2, 3.2 Hz, 1H, rotamer A), 2.94-2.77 (m, 1H, rotamers A and B), 2.59 (dd, J=13.6, 8.8 Hz, 1H, rotamer B), 2.27 (s, 3H, rotamers A and B), 2.24 (s, 3H, rotamers A and B) 2.05-1.93 (m, 2H, rotamers A and B), 1.90-1.70 (m, 2H, rotamers A and B) ppm; ESI MS m/z 362 [M+H]⁺.

(+/−)-(3-Hydroxyquinoxalin-2-yl)[2-(naphthalen-2-ylmethyl)pyrrolidin-1-yl]methanone (1-43)

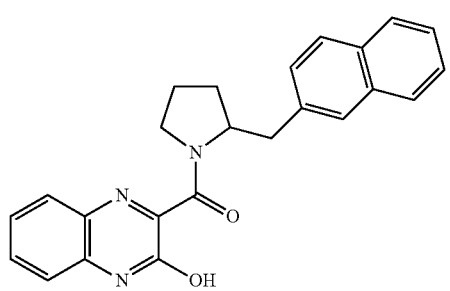

1-43

Brown solid: ¹H NMR (400 MHz, CDCl₃, ~2:1 mixture of rotamers) δ 12.41 (s, 1H, rotamers A and B), 7.90 (dd, J=8.1, 1.0 Hz, 1H, rotamers A and B), 7.86-7.73 (m, 3H, rotamers A and B), 7.68-7.50 (m, 2H, rotamers A and B), 7.50-7.28 (m, 5H, rotamers A and B), 6.93 (dd, J=8.4, 1.5 Hz, 1H, rotamer B), 4.87-4.68 (m, 1H, rotamer A), 4.62-4.48 (m, 1H, rotamer B), 3.96-3.70 (m, 2H, rotamer B), 3.62-3.31 (m, 3H, rotamer A), 3.16 (dd, J=13.2, 8.6 Hz, 1H, rotamer A), 3.09-2.75 (m, 2H, rotamer B), 2.23-1.61 (m, 4H, rotamers A and B) ppm; ESI MS m/z 382 [M−H]⁻.

(+/−)-(3-Hydroxyquinoxalin-2-yl)[2-(naphthalen-1-ylmethyl)pyrrolidin-1-yl]methanone (1-44)

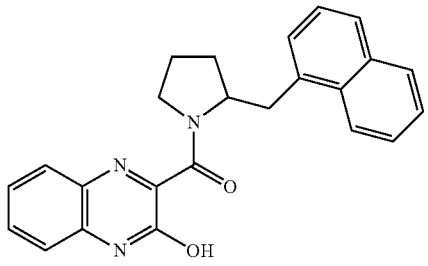

1-44

Brown solid: ¹H NMR (400 MHz, CDCl₃, ~2:1 mixture of rotamers) δ 12.01 (s, 1H, rotamers A and B), 8.80 (d, J=8.5 Hz, 1H, rotamer A), 7.88 (dd, J=18.9, 7.6 Hz, 1H, rotamers A and B and 1H, rotamer A), 7.78 (t, J=8.3 Hz, 1H, rotamers A and B), 7.67-7.47 (m, 3H, rotamers A and B), 7.47-7.30 (m, 3H, rotamers A and B), 7.19-7.12 (m, 1H, rotamers A and B), 7.09 (t, J=7.2 Hz, 1H, rotamer B), 6.54 (t, J=7.3 Hz, 1H), 4.86-4.76 (m, 1H, rotamer A), 4.74-4.62 (m, 1H, rotamer B), 4.31 (dd, J=13.1, 3.1 Hz, 1H, rotamer A), 4.02-3.79 (m, 2H, rotamer B), 3.73-3.58 (m, 1H, rotamer A), 3.58-3.46 (m, 1H, rotamer A), 3.36 (dd, J=13.8, 6.1 Hz, 1H, rotamer B), 3.05 (dd, J=13.8, 8.9 Hz, 1H, rotamer B), 2.99-2.78 (m, 1H, rotamer A), 2.24-1.71 (m, 4H, rotamers A and B) ppm; ESI MS m/z 382 [M−H]⁻.

(+/−)-(3-Hydroxyquinoxalin-2-yl)[2-(2-methoxybenzyl)pyrrolidin-1-yl]methanone (1-45)

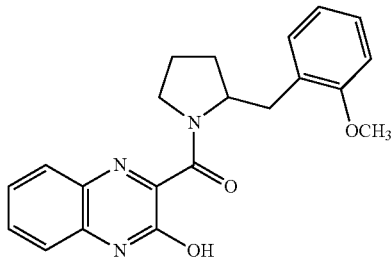

1-45

Brown solid: ¹H NMR (400 MHz, CDCl₃, ~2:1 mixture of rotamers) δ 12.27 (s, 1H, rotamers A and B), 7.92-7.83 (m, 1H, rotamers A and B), 7.64-7.48 (m, 1H, rotamer A), 7.47-7.32 (m, 2H, rotamers A and B), 7.24-7.16 (m, 1H, rotamer B), 7.09-7.00 (m, 1H, rotamer A), 6.96-6.81 (m, 1H, rotamers A and B), 6.73 (dt, J=7.4, 3.7 Hz, 2H, rotamer B), 6.47 (d, J=8.2 Hz, 1H, rotamer A), 4.76-4.65 (m, 1H, rotamer B), 4.53-4.38 (m, 1H, rotamer A), 3.94-3.73 (m, 1H, rotamers A and B), 3.84 (s, 3H, rotamer B), 3.53-3.37 (m, 1H, rotamers A and B), 3.06-2.93 (m, 1H, rotamers A and B), 2.99 (s, 3H, rotamer A), 2.55 (dd, J=13.2, 9.6 Hz, 1H, rotamers A and B), 2.22-1.75 (m, 4H, rotamers A and B) ppm; ESI MS m/z 362 [M−H]⁻.

51

(+/−)-(3-Hydroxyquinoxalin-2-yl)[2-(3-methoxybenzyl)pyrrolidin-1-yl]methanone (1-46)

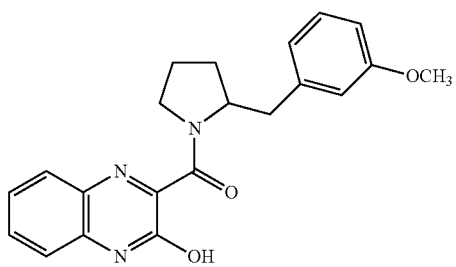

Brown solid: ¹H NMR (400 MHz, CDCl₃, ~2:1 mixture of rotamers) δ 8.87 (d, J=8.4 Hz, 1H, rotamers A and B), 7.59-7.54 (m, 1H, rotamers A and B), 7.44-7.36 (m, 2H, rotamers A and B), 7.23 (t, J=7.2 Hz, 1H, rotamers A and B), 7.01-6.94 (m, 2H, rotamer A), 6.79 (d, J=8.4 Hz, rotamer A), 6.62 (d, J=7.8 Hz, rotamer B), 6.48 (d, J=7.2 Hz, 1H, rotamer B), 6.48 (d, J=7.2 Hz, 1H, rotamer B), 6.35 (s, 1H, rotamer B), 4.67-4.60 (m, 1H, rotamer A), 4.40-4.35 (m, 1H, rotamer B), 3.90-3.71 (m, 1H, rotamers A and B and 1H, rotamer B), 3.82 (s, 3H, rotamer A), 3.49 (s, 3H, rotamer B), 3.47-3.35 (m, 2H, rotamer A), 2.97-2.84 (m, 1H, rotamers A and B), 2.68-2.61 (m, 1H, rotamer B), 2.05-1.69 (m, 4H, rotamers A and B) ppm; ESI MS m/z 362 [M−H]⁻.

(S)-(2-Benzhydrylpyrrolidin-1-yl)(3-hydroxyquinoxalin-2-yl)methanone (1-47)

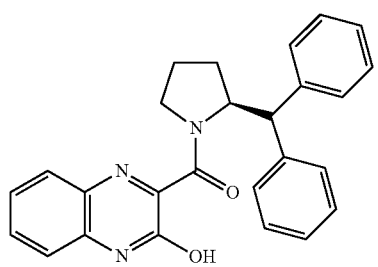

Orange solid: ¹H NMR (400 MHz, CDCl₃, ~2:1 mixture of rotamers) δ 12.75 (s, 1H, rotamers A and B), 7.91 (dd, J=8.1, 1.1 Hz, 1H, rotamer A), 7.83 (dd, J=8.1, 1.0 Hz, 1H, rotamer B), 7.64-7.52 (m, 1H, rotamers A and B), 7.49-7.30 (m, 5H, rotamers A and B), 7.30-7.11 (m, 5H, rotamers A and B), 6.96-6.84 (m, 2H, rotamers A and B), 5.28-5.21 (m, 2H, rotamer B), 5.17 (d, J=3.9 Hz, 1H, rotamer A), 4.11 (d, J=8.1 Hz, 1H, rotamer A), 4.06-3.90 (m, 1H, rotamer B), 3.68-3.57 (m, 1H, rotamer B), 3.47-3.32 (m, 1H, rotamer A), 3.15-3.02 (m, 1H, rotamer A), 2.36-2.20 (m, 1H, rotamers A and B), 2.19-2.06 (m, 1H, rotamers A and B), 2.04-1.87 (m, 1H, rotamers A and B), 1.73-1.56 (m, 1H, rotamers A and B) ppm; ESI MS m/z 408 [M−H]⁻.

52

(+/−)-(3-Hydroxyquinoxalin-2-yl)[2-(1-phenylpropyl)pyrrolidin-1-yl]methanone (mixture of diastereomers) (1-48)

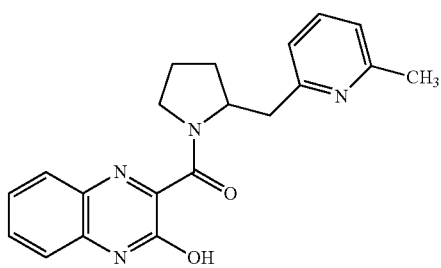

Orange solid: ¹H NMR (400 MHz, CDCl₃, ~2:1 mixture of rotamers) δ 12.39 (s, 1H, rotamers A and B), 7.94-7.84 (m, 1H, rotamers A and B), 7.64-7.49 (m, 1H, rotamers A and B), 7.49-7.23 (m, 6H, rotamers A and B), 7.08-6.96 (m, 1H, rotamer A), 6.78-6.70 (m, 1H, rotamer B), 4.70-4.59 (m, 1H, rotamer A), 4.47 (s, 1H, rotamer B), 4.14-4.01 (m, 2H, rotamer B), 3.53-3.29 (m, 1H, rotamers A and B and 2H, rotamer A), 2.13-1.78 (m, 4H, rotamers A and B), 1.78-1.59 (m, 2H, rotamers A and B), 0.95 (t, J=7.3 Hz, 3H, rotamer A), 0.62 (t, J=7.2 Hz, 3H, rotamer B) ppm; ESI MS m/z 360 [M−H]⁻.

(+/−)-(3-Hydroxyquinoxalin-2-yl){2-[(6-methylpyridin-2-yl)methyl]pyrrolidin-1-yl}methanone (1-49)

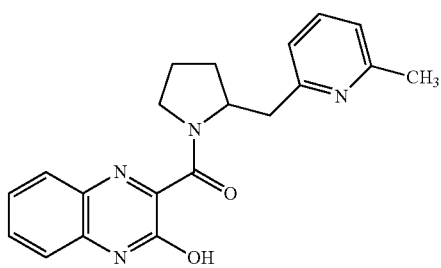

Yellow solid: ¹H NMR (400 MHz, CDCl₃, ~2:1 mixture of rotamers) δ 12.44 (s, 1H, rotamers A and B), 7.88 (d, 1H, rotamer A), 7.83 (d, 1H, rotamer B), 7.58-7.50 (m, 2H, rotamers A and B), 7.44-7.34 (m, 2H, rotamers A and B), 7.34-7.24 (m, 1H, rotamer A), 7.01 (d, 1H, rotamer B), 6.74 (t, 1H, rotamers A and B), 4.75-4.65 (m, 1H, rotamers A and B), 3.92-3.84 (m, 1H, rotamer A), 3.79-3.73 (m, 1H, rotamer B), 3.55 (d, 1H, rotamer A), 3.52-3.40 (m, 1H, rotamers A and B), 3.13 (dd, 1H, rotamer B), 3.00 (dd, 1H, rotamer A), 2.78 (dd, rotamer B), 2.02 (s, 3H, rotamers A and B), 2.12-1.85 (m, 4H, rotamers A and B) ppm; ESI MS m/z 349 [M+H]⁺.

(3-Hydroxy-6,7-dimethoxyquinoxalin-2-yl)(pyrrolidin-1-yl)methanone (1-50)

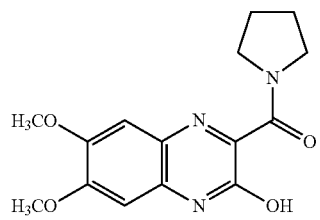
1-50

Yellow solid: $^1$H NMR (400 MHz, CDCl$_3$) δ 7.22 (s, 1H), 6.97 (s, 1H), 4.02 (s, 3H), 3.97 (s, 3H), 3.84 (s, 2H), 3.74 (t, 2H), 2.06-1.91 (m, 4H) ppm; ESI MS m/z 304 [M+H]$^+$.

(+/−)-[2-(3-Fluorobenzyl)pyrrolidin-1-yl](3-hydroxyquinoxalin-2-yl)methanone (1-51)

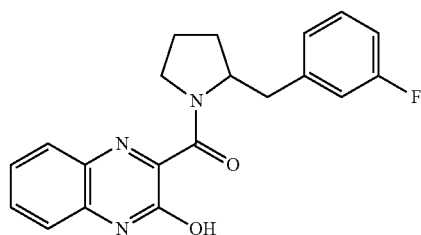
1-51

Yellow solid: $^1$H NMR (400 MHz, CDCl$_3$, ~2:1 mixture of rotamers) δ 7.95-7.84 (m, 1H, rotamers A and B), 7.63-7.52 (m, 1H, rotamers A and B), 7.48-7.34 (m, 2H, rotamers A and B), 7.32-7.11 (m, 2H, rotamers A and B), 7.09-7.01 (m, 1H, rotamer B), 6.97-6.89 (m, 1H, rotamer A), 6.83-6.76 (m, 1H, rotamer B), 6.67 (t, 1H, rotamer A), 4.68-4.56 (m, 1H, rotamer A), 4.40 (s, 1H, rotamer B), 3.95-3.81 (m, 1H, rotamer B), 3.76-3.63 (m, 1H, rotamer B), 3.53-3.27 (m, 3H, rotamer A), 3.03 (dd, 1H, rotamer A), 2.88 (dd, 1H, rotamer B), 2.69 (dd, 1H, rotamer B), 2.16-1.91 (m, 1H, rotamers A and B), 1.91-1.75 (m, 2H, rotamers A and B), 1.75-1.57 (m, 1H, rotamers A and B) ppm; ESI MS m/z 352 [M+H]$^+$.

(+/−)-[2-(2-Chloro-6-fluorobenzyl)pyrrolidin-1-yl](3-hydroxyquinoxalin-2-yl)methanone (1-52)

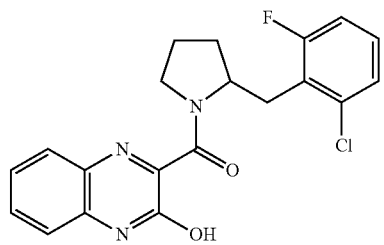
1-52

Yellow solid: $^1$H NMR (400 MHz, CDCl$_3$, ~2:1 mixture of rotamers) δ 12.36 (s, 1H, rotamers A and B), 7.91-7.82 (m, 1H, rotamers A and B), 7.62-7.51 (m, 1H, rotamers A and B), 7.43 (d, 1H, rotamers A and B), 7.40-7.33 (m, 1H, rotamers A and B), 7.24-7.12 (m, 1H, rotamers A and B), 7.04-6.90 (m, 1H, rotamers A and B), 6.76 (t, 1H, rotamers A and B), 4.84 (s, 1H, rotamer B), 4.49-4.34 (m, 1H, rotamer A), 3.98-3.81 (m, 1H, rotamers A and B), 3.77-3.58 (m, 1H, rotamer A), 3.58-3.43 (m, 1H, rotamer B), 3.10-2.87 (m, 2H, rotamers A and B), 2.35-2.17 (m, 1H, rotamers A and B), 2.17-2.05 (m, 1H, rotamers A and B), 2.05-1.84 (m, 1H, rotamers A and B), 1.84-1.59 (m, 1H, rotamers A and B) ppm; ESI MS m/z 386 [M+H]$^+$.

(S)-{2-[(1H-tetrazol-5-yl)methyl]pyrrolidin-1-yl}(3-hydroxyquinoxalin-2-yl)methanone (1-53)

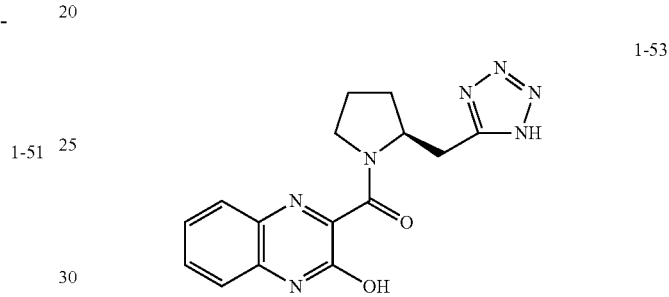
1-53

Yellow solid: $^1$H NMR (400 MHz, DMSO-d$_6$, ~2:1 mixture of rotamers) δ 7.83 (dd, J=8.4, 1.3 Hz, 1H, rotamer A), 7.75 (d, J=8.1 Hz, 1H, rotamer B), 7.70-7.54 (m, 1H, rotamers A and B), 7.43-7.30 (m, 2H, rotamers A and B), 4.50-4.41 (m, 1H, rotamer A), 4.27-4.19 (m, 1H, rotamer B), 3.57-3.47 (m, 1H, rotamers A and B), 3.38-3.33 (m, 2H, rotamers A and B), 3.16-3.05 (m, 1H, rotamers A and B), 2.07-1.65 (m, 4H, rotamers A and B) ppm; ESI MS m/z 324 [M−H]$^-$.

(S)-(3-Hydroxyquinoxalin-2-yl)[2-(methoxymethyl)pyrrolidin-1-yl]methanone (1-54)

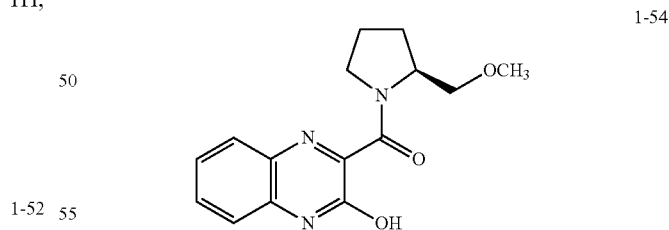
1-54

Yellow solid: $^1$H NMR (400 MHz, CDCl$_3$, ~2:1 mixture of rotamers) δ 11.93 (s, 1H, rotamers A and B), 7.92-7.79 (m, 1H, rotamers A and B), 7.61-7.49 (m, 1H, rotamers A and B), 7.43-7.30 (m, 2H, rotamers A and B), 4.60-4.47 (m, 1H, rotamer A), 4.37-4.27 (m, 1H, rotamer B), 3.95-3.71 (m, 2H, rotamers A and B), 3.64 (dd, J=9.5, 7.0 Hz, 1H, rotamer A), 3.57-3.47 (m, 1H, rotamer B), 3.46 (s, 3H, rotamer A), 3.34-3.19 (m, 1H, rotamers A and B), 3.08 (s, 3H, rotamer B), 2.24-1.81 (m, 4H, rotamers A and B) ppm; ESI MS m/z 286 [M−H]$^-$.

(+/−)-{2-[(4-fluorophenoxy)methyl]pyrrolidin-1-yl}(3-hydroxyquinoxalin-2-yl)methanone (1-55)

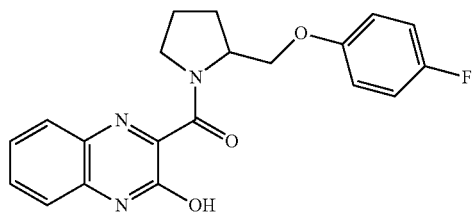

Yellow solid: $^1$H NMR (400 MHz, CDCl$_3$, ~2:1 mixture of rotamers) δ 12.41 (s, 1H, rotamers A and B), 7.94-7.75 (m, 1H, rotamers A and B), 7.60-7.45 (m, 1H, rotamers A and B), 7.44-7.28 (m, 2H, rotamers A and B), 6.98 (d, J=6.3 Hz, 3H, rotamers A and B), 6.69-6.43 (m, 1H, rotamers A and B), 4.80-4.62 (m, 1H, rotamer A), 4.49 (q, J=6.4 Hz, 1H, rotamer B), 4.41 (dd, J=9.5, 3.1 Hz, 1H, rotamer A), 4.19 (dd, J=9.5, 7.1 Hz, 1H, rotamer A), 4.05-3.89 (m, 1H, rotamer A), 3.85-3.69 (m, 1H, rotamer A), 3.68-3.40 (m, 4H, rotamer B), 2.38-1.87 (m, 4H, rotamers A and B) ppm; ESI MS m/z 366 [M−H]$^-$.

(+/−)-{2-[(1H-Pyrazol-1-yl)methyl]pyrrolidin-1-yl}(3-hydroxyquinoxalin-2-yl)methanone (1-56)

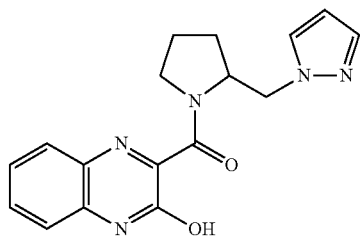

Yellow solid: $^1$H NMR (400 MHz, CDCl$_3$) δ 12.27 (s, 1H), 7.93 (d, J=2.1 Hz, 1H), 7.92-7.87 (m, 1H), 7.65-7.56 (m, 1H), 7.52 (d, J=1.4 Hz, 1H), 7.49-7.36 (m, 2H), 6.26 (t, J=2.1 Hz, 1H), 4.94 (dd, J=14.2, 4.6 Hz, 1H), 4.67-4.58 (m, 1H), 4.52 (dd, J=14.2, 2.6 Hz, 1H), 3.49-3.38 (m, 1H), 3.24-3.13 (m, 1H), 2.24-2.01 (m, 2H), 1.78-1.65 (m, 1H), 1.21-1.05 (m, 1H) ppm; ESI MS m/z 322 [M−H]$^-$.

(+/−)-(3-Hydroxyquinoxalin-2-yl)[2-(piperidin-1-ylmethyl)pyrrolidin-1-yl]methanone (1-57)

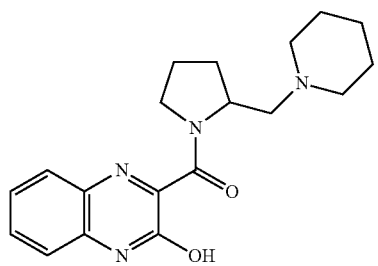

Yellow solid: $^1$H NMR (400 MHz, CDCl$_3$, ~2:1 mixture of rotamers) δ 7.91-7.79 (m, 1H, rotamers A and B), 7.59-7.51 (m, 1H, rotamers A and B), 7.43-7.30 (m, 2H, rotamers A and B), 4.54 (s, 1H, rotamer B), 4.29 (dd, J=12.5, 6.0 Hz, 1H, rotamer A), 3.88-3.72 (m, 1H, rotamers A and B), 3.58-3.40 (m, 1H, rotamers A and B), 2.95-2.34 (m, 2H, rotamers A and B), 2.23-1.84 (m, 6H, rotamers A and B), 1.70-1.34 (m, 3H, rotamers A and B), 1.32-0.92 (m, 4H, rotamers A and B) ppm; ESI MS m/z 341 [M+H]$^-$.

(+/−)-(3-Hydroxyquinoxalin-2-yl)(2-methylpyrrolidin-1-yl)methanone (1-58)

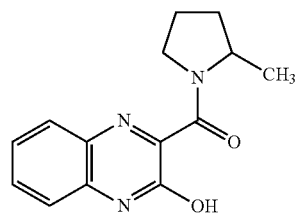

Yellow solid: $^1$H NMR (400 MHz, CDCl$_3$, ~2:1 mixture of rotamers) δ 11.98 (s, 1H, rotamers A and B), 7.87 (dd, J=8.4, 2.7 Hz, 1H, rotamers A and B), 7.64-7.51 (m, 1H, rotamers A and B), 7.48-7.31 (m, 2H, rotamers A and B), 4.57-4.42 (m, 1H, rotamer A), 4.21-4.06 (m, 1H, rotamer B), 3.90-3.71 (m, 1H, rotamers A and B), 3.62-3.41 (m, 1H, rotamers A and B), 2.24-1.83 (m, 3H, rotamers A and B), 1.78-1.62 (m, 1H, rotamers A and B), 1.44 (d, J=6.4 Hz, 3H, rotamer A), 1.11 (d, J=6.5 Hz, 3H, rotamer B) ppm; ESI MS m/z 256 [M−H]$^-$.

(S)-Benzyl 1-(3-hydroxyquinoxaline-2-carbonyl)pyrrolidine-2-carboxylate (1-59)

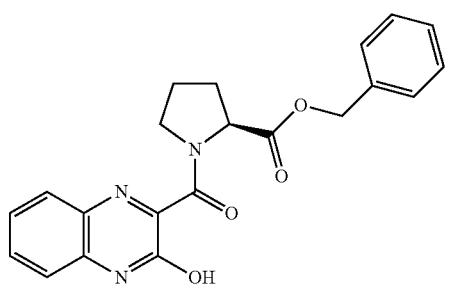

Brown solid: $^1$H NMR (400 MHz, CDCl$_3$) δ 12.36 (s, 1H), 7.91-7.63 (m, 1H), 7.59-7.48 (m, 1H), 7.48-7.39 (m, 2H), 7.39-7.27 (m, 3H), 7.24-7.14 (m, 1H), 7.14-7.06 (m, 1H), 5.33-5.20 (m, 1H), 5.04 (q, J=12.2 Hz, 1H), 4.92-4.77 (m, 1H), 4.02-3.83 (m, 1H), 3.81-3.55 (m, 1H), 2.45-2.27 (m, 1H), 2.25-1.91 (m, 3H) ppm; ESI MS m/z 378 [M+H]$^+$.

(+/−)-[2-(Cyclohexylmethyl)pyrrolidin-1-yl](3-hydroxyquinoxalin-2-yl)methanone (1-60)

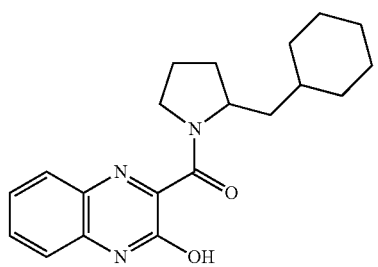

Brown solid: $^1$H NMR (400 MHz, CDCl$_3$, ~1:1 mixture of rotamers) δ 12.21 (s, 1H, rotamers A and B), 7.87 (dd, J=8.1, 1.1 Hz, 1H, rotamers A and B), 7.61-7.51 (m, 1H, rotamers A and B), 7.47-7.33 (m, 2H, rotamers A and B), 4.55-4.44 (m, 1H, rotamer A), 4.07 (s, 1H, rotamer B), 3.89-3.68 (m, 1H, rotamers A and B), 3.58-3.31 (m, 1H, rotamers A and B), 2.16-1.58 (m, 6H, rotamers A and B), 1.51-0.66 (m, 8H, rotamers A and B) ppm; ESI MS m/z 338 [M−H]$^-$.

(+/−)-(3-Hydroxyquinoxalin-2-yl)(2-isobutylpyrrolidin-1-yl)methanone (1-61)

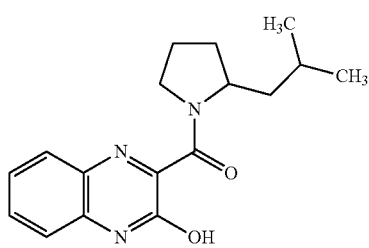

1-61

Brown solid: $^1$H NMR (400 MHz, CDCl$_3$, ~1:1 mixture of rotamers) δ 7.87 (d, J=8.5 Hz, 1H, rotamers A and B), 7.58-7.53 (m, 1H, rotamers A and B), 7.43-7.34 (m, 2H, rotamers A and B), 4.50-4.44 (m, 1H, rotamer A), 4.06-4.00 (m, 1H, rotamer B), 3.86-3.70 (m, 2H, rotamer B), 3.55-3.42 (m, 2H, rotamer A), 2.11-1.86 (m, 3H, rotamers A and B), 1.80-1.64 (m, 2H, rotamers A and B), 1.44-1.31 (m, 2H, rotamers A and B), 1.03 (dd, J=6.3, 10.9 Hz, 6H, rotamer A), 0.68 (d, J=6.5 Hz, 3H, rotamer B), 0.38 (d, J=5.7 Hz, 3H, rotamer B) ppm; ESI MS m/z 298 [M−H]$^-$.

(+/−)-(3-Hydroxyquinoxalin-2-yl)(2-neopentylpyrrolidin-1-yl)methanone (1-62)

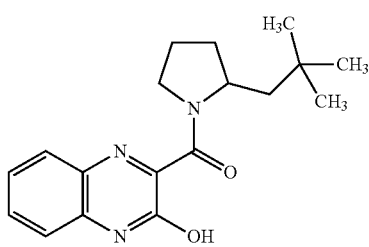

1-62

Brown solid: $^1$H NMR (400 MHz, CDCl$_3$, ~1:1 mixture of rotamers) δ 12.49 (s, 1H, rotamers A and B), 7.87 (d, J=8.1 Hz, 1H, rotamers A and B), 7.65-7.48 (m, 1H, rotamers A and B), 7.48-7.31 (m, 2H, rotamers A and B), 4.43 (t, J=8.1 Hz, 1H, rotamer A), 4.10-3.98 (m, 1H, rotamer B), 3.86-3.66 (m, 1H, rotamers A and B), 3.56-3.31 (m, 1H, rotamers A and B), 2.24-1.72 (m, 4H, rotamers A and B), 1.58-1.29 (m, 2H, rotamers A and B), 1.06 (s, 9H, rotamer A), 0.53 (s, 9H, rotamer B) ppm; ESI MS m/z 312 [M−H]$^-$.

(+/−)-(3-Hydroxyquinoxalin-2-yl)[2-(pyridin-3-ylmethyl)pyrrolidin-1-yl]methanone (1-63)

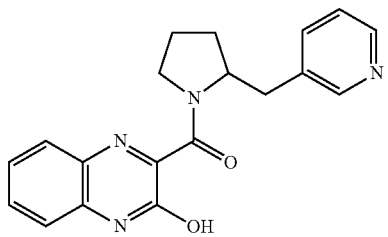

1-63

Yellow solid: $^1$H NMR (400 MHz, CDCl$_3$, ~2:1 mixture of rotamers) δ 8.67 (s, 1H, rotamer A), 8.53 (d, 1H, rotamer A), 8.39 (d, 1H, rotamer B), 8.22 (s, 1H, rotamer B), 8.04-7.71 (m, 2H, rotamers A and B), 7.66-7.09 (s, 4H, rotamers A and B), 4.63 (s, 1H, rotamer A), 4.36 (s, 1H, rotamer B), 3.78 (d, 2H, rotamer B), 3.58-3.03 (m, 4H, rotamer A), 3.01-2.61 (m, 2H, rotamer B), 2.25-1.51 (m, 4H, rotamers A and B) ppm; ESI MS m/z 335 [M+H]$^+$.

(+/−)-{2-[(3-Chloro-4-fluorophenoxy)methyl]pyrrolidin-1-yl}(3-hydroxyquinoxalin-2-yl)methanone (1-64)

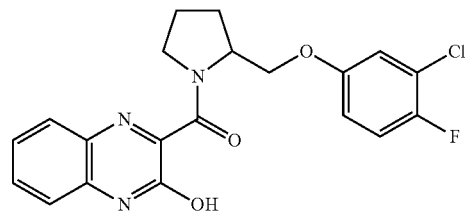

1-64

Orange solid: $^1$H NMR (400 MHz, CDCl$_3$, ~2:1 mixture of rotamers) δ 7.92-7.85 (m, 1H, rotamer A), 7.82 (dd, 1H, rotamer B), 7.58-7.49 (m, 1H, rotamers A and B), 7.42-7.34 (m, 1H, rotamers A and B), 7.30 (d, 1H, rotamers A and B), 7.10-7.01 (m, 1H, rotamers A and B), 6.96-6.43 (m, 2H, rotamers A and B), 4.75-4.65 (m, 1H, rotamer A), 4.56-4.48 (m, 1H, rotamer B), 4.40 (dd, 1H, rotamers A and B), 4.24-4.13 (m, 1H, rotamers A and B), 4.00-3.73 (m, 1H, rotamers A and B), 3.64-3.49 (m, 1H, rotamers A and B), 2.31-1.91 (m, 4H, rotamers A and B) ppm; ESI MS m/z 402 [M+H]$^+$.

(S)-(3-Hydroxyquinoxalin-2-yl){2-[(phenylamino)methyl]pyrrolidin-1-yl}methanone (1-65)

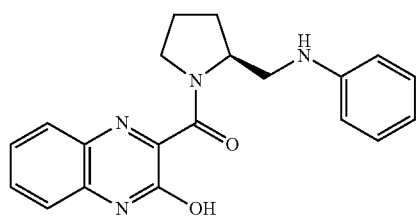

1-65

Orange solid: ¹H NMR (400 MHz, CDCl₃, ~2:1 mixture of rotamers) δ 7.92-7.49 (m, 1H, rotamers A and B), 7.41-7.24 (m, 2H, rotamers A and B), 7.22-7.06 (m, 2H, rotamers A and B), 6.75 (dd, 1H, rotamers A and B), 6.72-6.59 (m, 2H, rotamers A and B), 6.27-6.19 (m, 1H, rotamers A and B), 4.76 (s, 1H, rotamer B), 4.73-4.60 (m, 1H, rotamer A), 3.99-3.65 (m, 1H, rotamers A and B), 3.63-3.39 (m, 2H, rotamers A and B), 3.22-2.86 (m, 1H, rotamers A and B), 2.35-1.79 (m, 4H, rotamers A and B) ppm; ESI MS m/z 349 [M+H]⁺.

(R)-(3-Hydroxyquinoxalin-2-yl){2-[(phenylamino)methyl]pyrrolidin-1-yl}methanone (1-66)

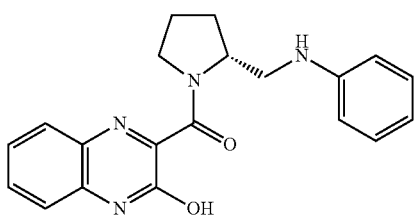

1-66

Orange solid: ¹H NMR (400 MHz, CDCl₃, ~2:1 mixture of rotamers) δ 7.92-7.49 (m, 1H, rotamers A and B), 7.41-7.24 (m, 2H, rotamers A and B), 7.22-7.06 (m, 2H, rotamers A and B), 6.75 (dd, 1H, rotamers A and B), 6.72-6.59 (m, 2H, rotamers A and B), 6.27-6.19 (m, 1H, rotamers A and B), 4.76 (s, 1H, rotamer B), 4.73-4.60 (m, 1H, rotamer A), 3.99-3.65 (m, 1H, rotamers A and B), 3.63-3.39 (m, 2H, rotamers A and B), 3.22-2.86 (m, 1H, rotamers A and B), 2.35-1.79 (m, 4H, rotamers A and B) ppm; ESI MS m/z 349 [M+H]⁺.

(3-Hydroxyquinoxalin-2-yl)(indolin-1-yl)methanone (1-67)

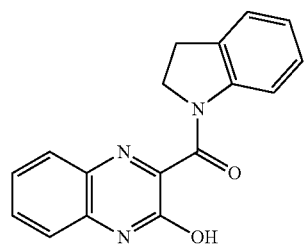

1-67

Orange solid: ¹H NMR (400 MHz, CDCl₃) δ 12.42 (s, 1H), 8.41 (d, 1H), 7.88 (dd, 1H), 7.61-7.47 (m, 1H), 7.47-7.35 (m, 2H), 7.31 (t, 1H), 7.25-7.19 (m, 1H), 7.13 (td, 1H), 4.13 (t, 2H), 3.21 (t, 2H) ppm; ESI MS m/z 292 [M+H]⁺.

(7-Chloroindolin-1-yl)(3-hydroxyquinoxalin-2-yl)methanone (1-68)

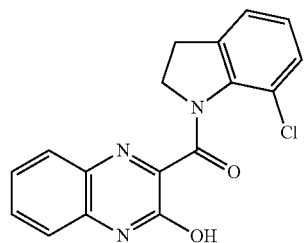

1-68

Brown solid: ¹H NMR (400 MHz, CDCl₃) δ 12.58 (s, 1H), 7.60 (s, 1H), 7.53 (t, 1H), 7.42 (d, 1H), 7.28 (s, 1H), 7.20 (d, 1H), 7.00 (s, 2H), 3.22 (s, 2H), 1.39-1.05 (m, 2H) ppm; ESI MS m/z 326 [M+H]⁺.

(6-Chloroindolin-1-yl)(3-hydroxyquinoxalin-2-yl)methanone (1-69)

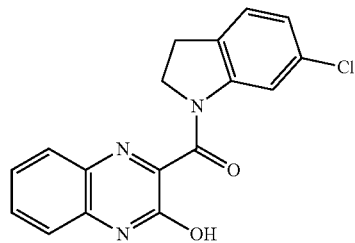

1-69

Yellow solid: ¹H NMR (400 MHz, DMSO-d₆) δ 12.91 (s, 1H), 8.11 (d, 1H), 7.84 (dd, 1H), 7.72-7.57 (m, 1H), 7.46-7.35 (m, 3H), 7.32 (dd, 1H), 4.02 (t, 2H), 3.16 (t, 2H) ppm; ESI MS m/z 326 [M+H]⁺.

(6-Fluoroindolin-1-yl)(3-hydroxyquinoxalin-2-yl)methanone (1-70)

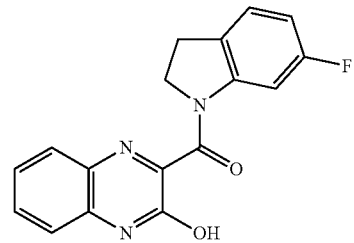

1-70

Yellow solid: ¹H NMR (400 MHz, DMSO-d₆) δ 12.93 (s, 1H), 7.94-7.80 (m, 2H), 7.71-7.59 (m, 1H), 7.46-7.36 (m, 2H), 7.36-7.28 (m, 1H), 7.00-6.91 (m, 1H), 4.06 (t, 2H), 3.13 (t, 2H) ppm; ESI MS m/z 310 [M+H]⁺.

(5-Fluoroindolin-1-yl)(3-hydroxyquinoxalin-2-yl)methanone (1-71)

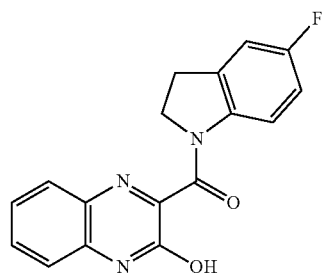

1-71

Yellow solid: $^1$H NMR (400 MHz, DMSO-d$_6$) δ 12.90 (s, 1H), 8.13 (dd, 1H), 7.84 (d, 1H), 7.65 (t, 1H), 7.42-7.37 (m, 2H), 7.20 (dd, 1H), 7.09 (t, 1H), 4.02 (t, 2H), 3.16 (t, 2H) ppm; ESI MS m/z 310 [M+H]$^+$.

(+/−)-(2-Benzylpiperidin-1-yl)(3-hydroxyquinoxalin-2-yl)methanone (1-72)

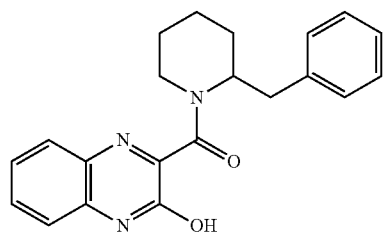

1-72

Yellow solid: $^1$H NMR (400 MHz, CDCl$_3$, ~1:1 mixture of rotamers) δ 12.46 (s, 1H, rotamers A and B), 7.92-7.80 (m, 1H, rotamers A and B), 7.60-7.49 (m, 1H, rotamers A and B), 7.42-7.21 (m, 5H, rotamers A and B), 7.15-7.02 (m, 1H, rotamers A and B), 6.92 (dd, 1H, rotamers A and B), 5.19-5.09 (m, 1H, rotamer A), 4.85-4.76 (m, 1H, rotamer B), 3.89-3.80 (m, 1H, rotamer A), 3.50-3.32 (m, 1H, rotamers A and B), 3.22-3.20 (m, 1H, rotamer B), 3.20-3.00 (m, 2H, rotamers A and B), 1.99-1.48 (m, 6H, rotamers A and B) ppm; ESI MS m/z 348 [M+H]$^+$.

(+/−)-(3-Hydroxyquinoxalin-2-yl)[2-(2-methoxybenzyl)piperidin-1-yl]methanone (1-73)

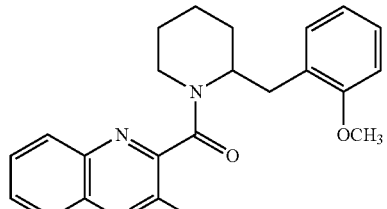

1-73

Yellow solid: $^1$H NMR (400 MHz, CDCl$_3$, ~1:1 mixture of rotamers) δ 12.43 (s, 1H, rotamers A and B), 7.85 (dd, J=14.0, 7.9 Hz, 1H, rotamers A and B), 7.60-7.47 (m, 1H, rotamers A and B), 7.45-7.29 (m, 4H, rotamers A and B), 7.05 (t, J=7.6 Hz, 1H, rotamer A), 7.01-6.87 (m, 1H, rotamer B), 6.74 (t, J=7.3 Hz, 1H, rotamer A), 6.56 (d, J=8.2 Hz, 1H, rotamer B), 4.78 (d, J=12.4 Hz, 1H, rotamer A), 4.06 (s, 1H, rotamer B), 3.48-2.94 (m, 24, rotamers A and B), 3.18 (s, 3H, rotamers A and B), 1.97-1.79 (m, 2H, rotamers A and B), 1.79-1.53 (m, 3H, rotamers A and B), 1.48 (d, J=13.2 Hz, 1H, rotamers A and B) ppm; ESI MS m/z 378 [M+H]$^+$.

(+/−)-[2-(3-Fluorobenzyl)piperidin-1-yl](3-hydroxyquinoxalin-2-yl)methanone (1-74)

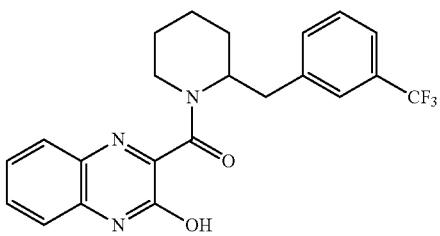

1-74

Brown solid: $^1$H NMR (400 MHz, CDCl$_3$, ~1:1 mixture of rotamers) δ 12.38 (s, 1H, rotamers A and B), 7.91-7.80 (m, 1H, rotamers A and B), 7.60-7.50 (m, 1H, rotamers A and B), 7.42-7.33 (m, 2H, rotamers A and B), 7.33-7.27 (m, 1H, rotamer A), 7.15 (d, 1H, rotamer B), 7.13-7.03 (m, 1H, rotamers A and B), 6.94 (td, 1H, rotamer A), 6.77 (td, 1H, rotamer B), 6.71 (d, 1H, rotamer A), 6.68-6.60 (m, 1H, rotamer B), 5.14 (d, 1H, rotamer A), 4.80 (d, 1H, rotamer B), 3.84 (d, 1H, rotamer A), 3.53-3.27 (m, 1H, rotamers A and B), 3.26-3.18 (m, 1H, rotamer B), 3.18-2.96 (m, 2H, rotamers A and B), 1.98-1.44 (m, 6H, rotamers A and B) ppm; ESI MS m/z 366 [M+H]$^+$.

(+/−)-(3-Hydroxyquinoxalin-2-yl){2-[3-(trifluoromethyl)benzyl]piperidin-1-yl}methanone (1-75)

1-75

Brown solid: $^1$H NMR (400 MHz, CDCl$_3$, ~1:1 mixture of rotamers) δ 12.11 (s, 1H, rotamers A and B), 7.87 (dd, 1H, rotamer A), 7.81 (dd, 1H, rotamer B), 7.62-7.42 (m, 3H, rotamers A and B), 7.41-7.27 (m, 3H, rotamers A and B), 7.16-7.14 (m, 1H, rotamers A and B), 5.20-5.11 (m, 1H, rotamer A), 4.82 (d, 1H, rotamer B), 3.88-3.77 (m, 1H, rotamer A), 3.51-3.45 (m, 1H, rotamer B), 3.45-3.27 (m, 1H, rotamers A and B), 3.21-2.99 (m, 2H, rotamers A and B), 1.95-1.51 (m, 6H, rotamers A and B) ppm; ESI MS m/z 416 [M+H]$^+$.

(+/−)-(6,7-Dichloro-3-hydroxyquinoxalin-2-yl)[2-(3-(trifluoromethyl)benzyl]piperidin-1-yl)methanone (1-76)

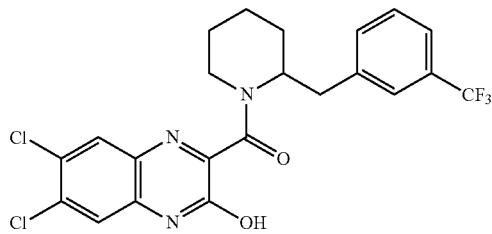

Brown solid: ¹H NMR (400 MHz, CDCl₃, ~1:1 mixture of rotamers) δ 7.93 (s, 1H, rotamer A), 7.84 (s, 1H, rotamer B), 7.58-7.43 (m, 1H, rotamers A and B), 7.42-7.31 (m, 3H, rotamers A and B), 7.18-7.14 (m, 1H, rotamers A and B), 5.15-5.10 (m, 1H, rotamer A), 4.82-4.76 (m, 1H, rotamer B), 3.84-3.78 (m, 1H, rotamer A), 3.43-3.31 (m, 1H, rotamers A and B), 3.26-3.21 (m, 1H, rotamer B), 3.18-3.00 (m, 2H, rotamers A and B), 1.94-1.54 (m, 6H, rotamers A and B) ppm; ESI MS m/z 484 [M+H]⁺.

(+/−)-(3-Hydroxyquinoxalin-2-yl)[2-(3-methylbenzyl)piperidin-1-yl]methanone (1-77)

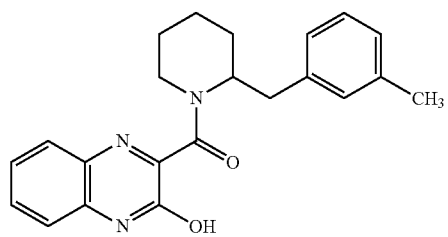

Brown solid: ¹H NMR (400 MHz, CDCl₃, ~1:1 mixture of rotamers) δ 12.41 (s, 1H, rotamers A and B), 7.92-7.82 (m, 1H, rotamers A and B), 7.61-7.48 (m, 1H, rotamers A and B), 7.44-7.31 (m, 2H, rotamers A and B), 7.25-7.12 (m, 1H, rotamers A and B), 7.11-6.95 (m, 1H, rotamers A and B), 6.86 (d, J=7.6 Hz, 1H, rotamers A and B), 6.76-6.64 (m, 1H, rotamers A and B), 5.18-5.05 (m, 1H, rotamer B), 4.80 (d, J=11.7 Hz, 1H, rotamer A), 3.87-3.74 (m, 1H, rotamer B), 3.54-3.31 (m, 1H, rotamer A and B and 1H, rotamer A), 3.19-2.97 (m, 2H, rotamers A and B), 2.37 (s, 5H, rotamer B), 2.04 (s, 3H, rotamer A), 1.94-1.53 (m, 6H, rotamers A and B) ppm; ESI MS m/z 360 [M−H]⁻.

(+/−)-[2-(3-Ethoxybenzyl)piperidin-1-yl](3-hydroxyquinoxalin-2-yl)methanone (1-78)

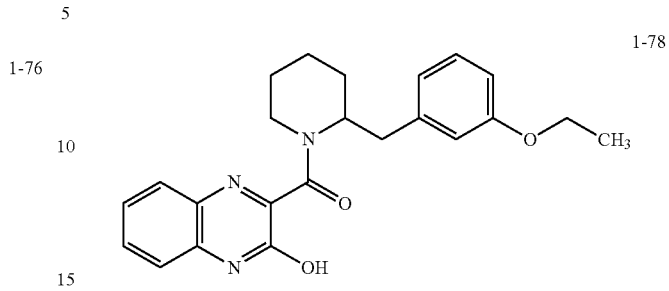

Brown solid: ¹H NMR (400 MHz, CDCl₃, ~1:1 mixture of rotamers) δ 12.50 (s, 1H rotamers A and B), 7.86 (dd, J=8.0, 2.6 Hz, 1H rotamers A and B), 7.64-7.48 (m, 1H rotamers A and B), 7.47-7.30 (m, 2H rotamers A and B), 7.23 (d, J=7.7 Hz, 1H, rotamer A), 7.01 (t, J=7.9 Hz, 1H, rotamer B), 6.96-6.85 (m, 1H rotamers A and B), 6.84-6.72 (m, 1H, rotamer B), 6.60 (dd, J=8.2, 2.0 Hz, 1H, rotamer A), 6.50 (d, J=7.5 Hz, 1H, rotamer B), 6.37 (s, 1H, rotamer A), 5.14 (s, 1H, rotamer B), 4.79 (d, J=11.0 Hz, 1H, rotamer A), 4.07 (q, J=7.0 Hz, 1H, rotamer A), 3.91-3.73 (m, 1H, rotamer B), 3.73-3.55 (m, 1H, rotamer A), 3.53-3.24 (m, 1H, rotamer B), 3.23-2.95 (m, 4H rotamers A and B), 1.97-1.47 (m, 6H, rotamers A and B), 1.41 (t, J=7.0 Hz, 3H, rotamer B), 1.21 (t, J=7.0 Hz, 3H rotamer A) ppm; ESI MS m/z 390 [M−H]⁻.

(+/−)-[2-(4-Fluorobenzyl)piperidin-1-yl](3-hydroxyquinoxalin-2-yl)methanone (1-79)

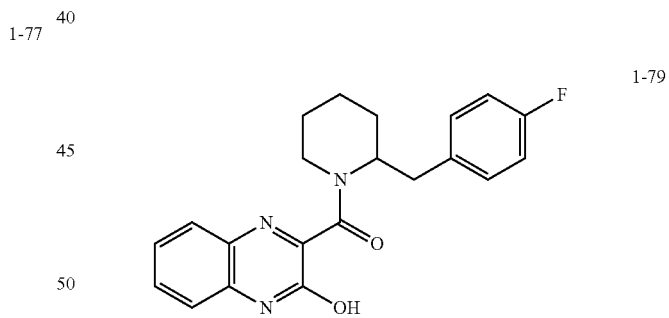

Orange solid: ¹H NMR (400 MHz, CDCl₃, ~1:1 mixture of rotamers) δ 12.30 (s, 1H, rotamers A and B), 7.87 (dd, 1H, rotamer A), 7.81 (dd, 1H, rotamer B), 7.59-7.51 (m, 1H, rotamers A and B), 7.42-7.29 (m, 3H, rotamers A and B), 7.08-6.99 (m, 1H, rotamers A and B), 6.92-6.84 (m, 1H, rotamers A and B), 6.84-6.74 (m, 1H rotamers A and B), 5.10 (s, 1H, rotamer A), 4.80 (d, 1H, rotamer B), 3.79 (s, 1H, rotamer A), 3.50-3.25 (m, 1H, rotamers A and B), 3.16 (dd, 1H, rotamer B), 3.12-2.89 (m, 2H, rotamers A and B), 1.95-1.51 (m, 6H, rotamers A and B) ppm; ESI MS m/z 366 [M+H]⁺.

(+/−)-(3-Hydroxyquinoxalin-2-yl)[2-(4-methoxybenzyl)piperidin-1-yl]methanone (1-80)

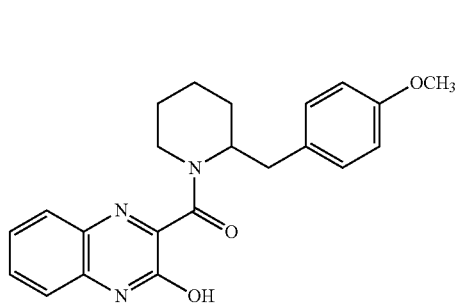

1-80

Yellow solid: $^1$H NMR (400 MHz, CDCl$_3$, ~1:1 mixture of rotamers) δ 12.58 (s, 1H, rotamers A and B), 7.92-7.79 (m, 1H, rotamers A and B), 7.60-7.49 (m, 1H, rotamers A and B), 7.43-7.32 (m, 2H, rotamers A and B), 7.32-7.22 (m, 1H, rotamers A and B), 6.95-6.85 (m, 1H, rotamers A and B), 6.83 (d, J=8.6 Hz, 1H, rotamers A and B), 6.70-6.57 (m, 1H, rotamers A and B), 5.18-5.04 (m, 1H, rotamer A), 4.80 (d, J=11.7 Hz, 1H, rotamer B), 3.79 (s, 3H, rotamer A), 3.65 (s, 3H, rotamer B), 3.50-3.28 (m, 1H, rotamers A and B), 3.16-2.91 (m, 3H, rotamers A and B), 1.93-1.54 (m, 6H, rotamers A and B) ppm; ESI MS m/z 376 [M−H]$^-$.

(+/−)-[2-(3-Fluoro-4-methoxybenzyl)piperidin-1-yl](3-hydroxyquinoxalin-2-yl)methanone (1-81)

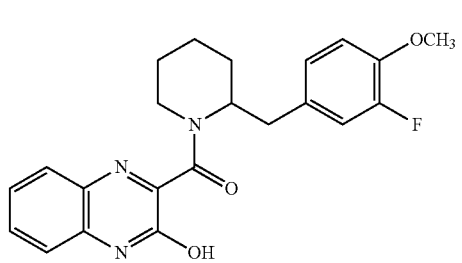

1-81

Yellow solid: $^1$H NMR (400 MHz, CDCl$_3$, ~1:1 mixture of rotamers) δ 12.40 (s, 1H, rotamers A and B), 7.92-7.78 (m, 1H, rotamers A and B), 7.60-7.50 (m, 1H, rotamers A and B), 7.45-7.31 (m, 2H, rotamers A and B), 7.15-7.02 (m, 1H, rotamers A and B), 6.98-6.88 (m, 1H, rotamer A), 6.74-6.68 (m, 1H, rotamer B), 6.68-6.59 (m, 1H, rotamers A and B), 5.15-5.04 (m, 1H, rotamer A), 4.79 (d, J=13.3 Hz, 1H, rotamer B), 3.87 (s, 3H, rotamer A), 3.85-3.76 (m, 1H, rotamer A), 3.74 (s, 3H, rotamer B), 3.49-3.27 (m, 1H, rotamers A and B), 3.16-2.88 (m, 2H, rotamers A and B and 1H, rotamer B), 1.91-1.54 (m, 6H, rotamers A and B) ppm; ESI MS m/z 394 [M−H]$^-$.

(+/−)-(3-Benzylmorpholino)(3-hydroxyquinoxalin-2-yl)methanone (1-82)

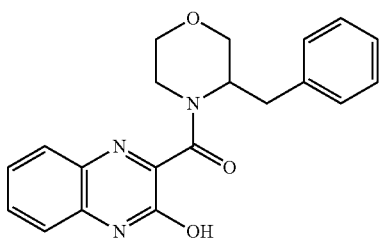

1-82

Yellow solid: $^1$H NMR (400 MHz, CDCl$_3$, ~1:1 mixture of rotamers) δ 12.40 (s, 1H, rotamers A and B), 7.94-7.83 (m, 1H, rotamers A and B), 7.67-7.49 (m, 1H, rotamers A and B), 7.47-7.32 (m, 4H, rotamers A and B), 7.18-7.02 (m, 2H, rotamers A and B), 7.01-6.88 (m, 1H, rotamers A and B), 4.86-4.76 (m, 1H, rotamer A), 4.60 (dd, J=13.7, 2.3 Hz, 1H, rotamer B), 4.10 (dd, J=11.6, 3.7 Hz, 1H, rotamer A), 3.94-3.78 (m, 1H, rotamers A and B), 3.78-3.52 (m, 4H, rotamers A and B), 3.43 (td, J=13.4, 4.0 Hz, 1H, rotamer B), 3.33 (t, J=11.8 Hz, 1H, rotamers A and B), 3.21 (dd, J=13.1, 4.9 Hz, 1H, rotamer A), 3.12 (dd, J=13.0, 4.5 Hz, 1H, rotamer B) ppm; ESI MS m/z 348 [M−H]$^-$.

(+/−)-(3-Benzylpiperidin-1-yl)(3-hydroxyquinoxalin-2-yl)methanone (1-83)

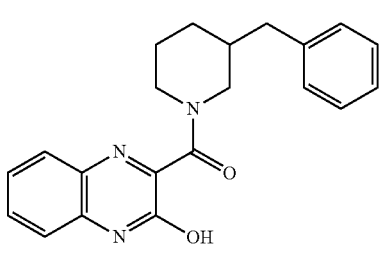

1-83

Yellow solid: $^1$H NMR (400 MHz, CDCl$_3$, ~1:1 mixture of rotamers) δ 12.08 (s, 1H, rotamers A and B), 7.87 (d, 1H, rotamer A), 7.82 (dd, 1H, rotamer B), 7.60-7.48 (m, 1H, rotamers A and B), 7.43-7.28 (m, 3H, rotamers A and B), 7.25-7.17 (m, 2H, rotamers A and B), 6.96-6.83 (m, 2H, rotamers A and B), 4.65 (d, 1H, rotamer A), 4.57 (dd, 1H, rotamer B), 3.50 (d, 1H, rotamer A), 3.35 (d, 1H, rotamer B), 3.23-3.11 (m, 1H, rotamer A), 3.01-2.81 (m, 1H, rotamers A and B), 2.81-2.73 (m, 1H, rotamer B), 2.61-2.50 (m, 1H, rotamers A and B), 2.32 (dd, 1H, rotamer A), 2.10-1.97 (m, 1H, rotamer B), 1.97-1.50 (m, 3H, rotamers A and B), 1.39-1.16 (m, 2H, rotamers A and B) ppm; ESI MS m/z 348 [M+H]$^+$.

(+/−)-(3-Hydroxyquinoxalin-2-yl)[3-(2-methylbenzyl)piperidin-1-yl]methanone (1-84)

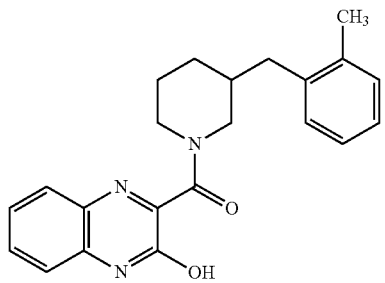

Orange solid: $^1$H NMR (400 MHz, CDCl$_3$, ~1:1 mixture of rotamers) δ 7.91-7.76 (m, 1H rotamers A and B), 7.58-7.48 (m, 1H rotamers A and B), 7.42-7.30 (m, 2H rotamers A and B), 7.23-7.09 (m, 2H rotamers A and B), 6.87-6.64 (m, 2H rotamers A and B), 4.77-4.52 (m, 1H rotamers A and B), 3.56-3.34 (m, 1H rotamers A and B), 3.24-3.11 (m, 1H, rotamer A), 2.99-2.74 (m, 2H rotamers A and B and 1H, rotamer B), 2.64-2.44 (m, 1H rotamers A and B), 2.40-2.26 (m, 1H rotamers A and B), 2.37 (s, 3H, rotamer A), 2.12 (s, 3H, rotamer B), 2.07-1.48 (m, 4H rotamers A and B), 1.43-1.21 (m, 1H, rotamers A and B) ppm; ESI MS m/z 360 [M−H]$^-$.

(+/−)-(3-Hydroxyquinoxalin-2-yl)[3-(3-methoxybenzyl)piperidin-1-yl]methanone (1-85)

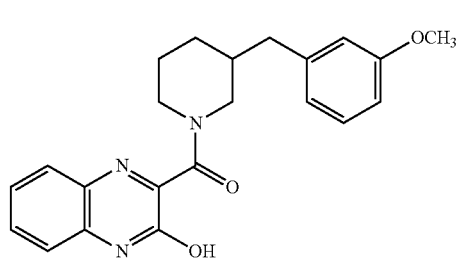

Brown solid: $^1$H NMR (400 MHz, CDCl$_3$, ~1:1 mixture of rotamers) δ 12.28 (s, 1H, rotamers A and B), 7.86 (dd, J=8.4, 1.3 Hz, 1H, rotamer A), 7.80 (dd, J=8.1, 1.0 Hz, 1H, rotamer B), 7.60-7.47 (m, 1H, rotamers A and B), 7.44-7.28 (m, 2H, rotamers A and B), 7.25-7.16 (m, 1H, rotamers A and B), 6.87-6.74 (m, 2H, rotamers A and B), 6.55-6.47 (m, 1H, rotamer A), 6.44 (dd, J=8.2, 1.9 Hz, 1H, rotamer B), 4.65 (d, J=12.9 Hz, 1H, rotamer A), 4.55 (dd, J=12.9, 3.6 Hz, 1H, rotamer B), 3.82 (s, 3H, rotamer B), 3.59 (s, 3H, rotamer A), 3.50 (d, J=13.4 Hz, 1H, rotamer B), 3.38 (d, J=11.7 Hz, 1H, rotamer A), 3.24-3.10 (m, 1H, rotamer A), 3.00-2.87 (m, 1H, rotamers A and B), 2.87-2.73 (m, 1H, rotamers A and B), 2.52 (dd, J=14.1, 7.2 Hz, 1H, rotamers A and B), 2.29 (dd, J=13.8, 8.6 Hz, 1H, rotamer B), 2.11-1.51 (m, 3H, rotamers A and B), 1.45-0.75 (m, 2H, rotamers A and B) ppm; ESI MS m/z 376 [M−H]$^-$.

(+/−)-[3-(3-Fluorobenzyl)piperidin-1-yl](3-hydroxyquinoxalin-2-yl)methanone (1-86)

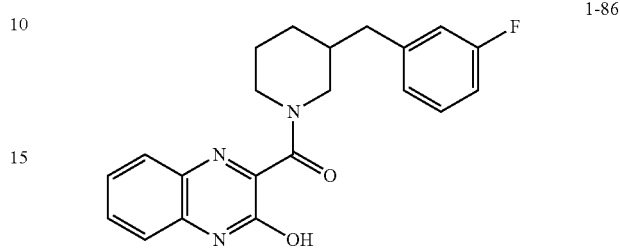

Brown solid: $^1$H NMR (400 MHz, CDCl$_3$, ~1:1 mixture of rotamers) δ 12.39 (s, 1H, rotamers A and B), 7.86 (dd, J=8.0, 1.0 Hz, 1H, rotamer A), 7.80 (dd, J=8.1, 1.0 Hz, 1H, rotamer B), 7.62-7.45 (m, 1H, rotamers A and B), 7.45-7.31 (m, 2H, rotamers A and B), 7.30-7.19 (m, 1H, rotamer A), 7.08-6.78 (m, 2H, rotamers A and B), 6.77-6.62 (m, 1H, rotamers A and B), 6.58 (td, J=8.4, 2.2 Hz, 1H, rotamer B), 4.64 (d, J=12.9 Hz, 1H, rotamer A), 4.52 (dd, J=12.9, 3.6 Hz, 1H, rotamer B), 3.50 (dt, J=13.1, 3.5 Hz, 1H, rotamer A), 3.43-3.30 (m, 1H, rotamer B), 3.25-3.13 (m, 1H, rotamer A), 2.99-2.75 (m, 2H, rotamers A and B), 2.64-2.50 (m, 1H, rotamers A and B), 2.33 (dd, J=13.9, 8.5 Hz, 1H, rotamer B), 2.12-1.51 (m, 3H, rotamers A and B), 1.38-1.19 (m, 2H, rotamers A and B) ppm; ESI MS m/z 364 [M−H]$^-$.

(+/−)-(3-Hydroxyquinoxalin-2-yl)[3-(3-methylbenzyl)piperidin-1-yl]methanone (1-87)

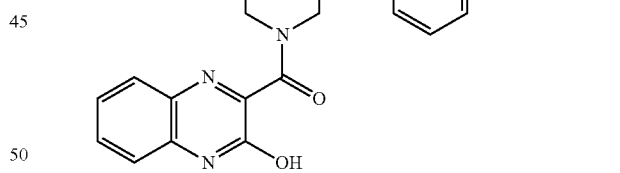

Orange solid: $^1$H NMR (400 MHz, CDCl$_3$, ~1:1 mixture of rotamers) δ 7.92-7.76 (m, 1H, rotamers A and B), 7.59-7.48 (m, 1H, rotamers A and B), 7.43-7.31 (m, 2H, rotamers A and B), 7.20 (t, J=7.7 Hz, 1H, rotamer A), 7.07-6.94 (m, 1H, rotamers A and B and 1H, rotamer B), 6.84-6.68 (m, 2H, rotamers A and B), 4.73-4.52 (m, 1H, rotamers A and B), 3.45 (dd, J=38.1, 13.5 Hz, 1H, rotamers A and B), 3.24-3.08 (m, 1H, rotamer A), 3.03-2.74 (m, 2H, rotamers A and B and 1H, rotamer B), 2.58-2.43 (m, 1H, rotamers A and B), 2.41-2.22 (m, 2H, rotamers A and B), 2.33 (s, 3H, rotamer A), 1.83 (s, 3H, rotamer B), 2.10-1.51 (m, 4H, rotamers A and B), 1.38-1.15 (m, 1H, rotamers A and B) ppm; ESI MS m/z 360 [M−H]$^-$.

(+/−)-[3-(4-Fluorobenzyl)piperidin-1-yl](3-hydroxyquinoxalin-2-yl)methanone (1-88)

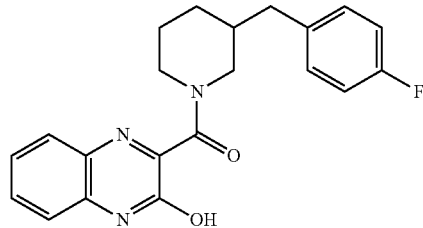

Brown solid: $^1$H NMR (400 MHz, CDCl$_3$, ~1:1 mixture of rotamers) δ 12.08 (s, 1H, rotamers A and B), 7.90-7.84 (m, 1H, rotamer A), 7.80 (dd, J=8.1, 1.2 Hz, 1H, rotamer B), 7.60-7.47 (m, 1H, rotamers A and B), 7.45-7.29 (m, 2H, rotamers A and B), 7.22-7.13 (m, 1H, rotamers A and B), 7.06-6.94 (m, 1H, rotamers A and B), 6.93-6.84 (m, 1H, rotamers A and B), 6.70-6.52 (m, 1H, rotamers A and B), 4.64 (d, J=13.4 Hz, 1H, rotamer A), 4.50 (dd, J=13.0, 3.7 Hz, 1H, rotamer B), 3.50 (dt, J=13.1, 3.5 Hz, 1H, rotamer A), 3.34 (d, J=13.2 Hz, 1H, rotamer B), 3.26-3.11 (m, 1H, rotamer A), 3.01-2.84 (m, 2H, rotamers A and B), 2.84-2.71 (m, 1H, rotamers A and B), 2.60-2.45 (m, 1H, rotamers A and B), 2.30 (dd, J=13.9, 8.5 Hz, 1H, rotamer B), 2.06-1.51 (m, 3H, rotamers A and B), 1.40-1.15 (m, 1H, rotamers A and B) ppm; ESI MS m/z 364 [M−H]$^−$.

(4-Benzylpiperidin-1-yl)(3-hydroxyquinoxalin-2-yl)methanone (1-89)

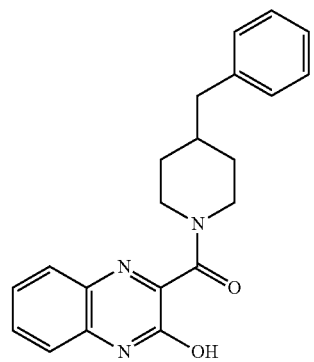

Yellow solid: $^1$H NMR (400 MHz, CDCl$_3$) δ 12.26 (s, 1H), 7.88 (d, 1H), 7.56 (t, 1H), 7.41-7.35 (m, 2H), 7.29 (t, 2H), 7.19 (t, 1H), 7.13 (d, 2H), 4.78 (d, 1H), 3.57 (d, 1H), 3.11 (t, 1H), 2.82 (t, 1H), 2.62-2.55 (m, 2H), 1.83 (d, 2H), 1.64 (d, 1H), 1.48-1.34 (m, 2H) ppm; ESI MS m/z 346 [M−H]$^−$.

[3-Benzyltetrahydropyrimidin-1(2H)-yl](3-hydroxyquinoxalin-2-yl)methanone (1-90)

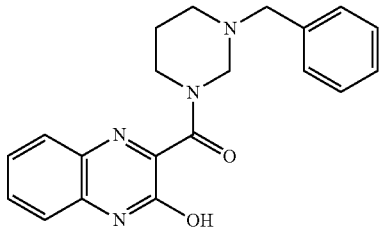

Orange solid: $^1$H NMR (400 MHz, CDCl$_3$, ~1:1 mixture of rotamers) δ 12.42 (s, 1H, rotamers A and B), 7.94-7.78 (m, 1H, rotamers A and B), 7.58-7.47 (m, 1H, rotamers A and B), 7.47-7.27 (m, 4H, rotamers A and B), 7.17-7.04 (m, 1H, rotamers A and B), 6.98-6.83 (m, 2H, rotamers A and B), 4.66 (s, 1H, rotamers A and B), 4.04 (s, 1H, rotamers A and B), 3.94 (s, 2H, rotamers A and B), 3.59 (s, 1H, rotamers A and B), 3.56-3.47 (m, 1H, rotamers A and B), 2.96-2.82 (m, 2H, rotamers A and B), 1.96-1.82 (m, 1H, rotamers A and B), 1.79-1.73 (m, 1H, rotamers A and B) ppm; ESI MS m/z 347 [M−H]$^−$.

(+/−)-(3-Hydroxyquinoxalin-2-yl)[2-(3-methylbenzyl)azepan-1-yl]methanone (1-91)

Red-brown solid: $^1$H NMR (400 MHz, CDCl$_3$, ~2:1 mixture of rotamers) δ 12.21 (s, 1H, rotamers A and B), 7.92-7.79 (m, 1H, rotamers A and B), 7.61-7.49 (m, 1H, rotamers A and B), 7.43-7.29 (m, 2H, rotamers A and B), 7.22-7.09 (m, 1H, rotamers A and B), 7.06-6.84 (m, 3H, rotamers A and B), 4.90-4.75 (m, 1H, rotamer B), 4.39 (d, J=13.5 Hz, 1H, rotamer A), 3.86 (s, 1H, rotamer A), 3.53 (d, J=15.4 Hz, 1H, rotamer B), 3.29 (dd, J=13.1, 4.0 Hz, 1H, rotamer B), 3.24-3.10 (m, 1H, rotamer B), 3.10-3.00 (m, 1H, rotamer A), 2.94 (t, J=11.9 Hz, 1H, rotamer A), 2.88-2.68 (m, 1H, rotamers A and B), 2.08-1.90 (m, 2H, rotamers A and B), 1.87-1.55 (m, 4H, rotamers A and B), 1.83 (s, 3H, rotamers A and B), 1.55-1.12 (m, 6H, rotamers A and B) ppm; ESI MS m/z 374 [M−H]$^−$.

(+/−)-(6,7-Dichloro-3-hydroxyquinoxalin-2-yl)[2-(3-methylbenzyl)azepan-1-yl]methanone (1-92)

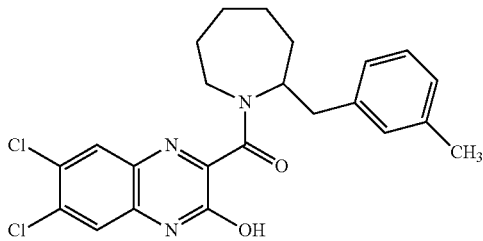

1-92

Brown solid: ¹H NMR (400 MHz, CDCl₃, ~2:1 mixture of rotamers) δ 7.95 (s, 1H, rotamer B), 7.85 (s, 1H, rotamer A), 7.47 (s, 1H, rotamer B), 7.45 (s, 1H, rotamer A), 7.29-7.26 (m, 1H, rotamer B), 7.18-7.11 (m, 2H, rotamer A), 7.02-6.92 (m, 2H, rotamers A and B), 6.85 (d, J=7.2 Hz, 1H, rotamer B), 4.83-4.75 (m, 1H, rotamer B), 4.35 (d, J=13.4 Hz, 1H, rotamer A), 3.87-3.78 (m, 1H, rotamer A), 3.51-3.45 (m, 1H, rotamer B), 3.25-3.12 (m, 2H, rotamer B), 2.98-2.90 (m, 2H, rotamer A), 2.81 (s, 3H, rotamer A), 2.79-2.70 (m, 1H, rotamers A and B), 2.50 (s, 3H, rotamer B), 2.02-1.19 (m, 6H, rotamers A and B) ppm; ESI MS m/z 444 [M+H]⁺.

(+/−)-[2-(4-Chlorobenzyl)azepan-1-yl](3-hydroxyquinoxalin-2-yl)methanone (1-93)

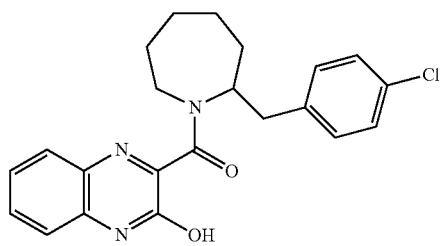

1-93

Orange solid: ¹H NMR (400 MHz, CDCl₃, ~2:1 mixture of rotamers) δ 12.33 (s, 1H, rotamers A and B), 7.88 (dd, 1H, rotamer B), 7.84 (dd, 1H, rotamer A), 7.60-7.50 (m, 1H, rotamers A and B), 7.43-7.27 (m, 4H, rotamers A and B), 7.11-7.05 (m, 1H, rotamers A and B), 6.85 (d, 1H, rotamers A and B), 4.81-4.67 (m, 1H, rotamer B), 4.34 (d, 1H, rotamer A), 3.69 (s, 1H, rotamer A), 3.36 (d, 1H, rotamer B), 3.09-2.92 (m, 1H, rotamers A and B), 2.89-2.64 (m, 2H, rotamers A and B), 2.07-1.07 (m, 8H, rotamers A and B) ppm; ESI MS m/z 396 [M+H]⁺.

(+/−)-(3-Benzylazepan-1-yl)(3-hydroxyquinoxalin-2-yl)methanone (1-94)

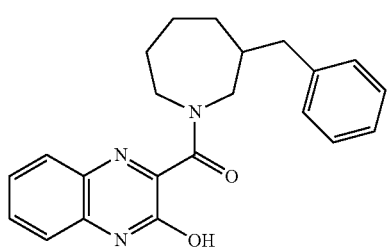

1-94

Yellow solid: ¹H NMR (400 MHz, CDCl₃, ~2:1 mixture of rotamers) δ 12.08 (s, 1H, rotamers A and B), 7.88 (d, 1H, rotamer B), 7.77 (d, 1H, rotamer A), 7.54 (q, 1H, rotamers A and B), 7.39 (t, 1H, rotamers A and B), 7.35-7.22 (m, 3H, rotamers A and B), 6.73 (d, 1H, rotamers A and B), 6.67 (d, 2H, rotamers A and B), 4.27-4.19 (m, 1H, rotamer A), 4.18-4.13 (m, 1H, rotamer B), 3.53 (dd, 1H, rotamer A), 3.44 (t, 1H, rotamers A and B), 3.04 (dd, 1H, rotamer B), 3.22 (dd, 1H, rotamer B), 2.92 (dd, 1H, rotamer A), 2.86 (dd, 1H, rotamer B), 2.59 (dd, 1H, rotamer B), 2.51 (dd, 1H, rotamer A), 2.41-2.32 (m, 1H, rotamer B), 2.20-2.11 (m, 1H, rotamer A), 2.12 (dd, 1H, rotamer A), 2.05-1.90 (m, 2H, rotamers A and B), 1.86-1.54 (m, 3H, rotamers A and B), 1.37-1.22 (m, 2H, rotamers A and B) ppm; ESI MS m/z 360 [M−H]⁻.

(+/−)-(2-Benzylazetidin-1-yl)(3-hydroxyquinoxalin-2-yl)methanone (1-95)

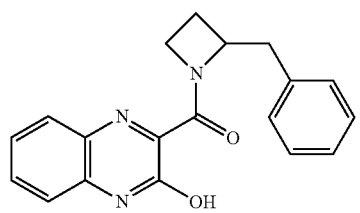

1-95

Brown solid: ¹H NMR (400 MHz, CDCl₃, ~2:1 mixture of rotamers) δ 7.91-7.85 (m, 1H, rotamers A and B), 7.67-7.55 (m, 1H, rotamers A and B and 1H, rotamer A), 7.49-7.40 (m, 1H, rotamers A and B and 1H, rotamer B), 7.34 (s, 1H, rotamers A and B), 7.32 (s, 1H, rotamers A and B), 7.28-7.23 (m, 1H, rotamers A and B), 7.13-7.02 (m, 2H, rotamers A and B), 5.26-5.16 (m, 1H, rotamer B), 4.99-4.91 (m, 1H, rotamer A), 4.28-4.21 (m, 2H, rotamer A), 4.12-4.04 (m, 2H, rotamer B), 3.50 (d, J=13.4 Hz, 1H, rotamer A), 3.28-3.21 (m, 1H, rotamer A), 3.08-3.00 (m, 2H, rotamer B), 2.62-2.51 (m, 1H, rotamer B), 2.44-2.34 (m, 1H, rotamer A), 2.15-2.03 (m, 1H, rotamers A and B) ppm; ESI MS m/z 320 [M+H]⁺.

[3-(4-Fluorobenzyl)azetidin-1-yl](3-hydroxyquinoxalin-2-yl)methanone (1-96)

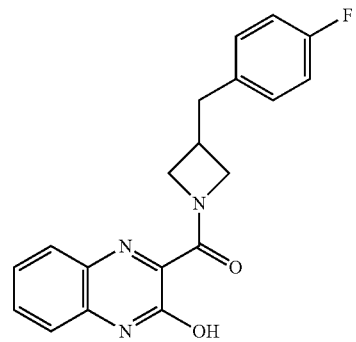

1-96

Yellow solid: ¹H NMR (400 MHz, CDCl₃) δ 7.89 (d, 1H), 7.65 (t, 1H), 7.57 (s, 1H), 7.45 (t, 1H), 7.17-7.09 (m, 2H), 6.99 (t, 2H), 4.44-4.34 (m, 2H), 4.02 (dd, 2H), 3.16-2.90 (m, 3H) ppm; ESI MS m/z 336 [M−H]⁻.

The following examples were prepared using General Method 1 as described above:

TABLE 1-1

| ID | Structure | MW | FABP4 TdF Kd uM |
|---|---|---|---|
| 1-2 | 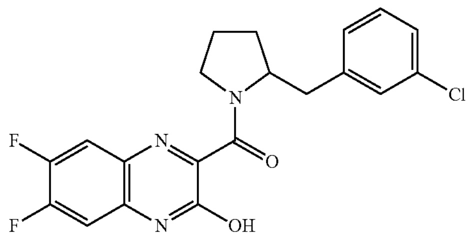 [SMILES: O=C(c1nc2cc(F)c(F)cc2nc1O)N1CCCC1Cc1cccc(Cl)c1] | 403.82 | 0.08 |
| 1-3 | 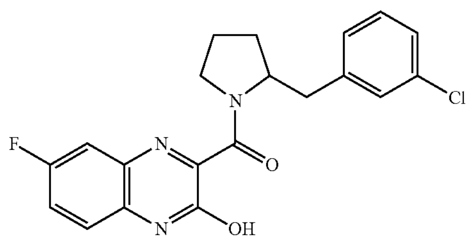 [SMILES: O=C(c1nc2cc(F)ccc2nc1O)N1CCCC1Cc1cccc(Cl)c1] | 385.83 | 0.3 |
| 1-4 | 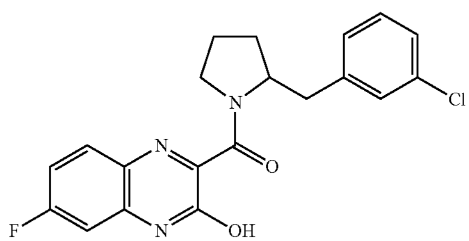 [SMILES: O=C(c1nc2ccc(F)cc2nc1O)N1CCCC1Cc1cccc(Cl)c1] | 385.83 | 0.18 |
| 1-5 | 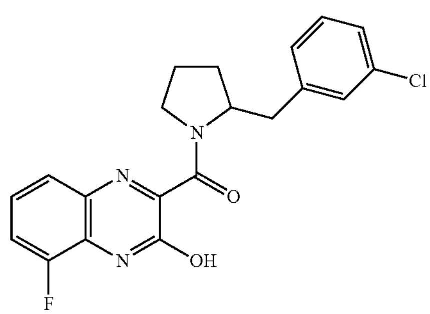 [SMILES: O=C(c1nc2cccc(F)c2nc1O)N1CCCC1Cc1cccc(Cl)c1] | 385.83 | |
| 1-6 | 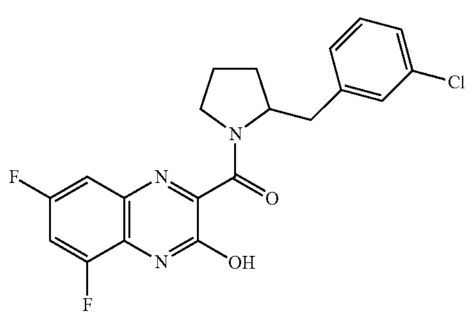 [SMILES: O=C(c1nc2cc(F)cc(F)c2nc1O)N1CCCC1Cc1cccc(Cl)c1] | 403.82 | |

TABLE 1-1-continued
| ID | Structure | MW | FABP4 TdF Kd uM |
|---|---|---|---|
| 1-7 | 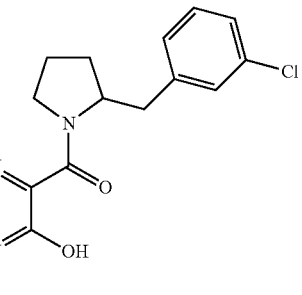 | 403.82 | |
| 1-8 | 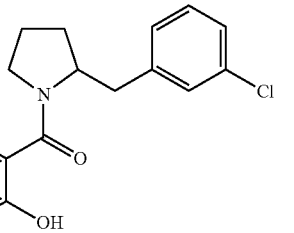 | 402.28 | 0.11 |
| 1-9 | 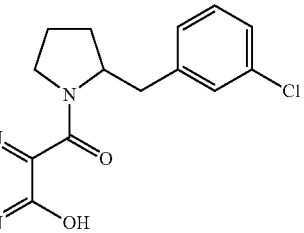 | 402.28 | 0.41 |
| 1-10 | 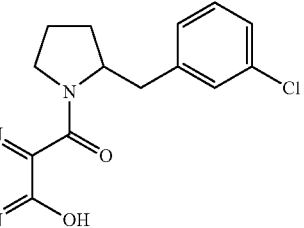 | 402.28 | 0.25 |
| 1-11 | 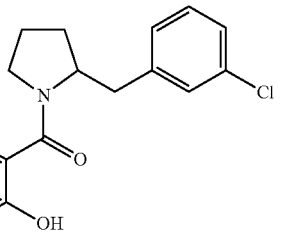 | 402.28 | 0.003 |

TABLE 1-1-continued

| ID | Structure | MW | FABP4 TdF Kd uM |
|---|---|---|---|
| 1-12 | 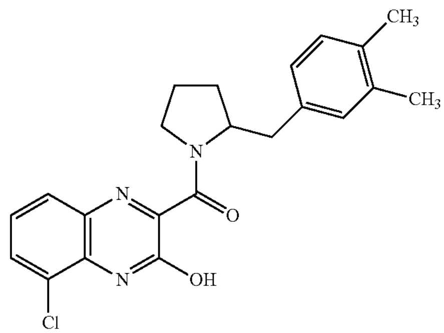 [SMILES: Cc1ccc(CC2CCCN2C(=O)c2nc3cccc(Cl)c3nc2O)cc1C] | 395.89 | |
| 1-13 | 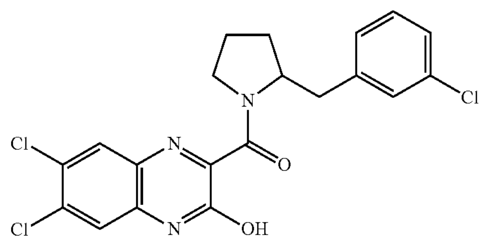 [SMILES: O=C(c1nc2cc(Cl)c(Cl)cc2nc1O)N1CCCC1Cc1cccc(Cl)c1] | 436.73 | 0.063 |
| 1-14 | 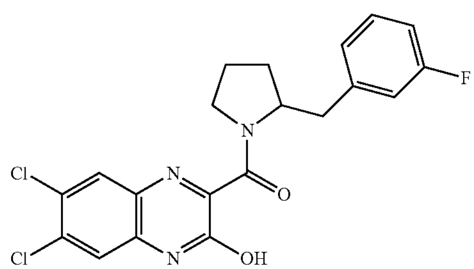 [SMILES: O=C(c1nc2cc(Cl)c(Cl)cc2nc1O)N1CCCC1Cc1cccc(F)c1] | 420.27 | |
| 1-15 | 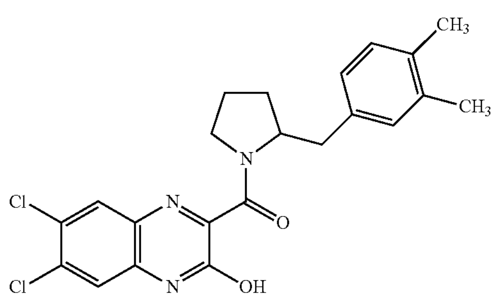 [SMILES: Cc1ccc(CC2CCCN2C(=O)c2nc3cc(Cl)c(Cl)cc3nc2O)cc1C] | 430.34 | |
| 1-16 | 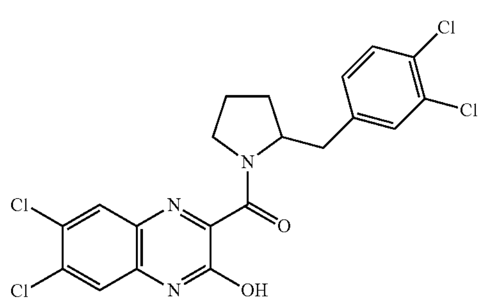 [SMILES: O=C(c1nc2cc(Cl)c(Cl)cc2nc1O)N1CCCC1Cc1ccc(Cl)c(Cl)c1] | 471.17 | |

TABLE 1-1-continued

| ID | Structure | MW | FABP4 TdF Kd uM |
|---|---|---|---|
| 1-17 | 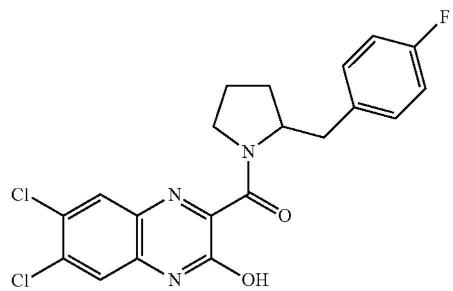 [SMILES: O=C(c1nc2cc(Cl)c(Cl)cc2nc1O)N1CCCC1Cc1ccc(F)cc1] | 420.27 | |
| 1-18 | 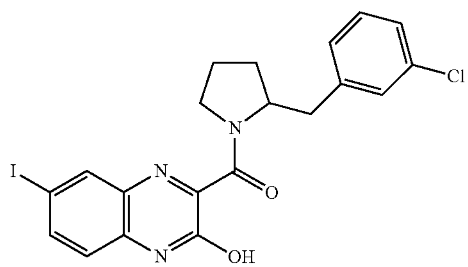 [SMILES: O=C(c1nc2cc(I)ccc2nc1O)N1CCCC1Cc1cccc(Cl)c1] | 493.73 | 0.63 |
| 1-19 | 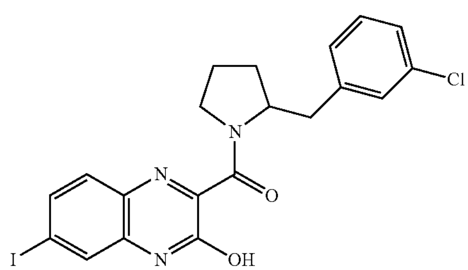 [SMILES: O=C(c1nc2ccc(I)cc2nc1O)N1CCCC1Cc1cccc(Cl)c1] | 493.73 | 0.46 |
| 1-20 | 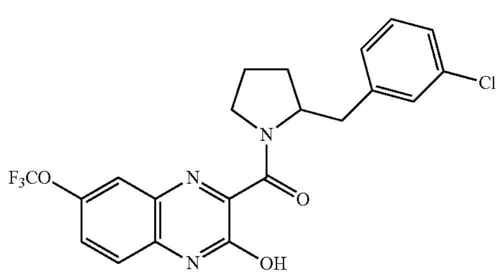 | 451.84 | 0.95 |
| 1-21 | 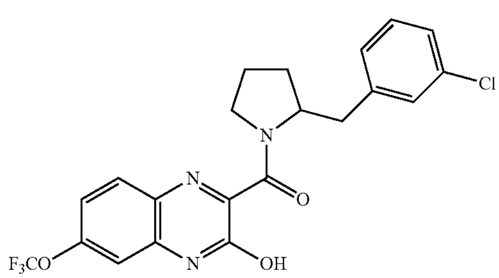 | 451.84 | 0.22 |

TABLE 1-1-continued

| ID | Structure | MW | FABP4 TdF Kd uM |
|---|---|---|---|
| 1-22 | 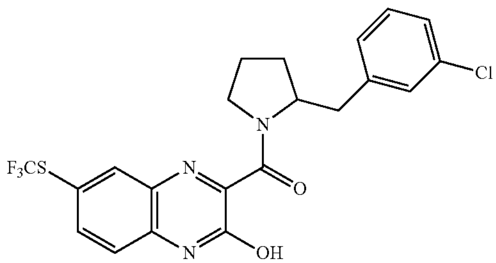 | 467.90 | 0.024 |
| 1-23 | 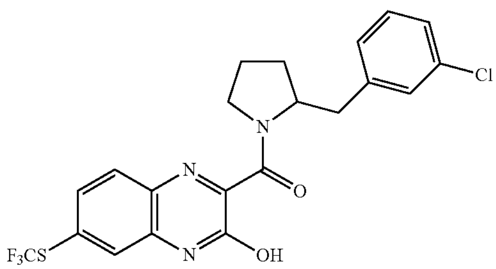 | 467.90 | 0.024 |
| 1-24 | 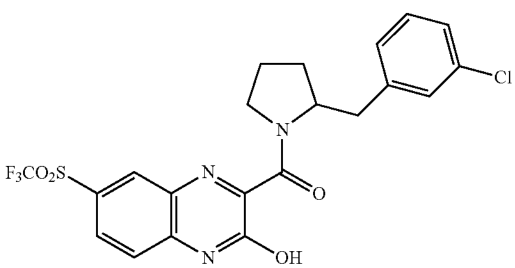 | 499.90 | 0.3 |
| 1-25 | 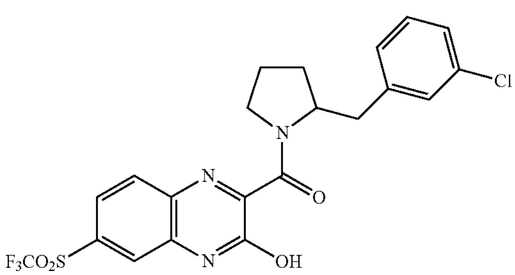 | 499.90 | 0.1 |
| 1-26 | 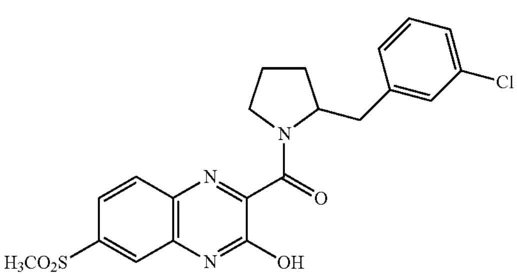 | 445.93 | |

TABLE 1-1-continued

| ID | Structure | MW | FABP4 TdF Kd uM |
|---|---|---|---|
| 1-27 | 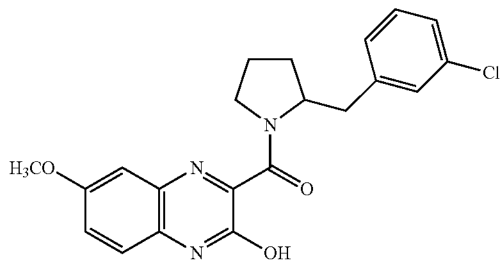 [SMILES: COc1ccc2nc(O)c(C(=O)N3CCCC3Cc3cccc(Cl)c3)nc2c1] | 397.86 | 4.94 |
| 1-28 | 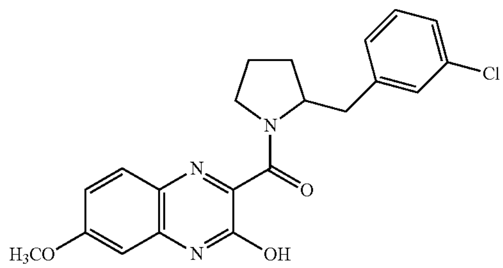 | 397.86 | 50 |
| 1-29 | 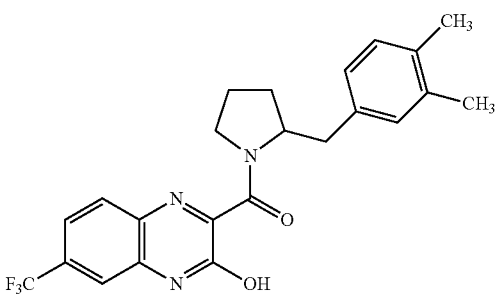 [SMILES: Cc1ccc(CC2CCCN2C(=O)c2nc3ccc(C(F)(F)F)cc3nc2O)cc1C] | 429.45 | |
| 1-30 | 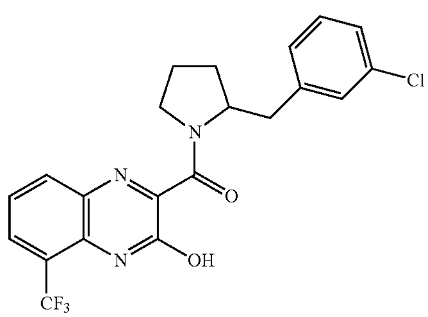 [SMILES: O=C(c1nc2cccc(C(F)(F)F)c2nc1O)N1CCCC1Cc1cccc(Cl)c1] | 435.84 | 0.002 |
| 1-31 | 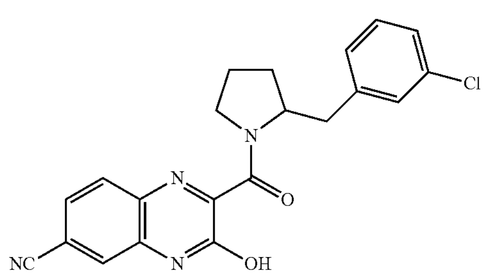 [SMILES: N#Cc1ccc2nc(C(=O)N3CCCC3Cc3cccc(Cl)c3)c(O)nc2c1] | 392.85 | 0.5 |

TABLE 1-1-continued
| ID | Structure | MW | FABP4 TdF Kd uM |
|---|---|---|---|
| 1-32 | 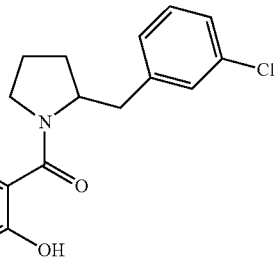 | 368.83 | 0.3 |
| 1-33 | 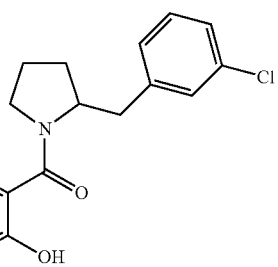 | 368.83 | 0.6 |
| 1-34 | 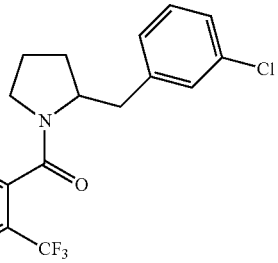 | 419.84 | |
| 1-35 | 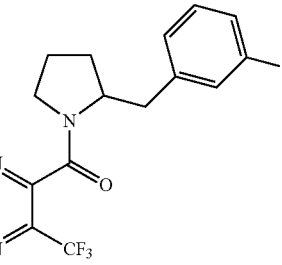 | 488.73 | 50 |
| 1-36 | 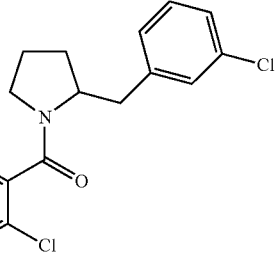 | 386.28 | 50 |

TABLE 1-1-continued

| ID | Structure | MW | FABP4 TdF Kd uM |
|---|---|---|---|
| 1-37 | 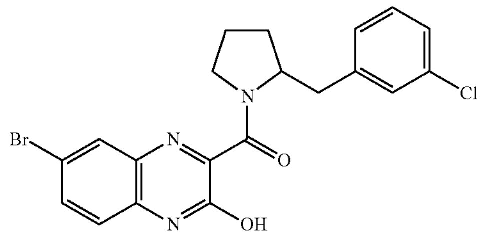 | 446.73 | 0.85 |
| 1-38 | 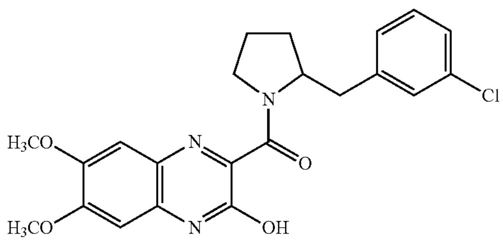 [SMILES: COc1cc2nc(O)c(C(=O)N3CCCC3Cc3cccc(Cl)c3)nc2cc1OC] | 427.89 | 22.46 |
| 1-39 | 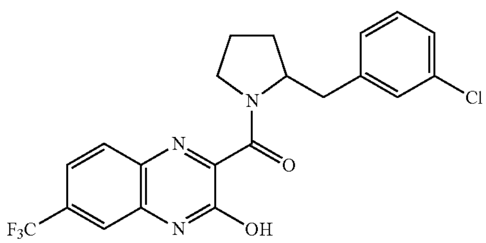 [SMILES: O=C(c1nc2ccc(C(F)(F)F)cc2nc1O)N1CCCC1Cc1cccc(Cl)c1] | 435.84 | 0.2 |
| 1-40 | 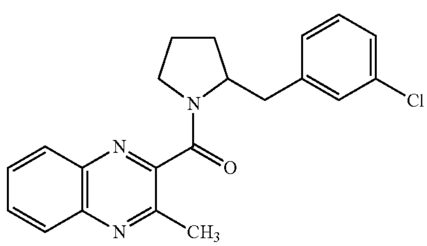 [SMILES: Cc1nc2ccccc2nc1C(=O)N1CCCC1Cc1cccc(Cl)c1] | 365.87 | 50 |
| 1-41 | 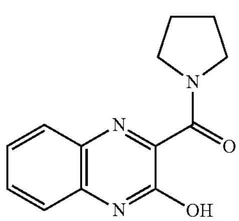 [SMILES: O=C(c1nc2ccccc2nc1O)N1CCCC1] | 243.27 | 50 |
| 1-42 | 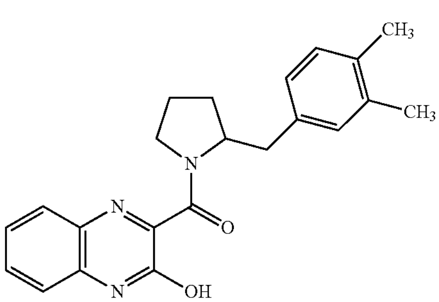 [SMILES: Cc1ccc(CC2CCCN2C(=O)c2nc3ccccc3nc2O)cc1C] | 361.45 | 1.34 |

TABLE 1-1-continued

| ID | Structure | MW | FABP4 TdF Kd uM |
|---|---|---|---|
| 1-43 | 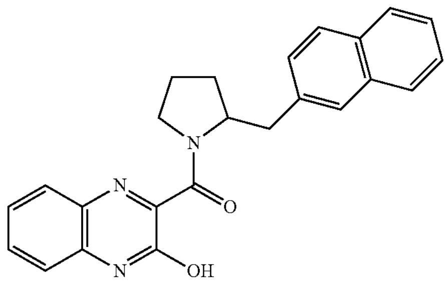 [SMILES: O=C(c1nc2ccccc2nc1O)N1CCCC1Cc1ccc2ccccc2c1] | 383.45 | |
| 1-44 | 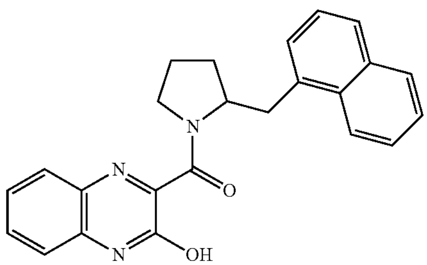 [SMILES: O=C(c1nc2ccccc2nc1O)N1CCCC1Cc1cccc2ccccc12] | 383.45 | |
| 1-45 | 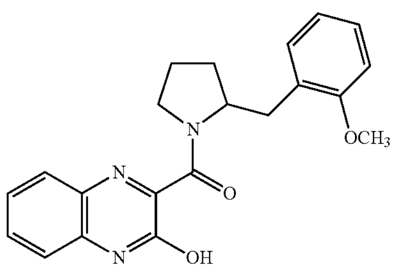 [SMILES: COc1ccccc1CC1CCCN1C(=O)c1nc2ccccc2nc1O] | 363.42 | |
| 1-46 | 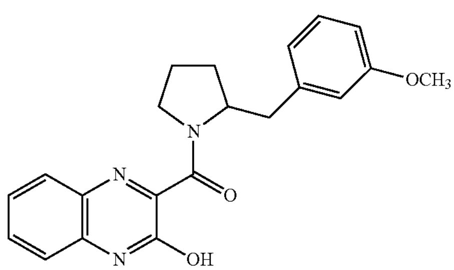 [SMILES: COc1cccc(CC2CCCN2C(=O)c2nc3ccccc3nc2O)c1] | 363.42 | |
| 1-47 | 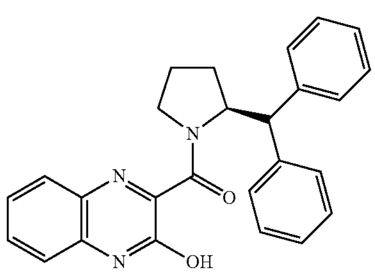 [SMILES: O=C(c1nc2ccccc2nc1O)N1CCC[C@H]1C(c1ccccc1)c1ccccc1] | 409.49 | 50 |

TABLE 1-1-continued

| ID | Structure | MW | FABP4 TdF Kd uM |
|---|---|---|---|
| 1-48 | 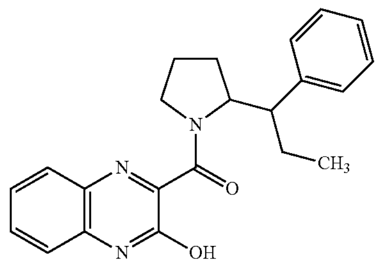 [SMILES: CCC(c1ccccc1)C1CCCN1C(=O)c1nc2ccccc2nc1O] | 361.45 | 11.87 |
| 1-49 | 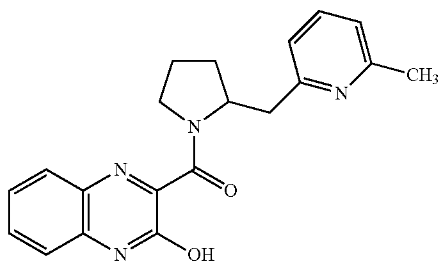 [SMILES: Cc1cccc(CC2CCCN2C(=O)c2nc3ccccc3nc2O)n1] | 348.41 | 50 |
| 1-50 | 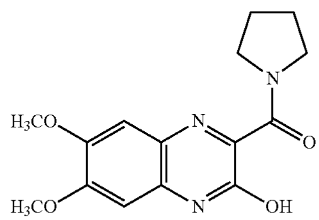 [SMILES: COc1cc2nc(O)c(C(=O)N3CCCC3)nc2cc1OC] | 303.32 | 50 |
| 1-51 | 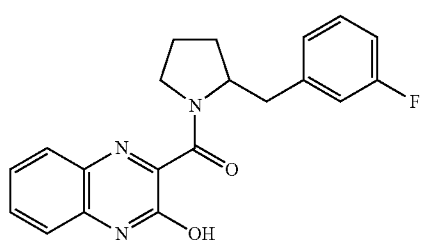 [SMILES: O=C(c1nc2ccccc2nc1O)N1CCCC1Cc1cccc(F)c1] | 351.38 | 1.8 |
| 1-52 | 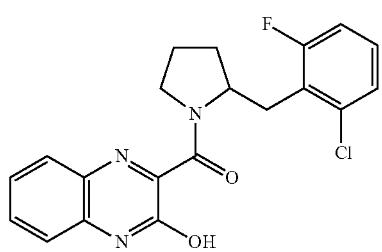 [SMILES: O=C(c1nc2ccccc2nc1O)N1CCCC1Cc1c(F)cccc1Cl] | 385.83 | 5.68 |
| 1-53 | 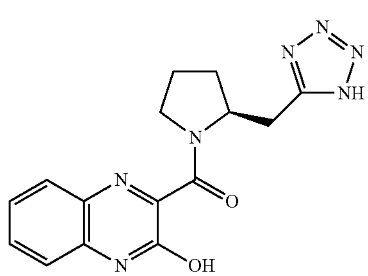 [SMILES: O=C(c1nc2ccccc2nc1O)N1CCC[C@H]1Cc1nnn[nH]1] | 325.33 | 50 |

TABLE 1-1-continued

| ID | Structure | MW | FABP4 TdF Kd uM |
|---|---|---|---|
| 1-54 | 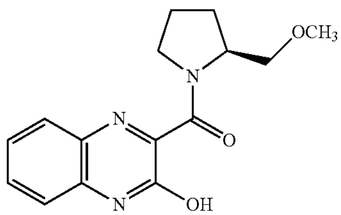 [SMILES: COC[C@@H]1CCCN1C(=O)c1nc2ccccc2nc1O] | 287.32 | 50 |
| 1-55 | 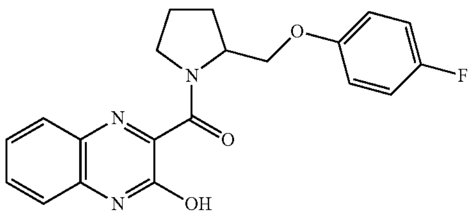 [SMILES: O=C(c1nc2ccccc2nc1O)N1CCCC1COc1ccc(F)cc1] | 367.38 | 23.04 |
| 1-56 | 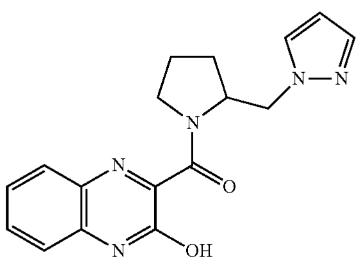 [SMILES: O=C(c1nc2ccccc2nc1O)N1CCCC1Cn1cccn1] | 323.36 | 50 |
| 1-57 | 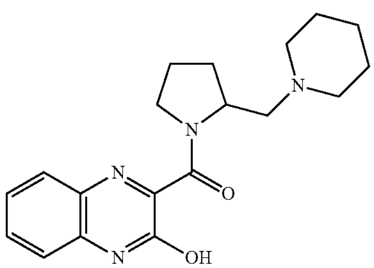 [SMILES: O=C(c1nc2ccccc2nc1O)N1CCCC1CN1CCCCC1] | 340.43 | 50 |
| 1-58 | 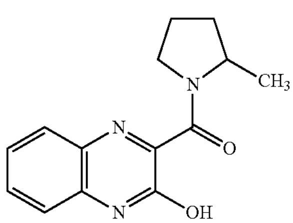 [SMILES: CC1CCCN1C(=O)c1nc2ccccc2nc1O] | 257.29 | 50 |
| 1-59 | 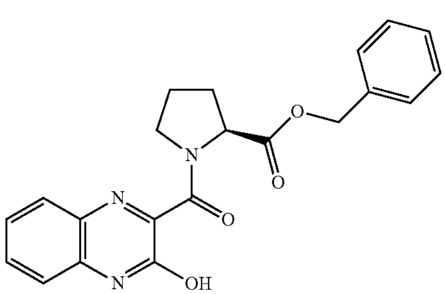 [SMILES: O=C(OCc1ccccc1)[C@@H]1CCCN1C(=O)c1nc2ccccc2nc1O] | 377.40 | 9.6 |

TABLE 1-1-continued

| ID | Structure | MW | FABP4 TdF Kd uM |
|---|---|---|---|
| 1-60 | 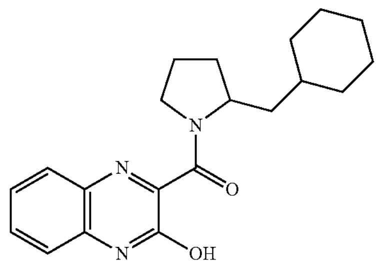 [SMILES: O=C(c1nc2ccccc2nc1O)N1CCCC1CC1CCCCC1] | 339.44 | |
| 1-61 | 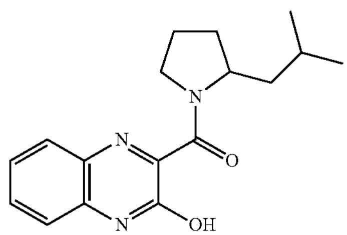 [SMILES: CC(C)CC1CCCN1C(=O)c1nc2ccccc2nc1O] | 299.38 | |
| 1-62 | 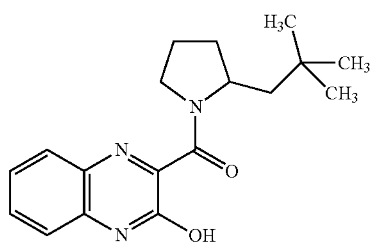 [SMILES: CC(C)(C)CC1CCCN1C(=O)c1nc2ccccc2nc1O] | 313.40 | |
| 1-63 | 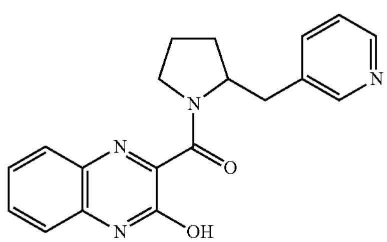 [SMILES: O=C(c1nc2ccccc2nc1O)N1CCCC1Cc1cccnc1] | 334.38 | 50 |
| 1-64 | 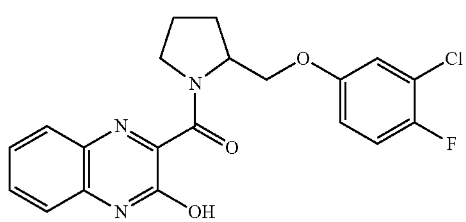 [SMILES: O=C(c1nc2ccccc2nc1O)N1CCCC1COc1ccc(F)c(Cl)c1] | 401.83 | 15.1 |
| 1-65 | 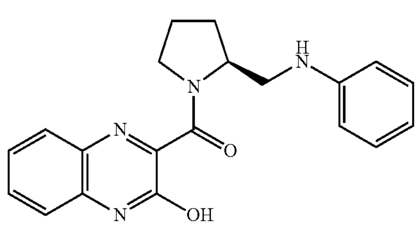 [SMILES: O=C(c1nc2ccccc2nc1O)N1CCC[C@H]1CNc1ccccc1] | 348.41 | 22.7 |

TABLE 1-1-continued

| ID | Structure | MW | FABP4 TdF Kd uM |
|---|---|---|---|
| 1-66 | 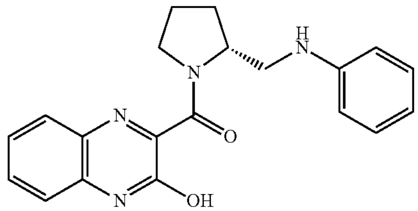 [SMILES: O=C(c1nc2ccccc2nc1O)N1CCC[C@@H]1CNc1ccccc1] | 348.41 | 50 |
| 1-67 | 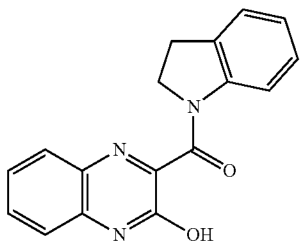 [SMILES: O=C(c1nc2ccccc2nc1O)N1CCc2ccccc21] | 291.31 | 50 |
| 1-68 | 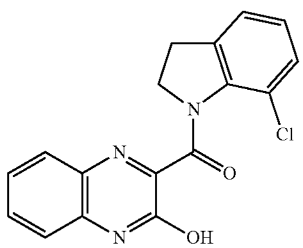 [SMILES: O=C(c1nc2ccccc2nc1O)N1CCc2cccc(Cl)c21] | 325.76 | 50 |
| 1-69 | 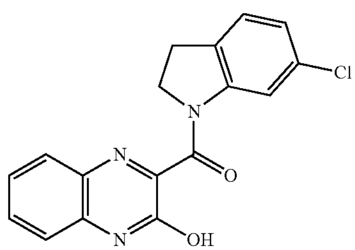 [SMILES: O=C(c1nc2ccccc2nc1O)N1CCc2ccc(Cl)cc21] | 325.76 | 50 |
| 1-70 | 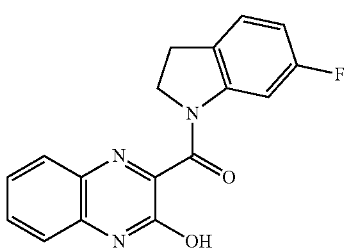 [SMILES: O=C(c1nc2ccccc2nc1O)N1CCc2ccc(F)cc21] | 309.30 | 50 |
| 1-71 | 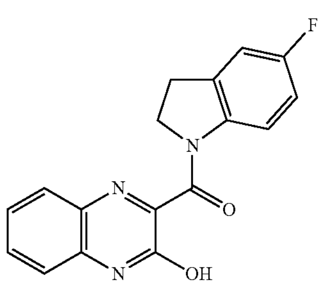 [SMILES: O=C(c1nc2ccccc2nc1O)N1CCc2cc(F)ccc21] | 309.30 | 50 |

TABLE 1-1-continued

| ID | Structure | MW | FABP4 TdF Kd uM |
|---|---|---|---|
| 1-72 | 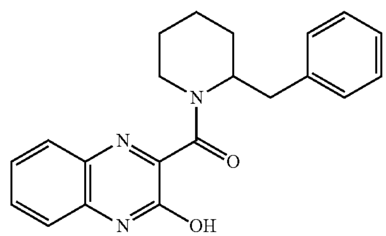 [SMILES: O=C(c1nc2ccccc2nc1O)N1CCCCC1Cc1ccccc1] | 347.42 | 14.2 |
| 1-73 | 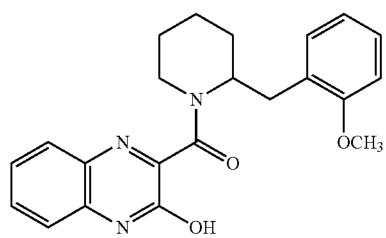 [SMILES: COc1ccccc1CC1CCCCN1C(=O)c1nc2ccccc2nc1O] | 377.45 | 2.25 |
| 1-74 | 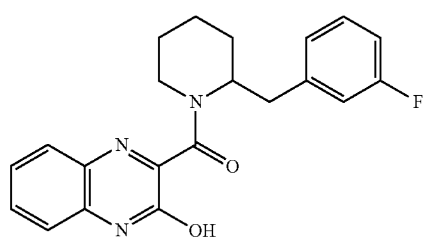 [SMILES: O=C(c1nc2ccccc2nc1O)N1CCCCC1Cc1cccc(F)c1] | 365.41 | 4.4 |
| 1-75 | 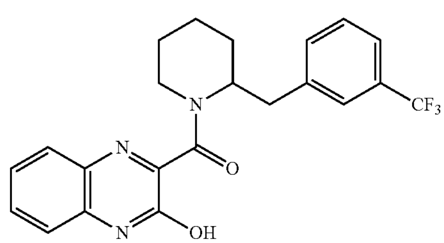 [SMILES: O=C(c1nc2ccccc2nc1O)N1CCCCC1Cc1cccc(C(F)(F)F)c1] | 415.42 | 0.98 |
| 1-76 | 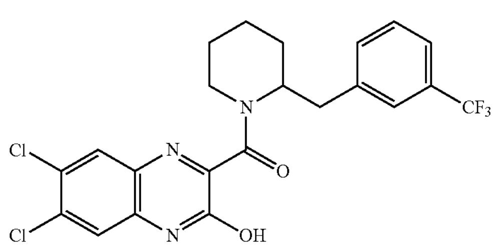 [SMILES: O=C(c1nc2cc(Cl)c(Cl)cc2nc1O)N1CCCCC1Cc1cccc(C(F)(F)F)c1] | 484.31 | |
| 1-77 | 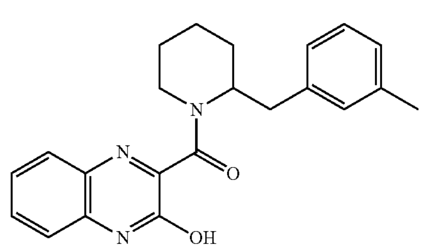 [SMILES: Cc1cccc(CC2CCCCN2C(=O)c2nc3ccccc3nc2O)c1] | 361.45 | |

TABLE 1-1-continued

| ID | Structure | MW | FABP4 TdF Kd uM |
|---|---|---|---|
| 1-78 | 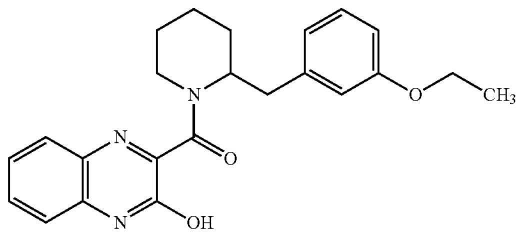 [SMILES: CCOc1cccc(CC2CCCCN2C(=O)c2nc3ccccc3nc2O)c1] | 391.47 | |
| 1-79 | 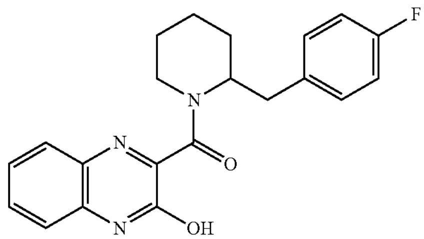 [SMILES: O=C(c1nc2ccccc2nc1O)N1CCCCC1Cc1ccc(F)cc1] | 365.41 | 4.7 |
| 1-80 | 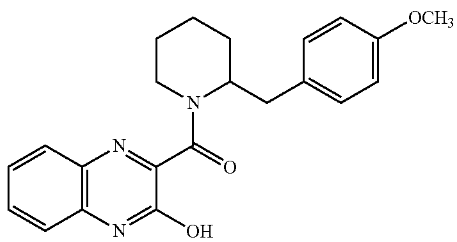 [SMILES: COc1ccc(CC2CCCCN2C(=O)c2nc3ccccc3nc2O)cc1] | 377.45 | 4.76 |
| 1-81 | 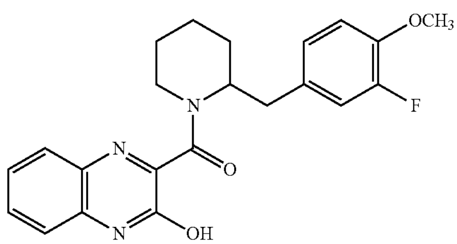 [SMILES: COc1ccc(CC2CCCCN2C(=O)c2nc3ccccc3nc2O)cc1F] | 395.44 | 50 |
| 1-82 | 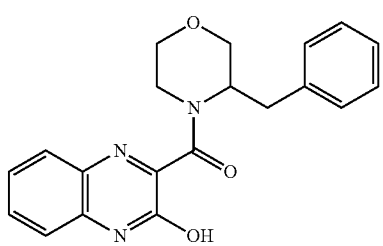 [SMILES: O=C(c1nc2ccccc2nc1O)N1CCOCC1Cc1ccccc1] | 349.39 | 50 |
| 1-83 | 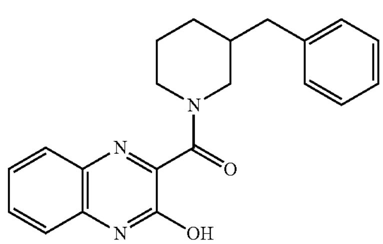 [SMILES: O=C(c1nc2ccccc2nc1O)N1CCCC(Cc2ccccc2)C1] | 347.42 | 16.2 |

TABLE 1-1-continued
| ID | Structure | MW | FABP4 TdF Kd uM |
|---|---|---|---|
| 1-84 | 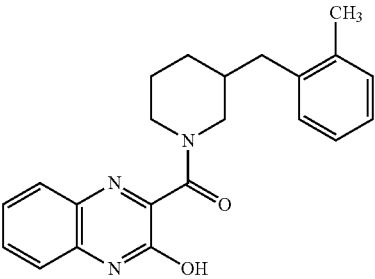 [SMILES: Cc1ccccc1CC1CCCN(C(=O)c2nc3ccccc3nc2O)C1] | 361.45 | |
| 1-85 | 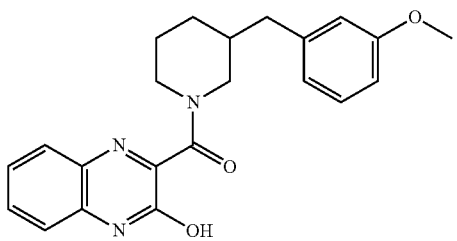 [SMILES: COc1cccc(CC2CCCN(C(=O)c3nc4ccccc4nc3O)C2)c1] | 377.45 | 11 |
| 1-86 | 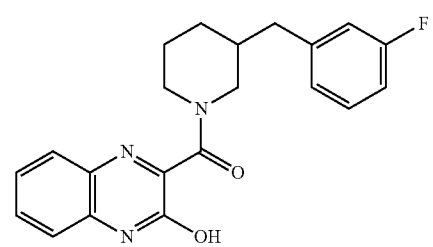 [SMILES: O=C(c1nc2ccccc2nc1O)N1CCCC(Cc2cccc(F)c2)C1] | 365.41 | 8.6 |
| 1-87 | 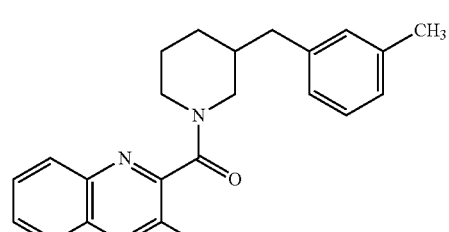 | 361.45 | |
| 1-88 | 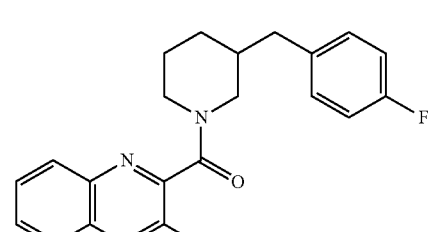 | 365.41 | 5.5 |

TABLE 1-1-continued

| ID | Structure | MW | FABP4 TdF Kd uM |
|---|---|---|---|
| 1-89 | 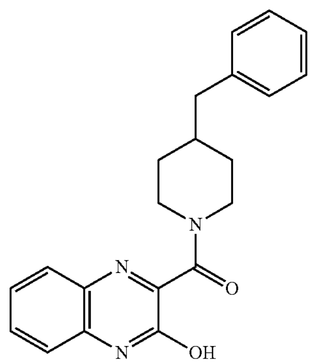 [SMILES: O=C(c1nc2ccccc2nc1O)N1CCC(Cc2ccccc2)CC1] | 347.42 | 50 |
| 1-90 | 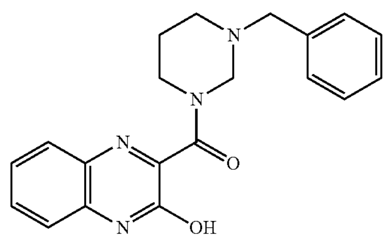 [SMILES: O=C(c1nc2ccccc2nc1O)N1CCCN(Cc2ccccc2)C1] | 348.41 | |
| 1-91 | 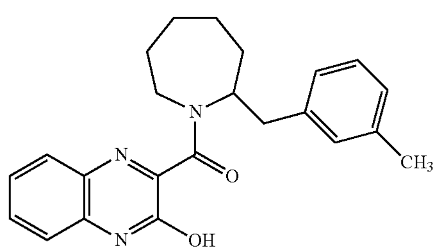 [SMILES: Cc1cccc(CC2CCCCCN2C(=O)c2nc3ccccc3nc2O)c1] | 375.47 | 1.84 |
| 1-92 | 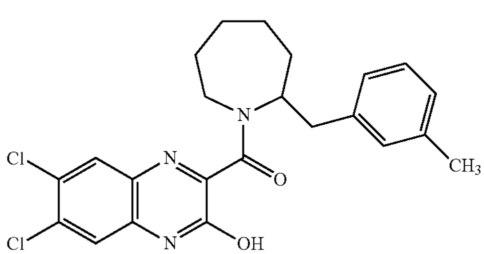 [SMILES: Cc1cccc(CC2CCCCCN2C(=O)c2nc3cc(Cl)c(Cl)cc3nc2O)c1] | 444.36 | |
| 1-93 | 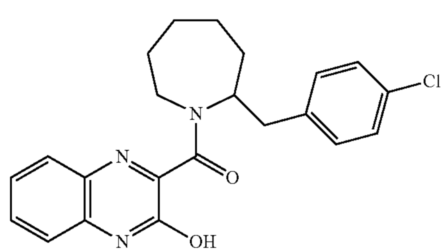 [SMILES: O=C(c1nc2ccccc2nc1O)N1CCCCCC1Cc1ccc(Cl)cc1] | 395.89 | 9 |

TABLE 1-1-continued
| ID | Structure | MW | FABP4 TdF Kd uM |
|---|---|---|---|
| 1-94 | 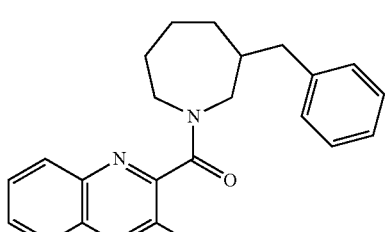 | 361.45 | 50 |
| 1-95 | 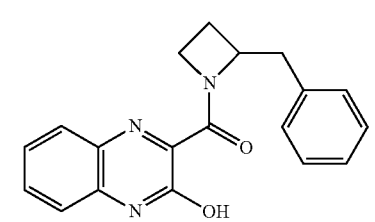 [SMILES: O=C(c1nc2ccccc2nc1O)N1CCC1Cc1ccccc1] | 319.37 | |
| 1-96 | 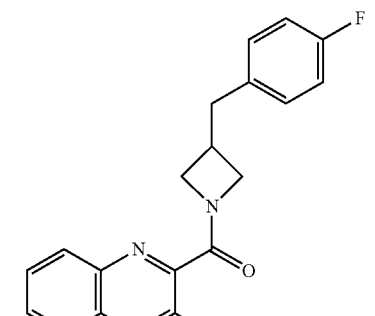 | 337.36 | 50 |
TABLE 1-2
| ID | Structure | MW | MS m/z (M+ + H) | FABP4 TdF Kd uM | Retention Time (min) |
|---|---|---|---|---|---|
| 1-98 | 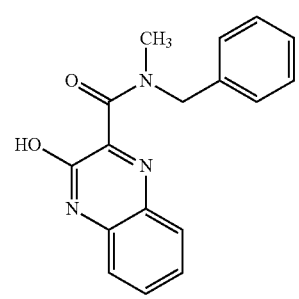 [SMILES: CN(Cc1ccccc1)C(=O)c1nc2ccccc2nc1O] | 293.33 | 294.12 | 28.4 | 3.62 |

TABLE 1-2-continued
| ID | Structure | MW | MS m/z (M⁺ + H) | FABP4 TdF Kd uM | Retention Time (min) |
|---|---|---|---|---|---|
| 1-99 | 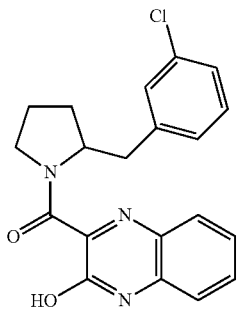 [SMILES: O=C(c1nc2ccccc2nc1O)N1CCCC1Cc1cccc(Cl)c1] | 367.84 | 368.11 | 0.95 | 4.57 |
| 1-100 | 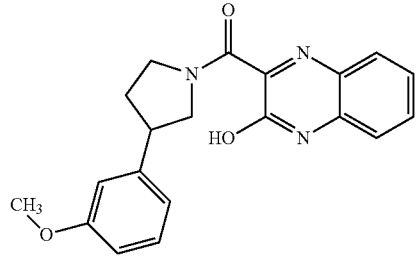 [SMILES: COc1cccc(C2CCN(C(=O)c3nc4ccccc4nc3O)C2)c1] | 349.39 | 350.14 | 50 | 3.91 |
| 1-101 | 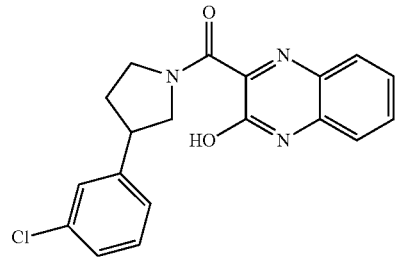 [SMILES: O=C(c1nc2ccccc2nc1O)N1CCC(c2cccc(Cl)c2)C1] | 353.81 | 354.09 | 50 | 4.35 |
| 1-102 | 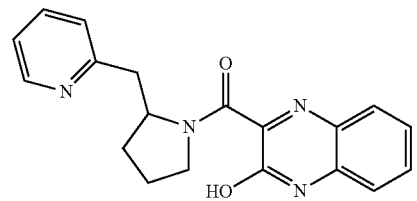 [SMILES: O=C(c1nc2ccccc2nc1O)N1CCCC1Cc1ccccn1] | 334.38 | 335.14 | 50 | 2.01 |
| 1-103 | 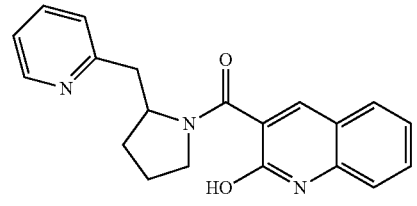 [SMILES: O=C(c1cc2ccccc2nc1O)N1CCCC1Cc1ccccn1] | 333.39 | 334.15 | 50 | 2.11 |
| 1-104 | 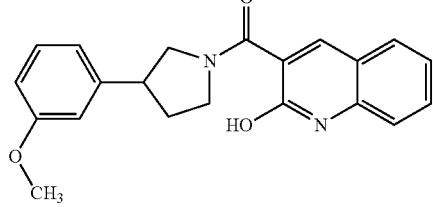 | 348.41 | 349.15 | 50 | 3.88 |

TABLE 1-2-continued
| ID | Structure | MW | MS m/z (M+ + H) | FABP4 TdF Kd uM | Retention Time (min) |
|---|---|---|---|---|---|
| 1-105 | 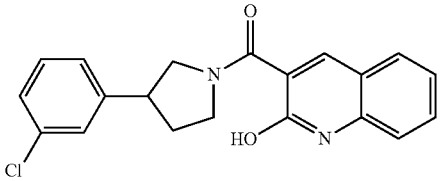 [SMILES: O=C(c1cc2ccccc2nc1O)N1CCC(c2cccc(Cl)c2)C1] | 352.82 | 353.10 | 50 | 4.31 |
| 1-106 | 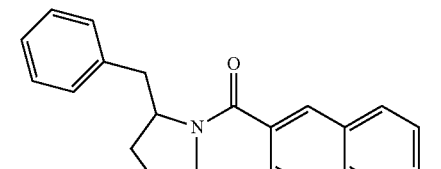 | 332.41 | 333.15 | 50 | 4.08 |
| 1-107 | 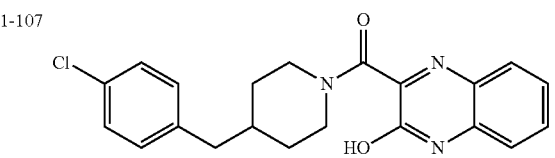 | 381.87 | 382.12 | 50 | 4.94 |
| 1-108 | 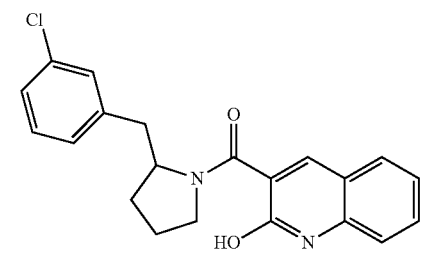 [SMILES: O=C(c1cc2ccccc2nc1O)N1CCCC1Cc1cccc(Cl)c1] | 366.85 | 367.11 | 50 | 4.46 |
| 1-109 | 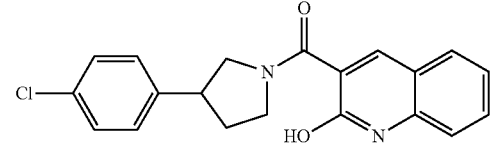 | 352.82 | 353.10 | 50 | 4.35 |
| 1-110 | 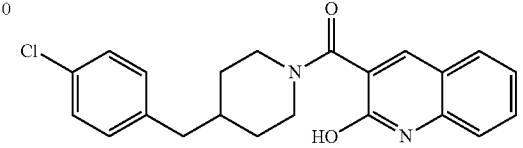 | 380.88 | 381.13 | 50 | 4.95 |
| 1-111 | 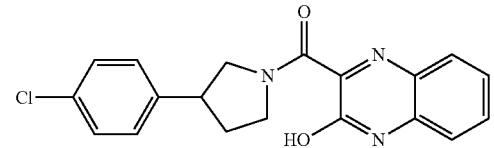 [SMILES: O=C(c1nc2ccccc2nc1O)N1CCC(c2ccc(Cl)cc2)C1] | 353.81 | 354.09 | 50 | 4.38 |
| 1-112 | 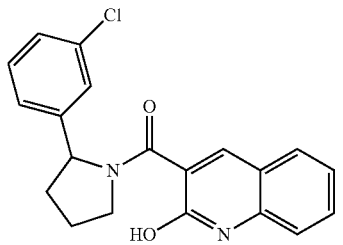 | 352.82 | 353.10 | 50 | 4.13 |

TABLE 1-2-continued

| ID | Structure | MW | MS m/z (M+ + H) | FABP4 TdF Kd uM | Retention Time (min) |
|---|---|---|---|---|---|
| 1-113 | 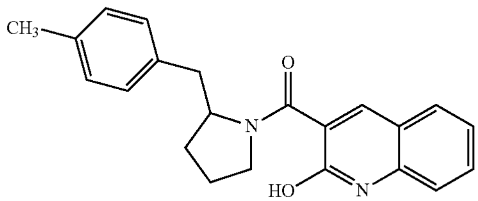 [SMILES: Cc1ccc(CC2CCCN2C(=O)c2cc3ccccc3nc2O)cc1] | 346.43 | 347.17 | 50 | 4.43 |
| 1-114 | 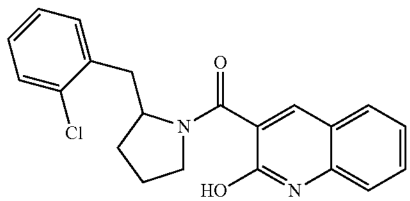 [SMILES: O=C(c1cc2ccccc2nc1O)N1CCCC1Cc1ccccc1Cl] | 366.85 | 367.11 | 50 | 4.25 |
| 1-115 | 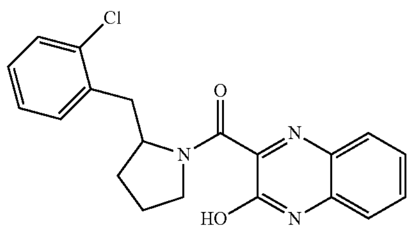 [SMILES: O=C(c1nc2ccccc2nc1O)N1CCCC1Cc1ccccc1Cl] | 367.84 | 368.11 | 1.8 | 4.35 |
| 1-116 | 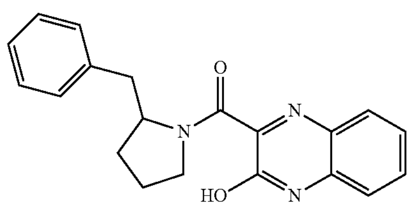 [SMILES: O=C(c1nc2ccccc2nc1O)N1CCCC1Cc1ccccc1] | 333.39 | 334.15 | 4.6 | 4.19 |
| 1-117 | 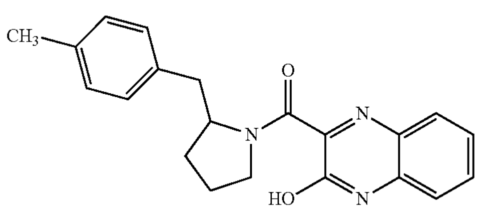 [SMILES: Cc1ccc(CC2CCCN2C(=O)c2nc3ccccc3nc2O)cc1] | 347.42 | 348.16 | 9.8 | 4.55 |
| 1-118 | 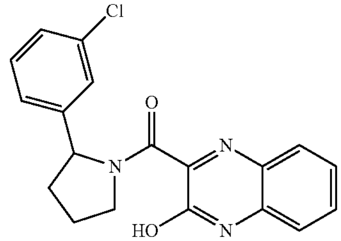 [SMILES: O=C(c1nc2ccccc2nc1O)N1CCCC1c1cccc(Cl)c1] | 353.81 | 354.09 | 50 | 4.11 |

TABLE 1-2-continued

| ID | Structure | MW | MS m/z (M+ + H) | FABP4 TdF Kd uM | Retention Time (min) |
| --- | --- | --- | --- | --- | --- |
| 1-122 | 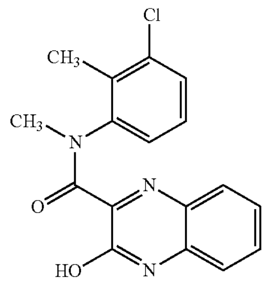 [SMILES: Cc1c(Cl)cccc1N(C)C(=O)c1nc2ccccc2nc1O] | 327.77 | 328.08 | 50 | 4.3 |
| 1-123 | 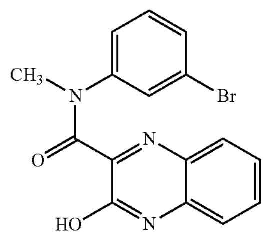 [SMILES: CN(C(=O)c1nc2ccccc2nc1O)c1cccc(Br)c1] | 358.20 | 358.01 | 50 | 3.92 |
| 1-124 | 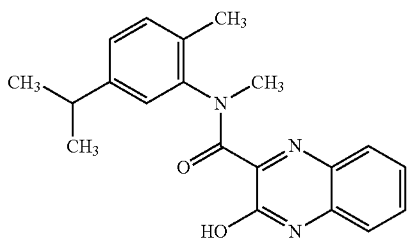 [SMILES: Cc1ccc(C(C)C)cc1N(C)C(=O)c1nc2ccccc2nc1O] | 335.41 | 336.16 | 11.3 | 4.7 |
| 1-130 | 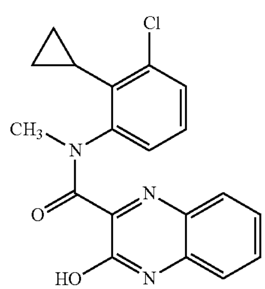 [SMILES: CN(C(=O)c1nc2ccccc2nc1O)c1cccc(Cl)c1C1CC1] | 353.81 | 354.09 | 50 | 4.71 |
| 1-133 | 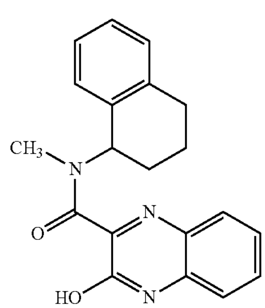 [SMILES: CN(C(=O)c1nc2ccccc2nc1O)C1CCCc2ccccc21] | 333.39 | 334.15 | 50 | 4.34 |

TABLE 1-2-continued

| ID | Structure | MW | MS m/z (M⁺ + H) | FABP4 TdF Kd uM | Retention Time (min) |
|---|---|---|---|---|---|
| 1-134 | 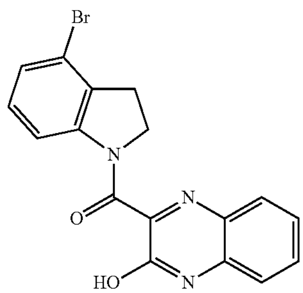 [SMILES: O=C(c1nc2ccccc2nc1O)N1CCc2c(Br)cccc21] | 370.21 | 370.01 | 50 | 4.59 |
| 1-135 | 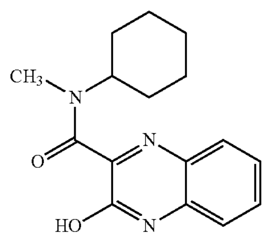 [SMILES: CN(C(=O)c1nc2ccccc2nc1O)C1CCCCC1] | 285.35 | 286.15 | 50 | 3.78 |
| 1-136 | 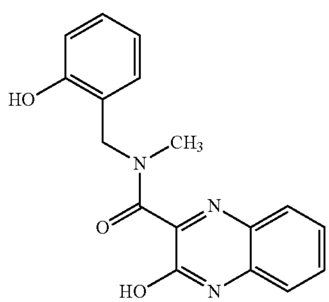 [SMILES: CN(Cc1ccccc1O)C(=O)c1nc2ccccc2nc1O] | 309.33 | 310.11 | 50 | 3.15 |
| 1-137 | 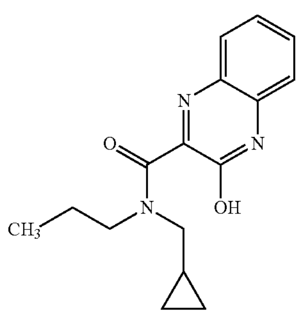 [SMILES: CCCN(CC1CC1)C(=O)c1nc2ccccc2nc1O] | 285.35 | 286.15 | 31 | 3.87 |
| 1-138 | 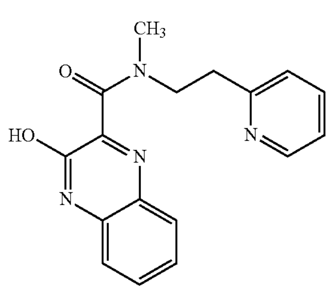 [SMILES: CN(CCc1ccccn1)C(=O)c1nc2ccccc2nc1O] | 308.34 | 309.13 | 50 | 3.87 |

TABLE 1-2-continued

| ID | Structure | MW | MS m/z (M⁺ + H) | FABP4 TdF Kd uM | Retention Time (min) |
|---|---|---|---|---|---|
| 1-139 | 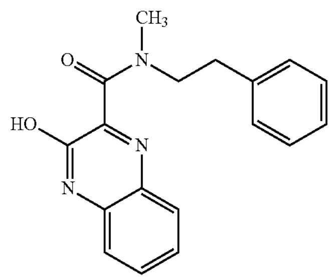 [SMILES: CN(CCc1ccccc1)C(=O)c1nc2ccccc2nc1O] | 307.36 | 308.13 | 12.7 | 3.83 |
| 1-140 | 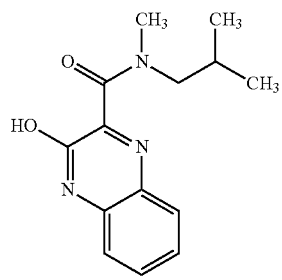 [SMILES: CC(C)CN(C)C(=O)c1nc2ccccc2nc1O] | 259.31 | 260.13 | 23.2 | 3.35 |
| 1-141 | 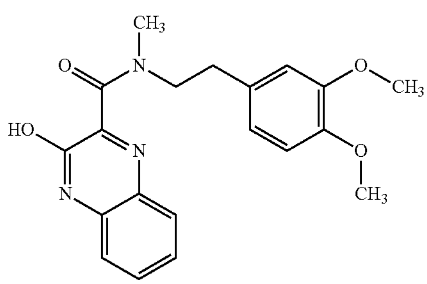 [SMILES: COc1ccc(CCN(C)C(=O)c2nc3ccccc3nc2O)cc1OC] | 367.41 | 368.15 | 26.1 | 3.42 |
| 1-142 | 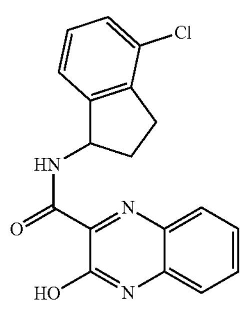 [SMILES: O=C(NC1CCc2c(Cl)cccc21)c1nc2ccccc2nc1O] | 339.78 | 340.08 | 50 | 4.2 |
| 1-143 | 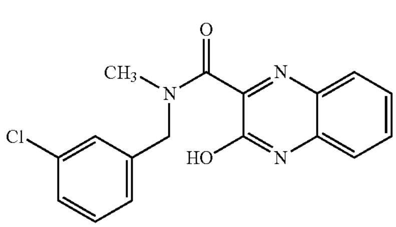 [SMILES: CN(Cc1cccc(Cl)c1)C(=O)c1nc2ccccc2nc1O] | 327.77 | 328.08 | 23.1 | 4.06 |

TABLE 1-2-continued

| ID | Structure | MW | MS m/z (M⁺ + H) | FABP4 TdF Kd uM | Retention Time (min) |
|---|---|---|---|---|---|
| 1-144 | 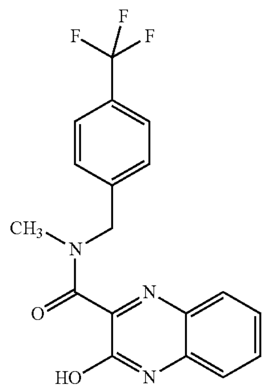 [SMILES: CN(Cc1ccc(C(F)(F)F)cc1)C(=O)c1nc2ccccc2nc1O] | 361.33 | 362.10 | 50 | 4.35 |
| 1-145 | 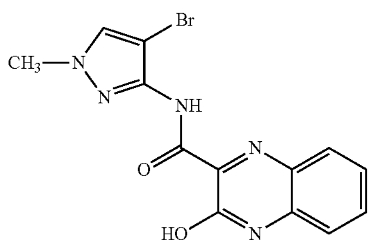 [SMILES: Cn1cc(Br)c(NC(=O)c2nc3ccccc3nc2O)n1] | 348.16 | 348.00 | 50 | 2.67 |
| 1-146 | 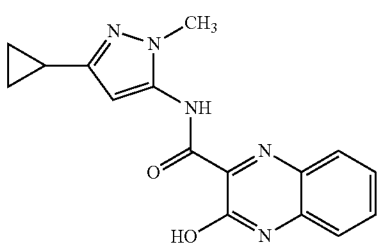 [SMILES: Cn1nc(C2CC2)cc1NC(=O)c1nc2ccccc2nc1O] | 309.33 | 310.12 | 50 | 2.92 |
| 1-147 | 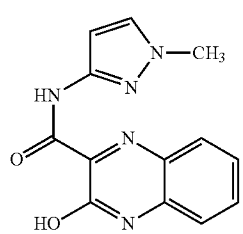 [SMILES: Cn1ccc(NC(=O)c2nc3ccccc3nc2O)n1] | 269.26 | 270.09 | 50 | 2.37 |
| 1-148 | 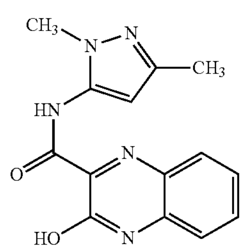 [SMILES: Cc1cc(NC(=O)c2nc3ccccc3nc2O)n(C)n1] | 283.29 | 284.11 | 50 | 2.45 |

TABLE 1-2-continued

| ID | Structure | MW | MS m/z (M+ + H) | FABP4 TdF Kd uM | Retention Time (min) |
|---|---|---|---|---|---|
| 1-149 | 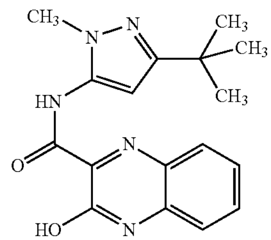 [SMILES: Cn1nc(C(C)(C)C)cc1NC(=O)c1nc2ccccc2nc1O] | 325.37 | 326.15 | 50 | 3.47 |
| 1-150 | 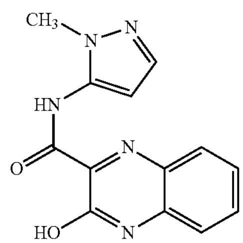 [SMILES: Cn1nccc1NC(=O)c1nc2ccccc2nc1O] | 269.26 | 270.09 | 50 | 2.28 |
| 1-153 | 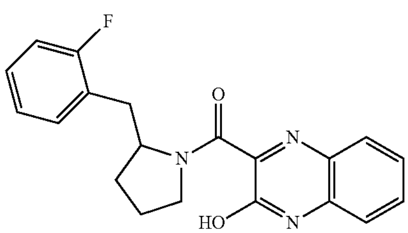 [SMILES: O=C(c1nc2ccccc2nc1O)N1CCCC1Cc1ccccc1F] | 351.38 | 352.14 | 2.9 | 4.16 |
| 1-156 | 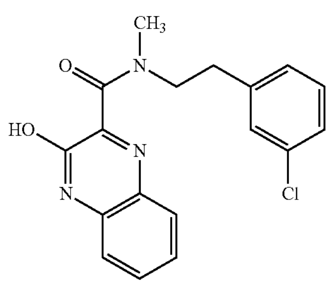 [SMILES: CN(CCc1cccc(Cl)c1)C(=O)c1nc2ccccc2nc1O] | 341.80 | 342.09 | 2.7 | 4.23 |
| 1-158 | 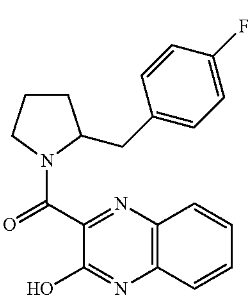 [SMILES: O=C(c1nc2ccccc2nc1O)N1CCCC1Cc1ccc(F)cc1] | 351.38 | 352.14 | 2 | 4.3 |

TABLE 1-2-continued

| ID | Structure | MW | MS m/z (M⁺ + H) | FABP4 TdF Kd uM | Retention Time (min) |
|---|---|---|---|---|---|
| 1-161 | 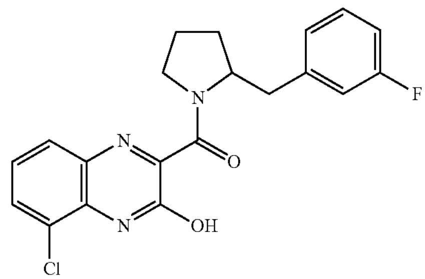 [SMILES: O=C(c1nc2cccc(Cl)c2nc1O)N1CCCC1Cc1cccc(F)c1] | 385.82 | 384 [M − H]⁻ | 0.022 | 2.9 |
| 1-162 | 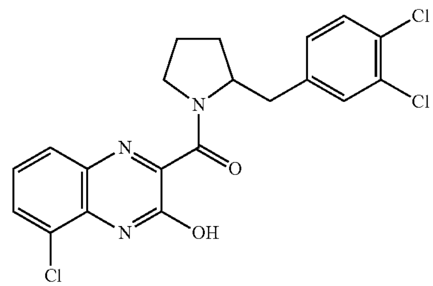 [SMILES: O=C(c1nc2cccc(Cl)c2nc1O)N1CCCC1Cc1ccc(Cl)c(Cl)c1] | 436.72 | 436 | 0.004 | 3.3 |
| 1-163 | 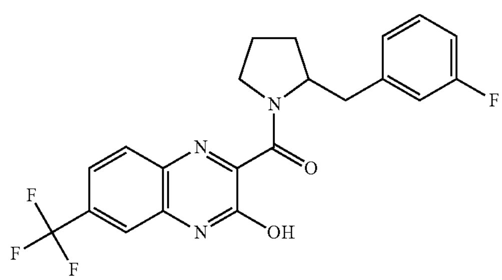 [SMILES: O=C(c1nc2ccc(C(F)(F)F)cc2nc1O)N1CCCC1Cc1cccc(F)c1] | 419.37 | 420 | 0.002 | 3.0 |
| 1-164 | 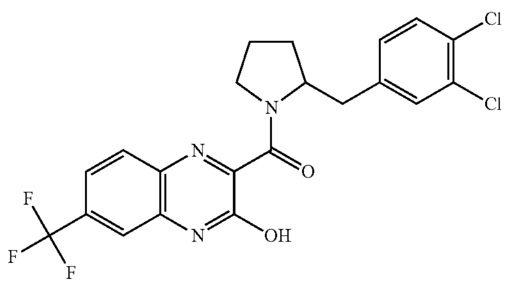 [SMILES: O=C(c1nc2ccc(C(F)(F)F)cc2nc1O)N1CCCC1Cc1ccc(Cl)c(Cl)c1] | 470.27 | 470 | 0.548 | 3.4 |
| 1-165 | 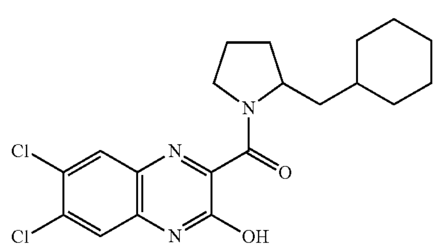 [SMILES: O=C(c1nc2cc(Cl)c(Cl)cc2nc1O)N1CCCC1CC1CCCCC1] | 408.32 | 408 | 0.244 | 3.8 |

General Method 2

Preparation of 6,7-difluoro-3-hydroxyquinoxaline-2-carboxylic acid

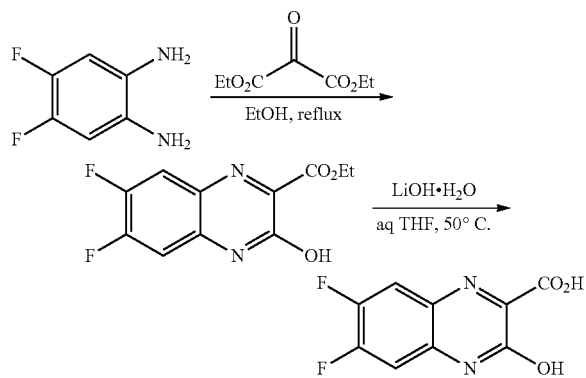

Step 1. A suspension of diethyl ketomalonate (1.11 mL, 7.3 mmol) and 1,2-diamino-4,5-difluorobenzene (1.0 g, 6.9 mmol) in anhydrous ethanol (20 mL) was heated at reflux under nitrogen for 3 h. The solvent was removed under reduced pressure and the residue was purified by flash column chromatography on silica gel, eluting with ethyl acetate/methylene chloride (1:2), to provide ethyl 6,7-difluoro-3-hydroxyquinoxaline-2-carboxylate as a light yellow solid:

$^1$H NMR (400 MHz, CDCl$_3$) δ 11.32 (br s, 1H), 7.83 (dd, 1H), 7.38-7.29 (m, 1H), 4.58 (q, 2H), 1.49 (t, 3H) ppm; ESI MS m/z 253 [M−H]$^−$.

Step 2. A mixture of ethyl 6,7-difluoro-3-hydroxyquinoxaline-2-carboxylate (500 mg, 2.0 mmol) and lithium hydroxide monohydrate (330 mg, 7.9 mmol) in THF (10 mL) and water (5 mL) was heated at 50° C. under nitrogen for 1 h. The mixture was further cooled to 0° C., acidified to pH 2 with concentrated HCl and extracted with ethyl acetate (100 mL). The organic extract was washed with brine (50 mL), dried over magnesium sulfate, filtered and the solvents were removed under reduced pressure to provide 6,7-difluoro-3-hydroxyquinoxaline-2-carboxylic acid as a yellow solid: $^1$H NMR (400 MHz, CD$_3$OD) δ 7.88 (dd, 1H), 7.29 (dd, 1H) ppm; ESI MS m/z 225 [M−H]$^−$.

General Method 3

Preparation of 6-chloro-3-hydroxyquinoxaline-2-carboxylic acid

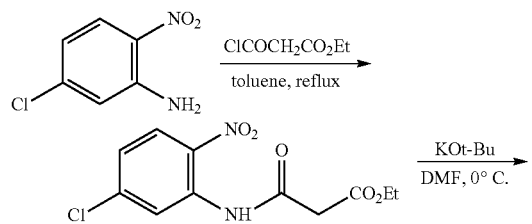

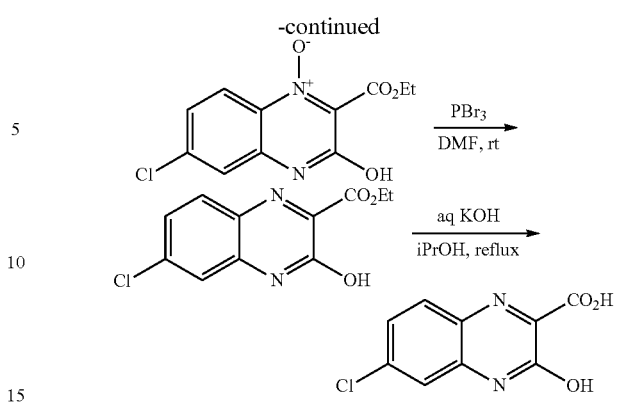

Step 1. A solution of 5-chloro-2-nitroaniline (2.0 g, 11.6 mmol) and ethyl 3-chloro-3-oxopropinate (1.6 mL, 12.2 mmol) in toluene (20 mL) was heated at reflux under nitrogen for 18 h, at which time thin-layer chromatography indicated that the reaction was essentially complete. The solvents were removed from the cooled mixture under reduced pressure and the residue was purified by flash column chromatography on silica gel, eluting with ethyl acetate/hexanes (1:4), to provide ethyl 3-(5-chloro-2-nitrophenylamino)-3-oxopropanoate as a light yellow solid: $^1$H NMR (400 MHz, CDCl$_3$) δ 8.80 (d, 1H), 8.15 (d, 1H), 7.17 (dd, 1H), 4.31 (q, 2H), 1.34 (t, 3H) ppm; ESI MS m/z 285 [M−H]$^−$.

Step 2. A solution of ethyl 3-(5-chloro-2-nitrophenylamino)-3-oxopropanoate (1.5 g, 5.2 mmol) in anhydrous DMF (8 mL) was added dropwise to a solution of potassium tert-butoxide (1.2 g, 10.5 mmol) in anhydrous DMF (5 mL) at 0° C. under nitrogen, after which the mixture was stirred for 2 h. The cold mixture was diluted with water (50 mL), acidified to pH 2 with 2 N HCl and extracted with methylene chloride (3×30 mL). The combined organic extracts were washed with water (45 mL), dried over sodium sulfate, filtered and the solvents were removed under reduced pressure. The residue was purified by flash column chromatography on silica gel, eluting with ethyl acetate/hexanes (3:7), to provide 6-chloro-2-(ethoxycarbonyl)-3-hydroxyquinoxaline-1-oxide as a light yellow solid: $^1$H NMR (400 MHz, CDCl$_3$) δ 8.25 (d, 1H), 7.46 (d, 1H), 7.34 (dd, 1H), 4.55 (q, 2H), 1.45 (t, 3H) ppm; ESI MS m/z 267 [M−H]$^−$.

Step 3. Phosphrous tribromide (0.36 mL) was added dropwise to a solution of 6-chloro-2-(ethoxycarbonyl)-3-hydroxyquinoxaline-1-oxide (0.50 g, 1.86 mmol) in anhydrous DMF (16 mL) at room temperature under nitrogen, after which the mixture was stirred for 12 h (at which point $^1$H NMR analysis of an aliquot indicated that the reaction was complete). The mixture was poured into ice-water mixture (100 mL) and extracted with methylene chloride (3×30 mL). The combined organic extracts were washed with water (45 mL), dried over sodium sulfate, filtered and the solvents were removed under reduced pressure to provide 6-chloro-2-(ethoxycarbonyl)-3-hydroxyquinoxaline as a light yellow solid that was suitable for use without further purification: $^1$H NMR (400 MHz, CDCl$_3$) δ 7.89 (d, 1H), 7.48 (d, 1H), 7.37 (dd, 1H), 4.54 (q, 2H), 1.48 (t, 3H) ppm; ESI MS m/z 251 [M−H]$^−$.

Step 4. Potassium hydroxide (1.25 g, 22.2 mmol) was added to a suspension of 6-chloro-2-(ethoxycarbonyl)-3-hydroxyquinoxaline (0.56 g, 2.22 mmol) in 2-propanol (5 mL) and water (7.5 mL) and the resulting solution were heated at reflux for 12 h. The cooled mixture was acidified to pH 2 and the solvents were removed under reduced pressure, after which the residue was taken up in water (50 mL) and extracted with ethyl acetate (2×40 mL). The organic extracts were combined and the solvents were removed under reduced pressure, producing a residue that was purified by flash column chromatography on silica gel, eluting with methanol/methylene chloride (1:9), to provide 6-chloro-3-hydroxyquinoxaline-2-carboxylic acid as a light yellow solid: $^1$H NMR (400 MHz, CD$_3$OD) δ 7.91 (d, 1H), 7.45 (d, 1H), 7.37 (dd, 1H) ppm; ESI MS m/z 223 [M−H]$^-$.

General Method 4

Preparation of 3-hydroxy-6-(methylsulfonyl)quinoxaline-2-carboxylic acid

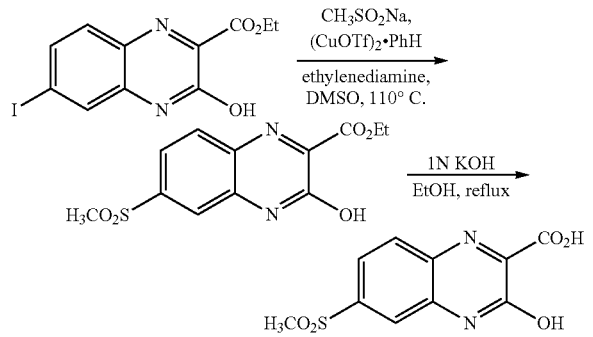

Step 1. A degassed mixture of ethyl 3-hydroxy-6-iodoquinoxaline-2-carboxylate (351 mg, 1.0 mmol), sodium methanesulfinate (132 mg, 1.3 mmol), copper(I) triflate benzene complex (25 mg, 5 mol %) and ethylenediamine (0.01 mL, 10 mol %) in anhydrous DMSO (1.0 mL) was heated at 110° C. in a sealed reaction vessel for 20 h. The cooled mixture was diluted with ethyl acetate (10 mL) and filtered through a plug of silica gel under reduced pressure, eluting with additional ethyl acetate (50 mL). The filtrate was washed with water (20 mL) and brine (20 mL), dried over sodium sulfate and filtered. The solvents were removed under reduced pressure and the residue was purified by flash column chromatography on silica gel, eluting with ethyl acetate, to provide ethyl 3-hydroxy-6-(methylsulfonyl)quinoxaline-2-carboxylate as a yellow solid: $^1$H NMR (400 MHz, CDCl$_3$) δ 11.61 (br S, 1H), 8.16 (d, J=8.9 Hz, 1H), 8.01 (s, 1H), 7.91 (d, J=9.9 Hz, 1H), 4.58 (q, J=6.7 Hz, 2H), 3.16 (s, 3H), 1.49 (t, J=6.7 Hz) ppm; ESI MS m/z 297 [M+H]$^-$.

Step 2. Potassium hydroxide (1.0 mL, 1.8 mmol, 1.0 N solution) was added to a suspension of ethyl 3-hydroxy-6-(methylsulfonyl)quinoxaline-2-carboxylate (249 mg, 0.84 mmol) in ethanol (30 mL) and the resulting mixture was heated at reflux for 2 h. The cooled mixture was diluted with water (10 mL), acidified to pH 1 and the resulting solids were collected by filtration under reduced pressure to provide 3-hydroxy-6-(methylsulfonyl)quinoxaline-2-carboxylic acid as an off-white solid: $^1$H NMR (400 MHz, CDCl$_3$) δ 8.07 (d, J=8.6 Hz, 1H), 7.87-7.84 (m, 2H), 3.31 (s, 3H) ppm.

General Method 5

Preparation of (3-aminoquinoxalin-2-yl)[2-(3-chlorobenzyl)pyrrolidin-1-yl]methanone (5-2)

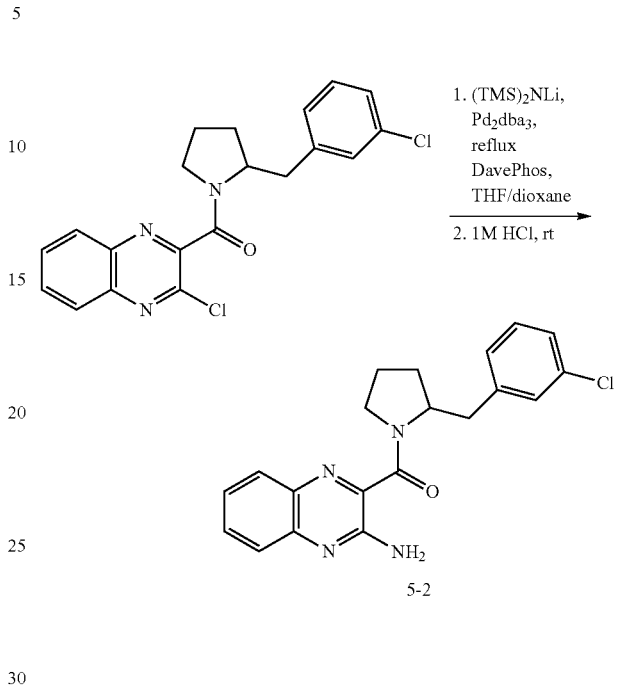

Lithium bis(trimethylsilyl)amide (1.3 mL, 1.34 mmol, 1.0 M in THF) was added dropwise to a degassed mixture of (2-(3-chlorobenzyl)pyrrolidin-1-yl)(3-chloroquinoxalin-2-yl)methanone (235 mg, 0.61 mmol), tris(dibenzylideneacetone) dipalladium(0) (28 mg, 5 mol %) and 2-dicyclohexylphosphino-2'-(N,N-dimethylamino)biphenyl (12 mg, 5 mol %) in anhydrous 1,4-dioxane (5.0 mL) at room temperature under nitrogen, after which the mixture was heated to reflux to stir for 16 h. The cooled mixture was treated with 1 N HCl (2 mL), stirred for 30 min and the adjusted to pH 10 with 2 N sodium hydroxide solution and diluted with brine (100 mL). The mixture was extracted with ethyl acetate (2×150 mL) and the combined organic extracts were washed with brine (100 mL), dried over magnesium sulfate and filtered. The filtrate solvents were removed under reduced pressure and the residue was purified by flash column chromatography on silica gel, eluting with hexanes/ethyl acetate (1:1), to provide (3-aminoquinoxalin-2-yl)(2-(3-chlorobenzyl)pyrrolidin-1-yl)methanone as a brown oil: $^1$H NMR (400 MHz, CDCl$_3$, ~2:1 mixture of rotamers) δ 7.88 (d, J=9.5 Hz, 1H, rotamers A and B), 7.67-7.63 (m, 1H, rotamers A and B), 7.49-7.11 (m, 1H, rotamers A and B), 7.34 (s, 1H, rotamer A), 7.28-7.19 (m, 1H, rotamers A and B and 3H, rotamer A), 7.09 (d, J=8.9 Hz, rotamer B), 7.00 (t, J=7.8 Hz, rotamer B), 6.88 (s, 1H, rotamer B), 6.73 (d, J=7.8 Hz, 1H, rotamer B), 6.19 (s, 2H, NH$_2$, rotamer A), 6.08 (s, 2H, NH$_2$, rotamer B), 5.22-5.15 (m, 1H, rotamer B), 4.61-4.54 (m, 1H, rotamer A), 3.96-3.89 (m, 2H, rotamer B), 3.84-3.73 (m, 2H, rotamer A), 3.37 (dd, J=3.3. 12.8 Hz, 1H, rotamer A), 2.95 (dd, J=5.0, 13.4 Hz, 1H, rotamer B), 2.83-2.73 (m, 1H, rotamer A), 2.59-2.53 (m, 1H, rotamer B), 2.07-1.75 (m, 4H, rotamers A and B) ppm; ESI MS m/z 367 [M+H]$^+$.

| ID | Structure | MW | FABP4 TdF Kd uM |
|---|---|---|---|
| 5-2 | 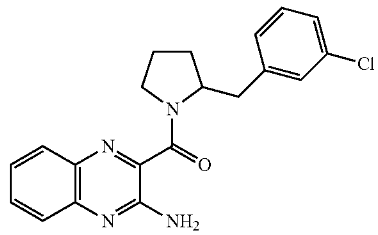 [SMILES: Nc1nc2ccccc2nc1C(=O)N1CCCC1Cc1cccc(Cl)c1] | 366.84 | 10 |

General Method 6

Preparation of (2-((3-chlorophenoxy)methyl)piperidin-1-yl)(3-hydroxyquinoxalin-2-yl)methanone (6-5)

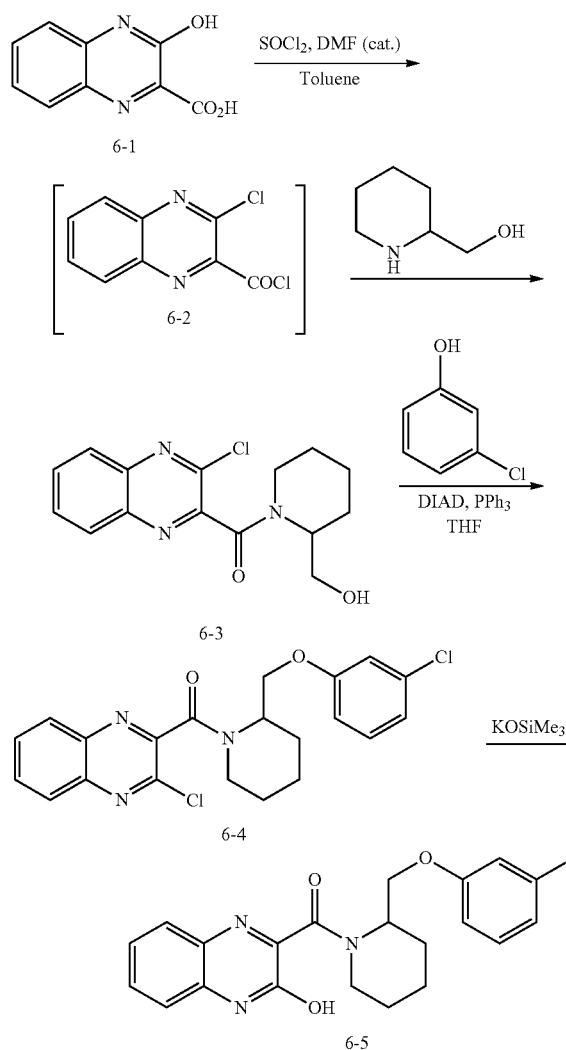

Step 1: A suspension of 3-hydroxy-2-quinoxaline carboxylic acid 6-1 (1.0 g, 5.26 mmol), thionyl chloride (4.6 mL, 63.1 mmol, 12.0 equiv) and catalytic DMF (50 µL) in 10 mL toluene was heated to 80° C. After 1 h of heating, the reaction mixture was cooled to room temperature and evaporated to dryness to yield 6-2. In a separate flask, 2-piperidine methanol (0.61 g, 5.26 mmol) and triethylamine (0.88 mL, 6.3 mmol, 1.2 equiv) in 10 mL CH₂Cl₂ was cooled to 0° C. To this mixture was added 6-2 dropwise. The reaction was allowed to stir at room temperature for 1 h after which was diluted with H₂O (10 mL), extracted with CH₂Cl₂ (2×10 mL), dried over Na₂SO₄ and evaporated to dryness. The crude product was purified by flash chromatography (20-40% EtOAc/hexanes) to produce compound 6-3.

Step 2: To a mixture of 6-3 (0.25 g, 0.82 mmol), 3-chloro phenol (0.224 g, 1.64 mmol, 2.0 equiv) and PPh₃ (0.43 g, 1.64 mmol, 2.0 equiv) in 10 mL THF was added DIAD (0.33 mL, 1.64 mmol, 2.0 equiv) dropwise. The reaction was allowed to stir at room temperature overnight, concentrated and purified by flash chromatography (5-20% EtOAc/hexanes) to yield 6-4.

Step 3: A solution of 6-4 (0.1 g, 0.24 mmol) and potassium trimethylsilanolate (0.31 g, 2.16 mmol, 9.0 equiv) in 5 mL THF was refluxed for 2 h. After the reaction mixture was cooled to room temperature, 5 mL of sat. NH₄Cl was added. The mixture was extracted with CH₂Cl₂ (2×10 mL), dried over Na₂SO₄ and evaporated to dryness. The crude product was purified by flash chromatography (20% EtOAc/CH₂Cl₂) to produce 6-5.

| ID | Structure | MW | FABP4 TdF Kd uM |
|---|---|---|---|
| 6-5 | 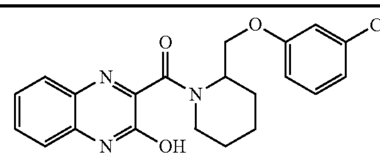 | 397.85 | 50 |

General Method 7

Preparation of (R)-(2-(3-chlorobenzyl)piperidin-1-yl)(3-hydroxyquinoxalin-2-yl)methanone (7-7)

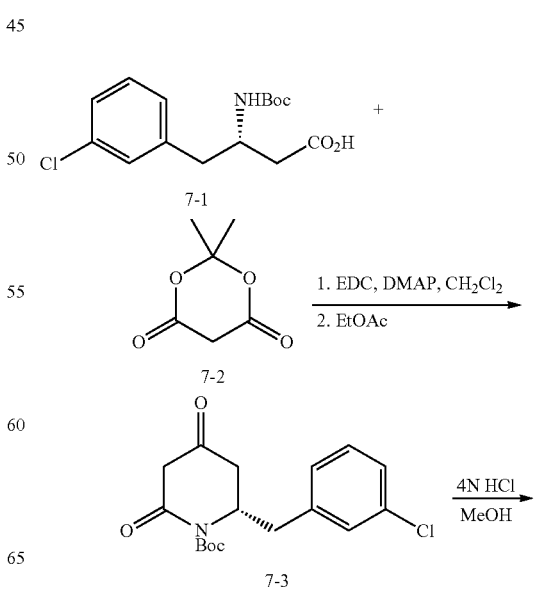

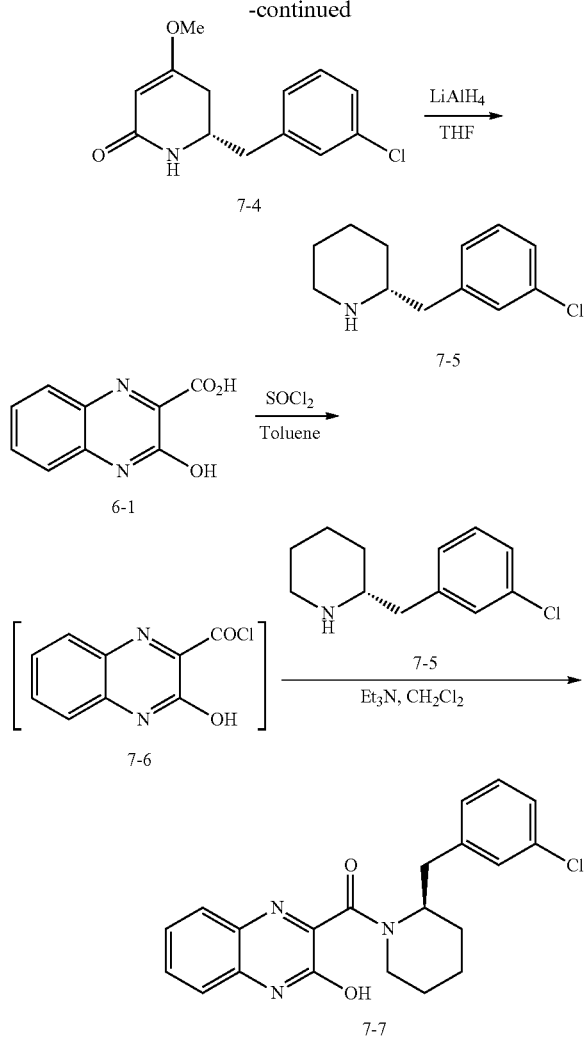

temperature overnight. After overnight stirring, the reaction mixture was cooled back to 0° C. and 10 mL of sat. Na$_2$SO$_4$ was added and the reaction stirred for 30 min at room temperature. The white suspension was filtered through celite and the organic layer was dried over Na$_2$SO$_4$, filtered and concentrated to yield the crude product which was purified by flash chromatography (2% to 10% MeOH/CH$_2$Cl$_2$) to yield the piperidine 7-5.

Step 4: A suspension of 3-hydroxy-2-quinoxaline carboxylic acid 6-1 (500 mg, 2.63 mmol) and thionyl chloride (2.3 mL, 31.6 mmol, 12.0 equiv) in 10 mL toluene was heated to 80° C. After 2 h of heating, the reaction mixture was cooled to room temperature and evaporated to dryness to yield the acid chloride 7-6. In a separate flask, piperidine 7-5 (0.55 g, 2.63 mmol) and triethylamine (0.73 mL, 5.26 mmol, 2.0 equiv) in 10 mL CH$_2$Cl$_2$ was cooled to 0° C. To this mixture was added the acid chloride 7-6 dropwise. The reaction was allowed to stir at room temperature for 3 h after which was diluted with H$_2$O (10 mL), extracted with EtOAc (2×10 mL), washed with sat. NaHCO$_3$, dried over Na$_2$SO$_4$ and evaporated to dryness. The crude product was purified by flash chromatography (10-30% EtOAc/CH$_2$Cl$_2$) to produce 7-7 (R isomer).

Preparation of (S)-(2-(3-chlorobenzyl)piperidin-1-yl)
(3-hydroxyquinoxalin-2-yl)methanone (7-8)

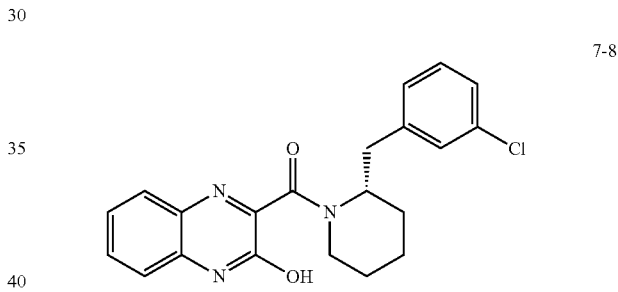

7-8

Compound 7-8 (S isomer) was prepared analogous to the preparation of Compound 7-7 beginning from Boc-(R)-3-amino-4-(3-chlorophenyl)butyric acid.

Step 1: To a suspension of Boc-(S)-3-amino-4-(3-chlorophenyl)butyric acid 7-1 (5.0 g, 15.9 mmol) in 65 mL CH$_2$Cl$_2$ at 0° C. was added N-(3-dimethylaminopropyl)-N'-ethylcarbodiimide hydrochloride (4.6 g, 23.9 mmol, 1.5 equiv), DMAP (2.9 g, 23.9 mmol, 1.5 equiv) and Meldrum's acid 7-2 (2.3 g, 15.9 mmol, 1.0 equiv). The reaction was allowed to stir from 0° C. to room temperature for 3 h after which, 100 mL of 1 N KHSO$_4$ was added. The organic layer was separated, dried over Na$_2$SO$_4$, and evaporated to dryness. The crude was then dissolved in 150 mL of EtOAc and refluxed to 75° C. overnight. After cooling to room temperature, 1 N KHSO$_4$ was added and extracted with EtOAc (2×25 mL), dried over Na$_2$SO$_4$, filtered and concentrated. The crude solid was dissolved in minimum CH$_2$Cl$_2$ and hexane was added until precipitation occurred. The product was filtered, triturated with CH$_2$Cl$_2$/hexanes (1:5) and dried to produce the compound as a white solid (7-3).

Step 2: A mixture of 7-3 (2.13 g, 6.3 mmol) and 4 N HCl in dioxane (15.8 mL, 63 mmol, 10.0 equiv) in MeOH was stirred at room temperature overnight. The reaction mixture was concentrated and purified by flash chromatography (2% to 4% MeOH/CH$_2$Cl$_2$) to produce 7-4.

Step 3: LiAlH$_4$ (19.9 mL, 19.9 mmol, 1 M in THF) was added dropwise to 7-4 (1.0 g, 3.97 mmol) in THF at 0° C. The reaction was allowed to gradually stir from 0° C. to room

| ID | Structure | MW | FABP4 TdF Kd uM |
|---|---|---|---|
| 7-7 | 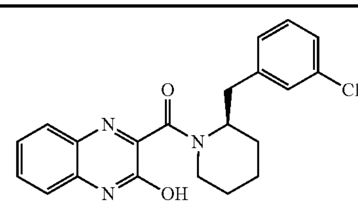 | 381.86 | 8.1 |
| 7-8 | 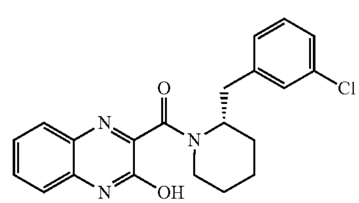 [SMILES: O=C(c1nc2ccccc2nc1O)N1CCCC[C@H]1Cc1cccc(Cl)c1] | 381.86 | 1.2 |

General Method 8

Preparation of (S)-(2-(3,5-dichlorobenzyl)pyrrolidin-1-yl)(3-hydroxyquinoxalin-2-yl)methanone (8-6)

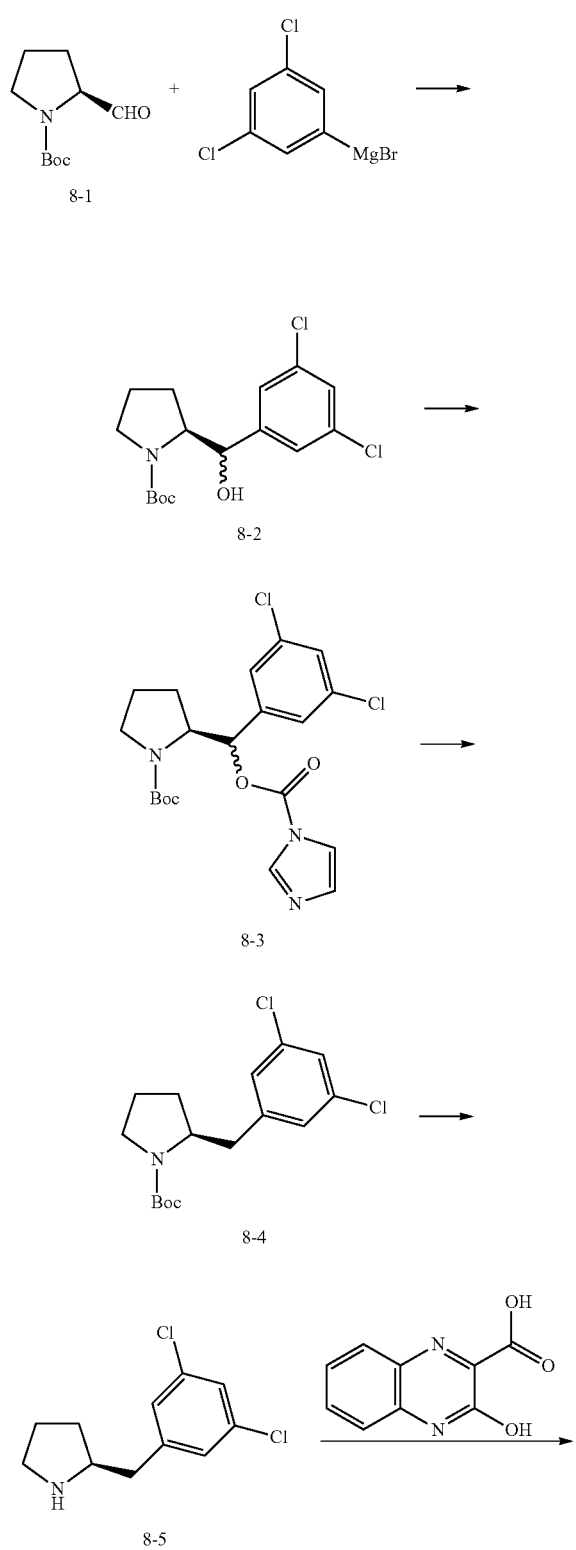

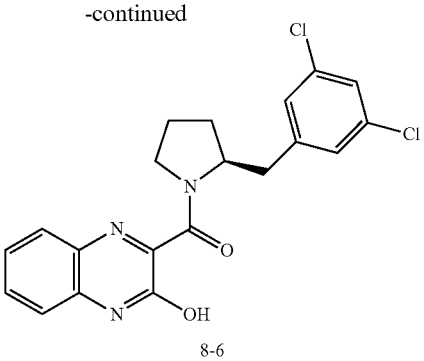

Step 1: A solution of (3,5-dichlorophenyl)magnesium bromide (20 mL, 0.2 M in THF) was added dropwise to a solution (S)-Boc-2-prolinal 8-1 (0.96 g, 4.82 mmol) in THF (20 mL) at −78° C. under nitrogen. The resulting solution was stired at −78° C. for 30 min, then warmed up to room temperature and stirred at room temperature for 2 h. Water and EtOAc were added sequentially. The aqueous layer was separated and extracted with EtOAc. The organic extracts were combined, washed with brine, filtered through a pad of Celite, dried (MgSO$_4$), and filtered. The filtrate was concentrated in vacuo, and the residue was purified by column chromatography (silica gel, gradient elution with 10% EtOAc/hexanes to 25% EtOAc/hexanes), to give the desired compound 8-2 (M+1: 346.3).

Step 2: Compound 8-2 (121 mg, 0.35 mmol) and thiocarbodiimidazole (190 mg, 1.06 mmol) were dissolved in 2 mL dichloroethane in a sealed tube. The mixture was heated at 85° C. for 2 h. The solution was concentrated, and residue was purified by preparative TLC (EtOAc/hexanes, 1:1, v/v) to give the desired compound 8-3 (M+1: 456.2).

Step 3: Compound 8-3 (130 mg, 0.28 mmol), AIBN (9 mg, 0.054 mmol) and tributyltinhydride (0.38 mL, 1.14 mmol) were mixed in toluene (2 mL). The mixture was heated at 85° C. under nitrogen overnight. The solution was concentrated, and filtered through a pad of Celite. The filtrate was concentrated and purified by column chromatograph (silica gel, EtOAc/hexanes, 1:15, v/v) to give the desired compound 8-4 (M+1: 330.2).

Step 4: Starting material 8-4 (0.15 g, 0.45 mmol) was dissolved in DCM (0.5 mL) and TFA (0.5 mL). The resulting mixture was stirred at room temperature for 2 h. Solvent was removed to give desired compound 8-5. Compound 8-5,3-oxo-3,4-dihydroquinoxaline-2-carboxylic acid (100 mg, 0.52 mmol), HATU (250 mg, 0.66 mmol) and iPr$_2$NEt (0.4 mL, 2.29 mmol) were mixed in DMF (2 mL). The resulting mixture was heated at 85° C. overnight. The mixture was cooled to room temperature and the solvent was removed. The residue was purified by column chromatograph (silica gel, gradient elution with 7 N NH$_3$-methanol/DCM, 1:60, v/v to 7N NH$_3$-methanol/DCM, 1:10, v/v) to give desired product 8-6 (M+1: 402.2).

The following examples were prepared using General Method 8 as described above:

| ID | Structure | MW | MS m/z (M+ + H) | FABP4 TdF Kd uM | Retention Time (min) |
|---|---|---|---|---|---|
| 8-6 | 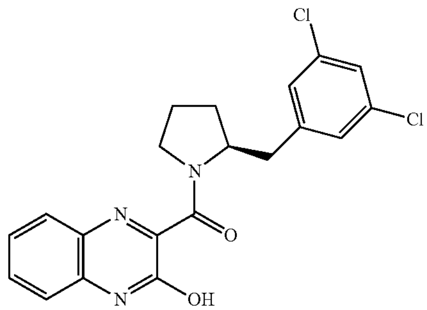 [SMILES: O=C(c1nc2ccccc2nc1O)N1CCC[C@H]1Cc1cc(Cl)cc(Cl)c1] | 402.27 | | 0.25 | |
| 8-10 | 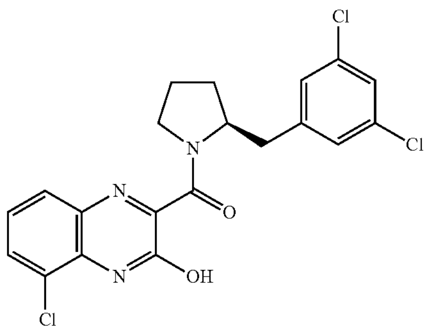 [SMILES: O=C(c1nc2cccc(Cl)c2nc1O)N1CCC[C@H]1Cc1cc(Cl)cc(Cl)c1] | 436.72 | 434 [M − H]− | 0.0001 | 3.3 |
| 8-11 | 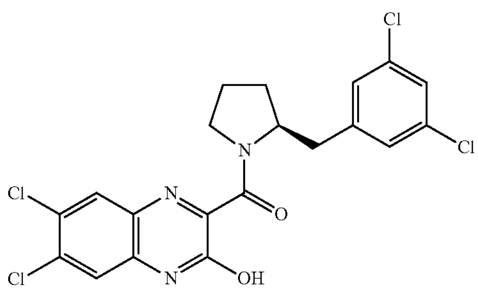 [SMILES: O=C(c1nc2cc(Cl)c(Cl)cc2nc1O)N1CCC[C@H]1Cc1cc(Cl)cc(Cl)c1] | 471.16 | 468 [M − H]− | 0.004 | 3.8 |
| 8-12 | 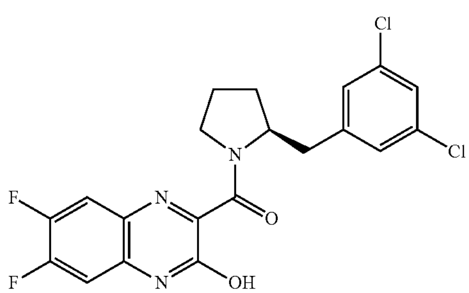 [SMILES: O=C(c1nc2cc(F)c(F)cc2nc1O)N1CCC[C@H]1Cc1cc(Cl)cc(Cl)c1] | 438.25 | 436 [M − H]− | 0.0013 | 3.2 |
| 8-13 | 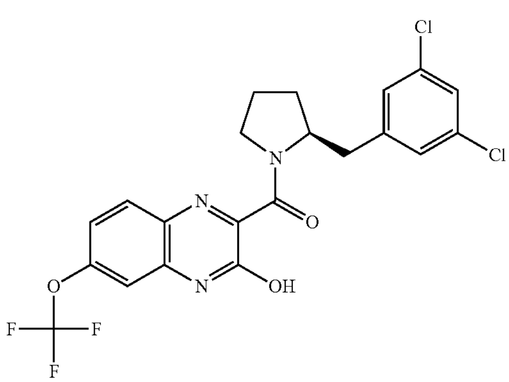 [SMILES: O=C(c1nc2ccc(OC(F)(F)F)cc2nc1O)N1CCC[C@H]1Cc1cc(Cl)cc(Cl)c1] | 486.27 | 484 [M − H]− | | 7.7 |

-continued

| ID | Structure | MW | MS m/z (M⁺ + H) | FABP4 TdF Kd uM | Retention Time (min) |
|---|---|---|---|---|---|
| 8-14 | 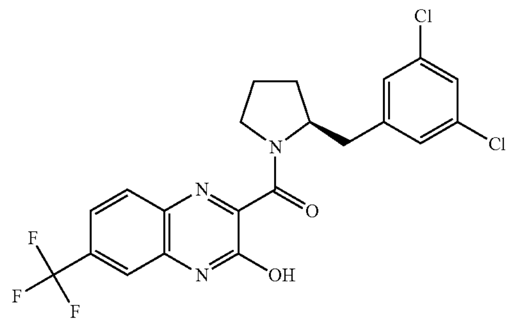 [SMILES: O=C(c1nc2ccc(C(F)(F)F)cc2nc1O)N1CCC[C@H]1Cc1cc(Cl)cc(Cl)c1] | 470.27 | 468 [M − H]⁻ | | 7.6 |
| 8-15 | 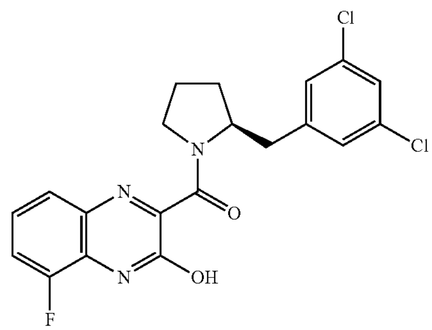 | 420.26 | 418 [M − H]⁻ | | 7 |
| 8-16 | 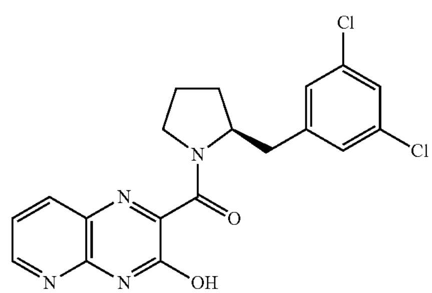 [SMILES: O=C(c1nc2cccnc2nc1O)N1CCC[C@H]1Cc1cc(Cl)cc(Cl)c1] | 403.26 | 401 [M − H]⁻ | | 6.4 |
| 8-17 | 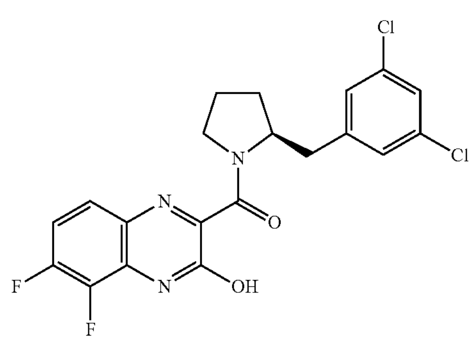 [SMILES: O=C(c1nc2ccc(F)c(F)c2nc1O)N1CCC[C@H]1Cc1cc(Cl)cc(Cl)c1] | 438.26 | 436 [M − H]⁻ | | 7.1 |

| ID | Structure | MW | MS m/z (M⁺ + H) | FABP4 TdF Kd uM | Retention Time (min) |
|---|---|---|---|---|---|
| 8-18 | 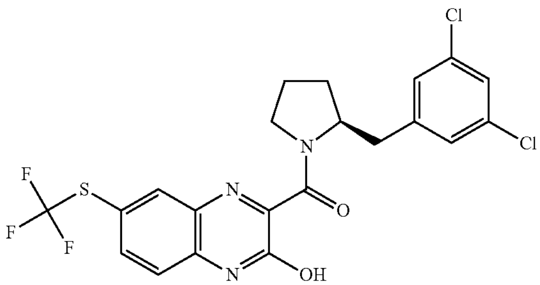 [SMILES: O=C(c1nc2cc(SC(F)(F)F)ccc2nc1O)N1CCC[C@H]1Cc1cc(Cl)cc(Cl)c1] | 502.34 | 500 [M − H]⁻ | | 8.1 |

Preparation of (S)-(2-((3-chlorophenyl)(hydroxy)methyl)pyrrolidin-1-yl)(3-hydroxyquinoxalin-2-yl)methanone (8-7)

8-7

Compound 8-7 was prepared using Step 1 above replacing (3,5-dichlorophenyl)magnesium bromide with (3-chlorophenyl)magnesium bromide.

Preparation of (S)-(2-(3-chlorobenzyl)pyrrolidin-1-yl)(3-hydroxyquinoxalin-2-yl)methanone (8-8)

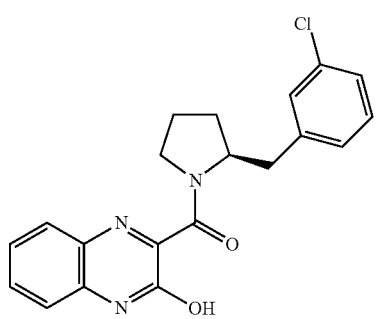

8-8

Compound 8-8 was prepared using Step 1 through Step 4 above replacing (3,5-dichlorophenyl)magnesium bromide with (3-chlorophenyl)magnesium bromide.

Preparation of (R)-(2-(3-chlorobenzyl)pyrrolidin-1-yl)(3-hydroxyquinoxalin-2-yl)methanone (8-9)

8-9

Compound 8-9 was prepared using Step 1 through Step 4 above replacing (S)-Boc-2-prolinal 8-1 and (3,5-dichlorophenyl)magnesium bromide with (R)-Boc-2-prolinal and (3-chlorophenyl)magnesium bromide respectively.

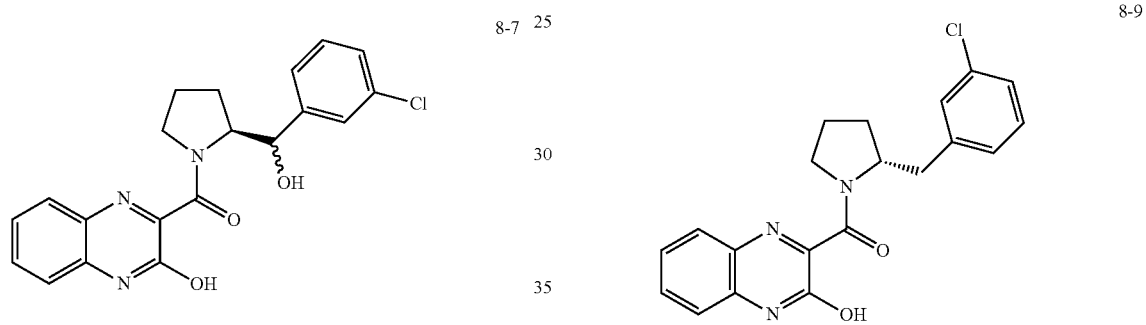

| ID | Structure | MW | FABP4 TdF Kd uM | FABP5 TdCD Kd uM |
|---|---|---|---|---|
| 8-7 | 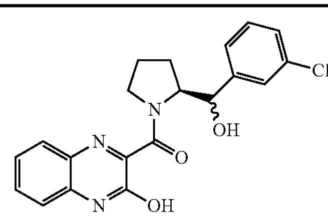 | 383.83 | 7.1 | |
| 8-8 | 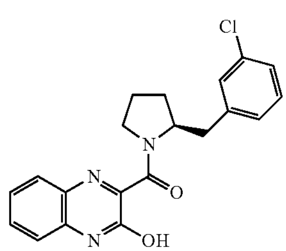 [SMILES: O=C(c1nc2ccccc2nc1O)N1CCC[C@H]1Cc1cccc(Cl)c1] | 367.83 | 0.3 | 0.5 |

143

-continued

| ID | Structure | MW | FABP4 TdF Kd uM | FABP5 TdCD Kd uM |
|---|---|---|---|---|
| 8-9 | 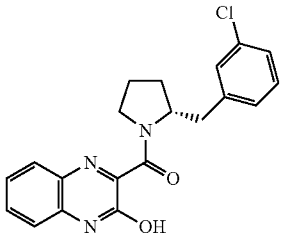 [SMILES: O=C(c1nc2ccccc2nc1O)N1CCC[C@@H]1Cc1cccc(Cl)c1] | 367.83 | 5 | |

General Method 9

Preparation of (S)-(2-(3-chlorobenzyl)pyrrolidin-1-yl)(3-hydroxy-6-phenylpyrazin-2-yl)methanone (9-6)

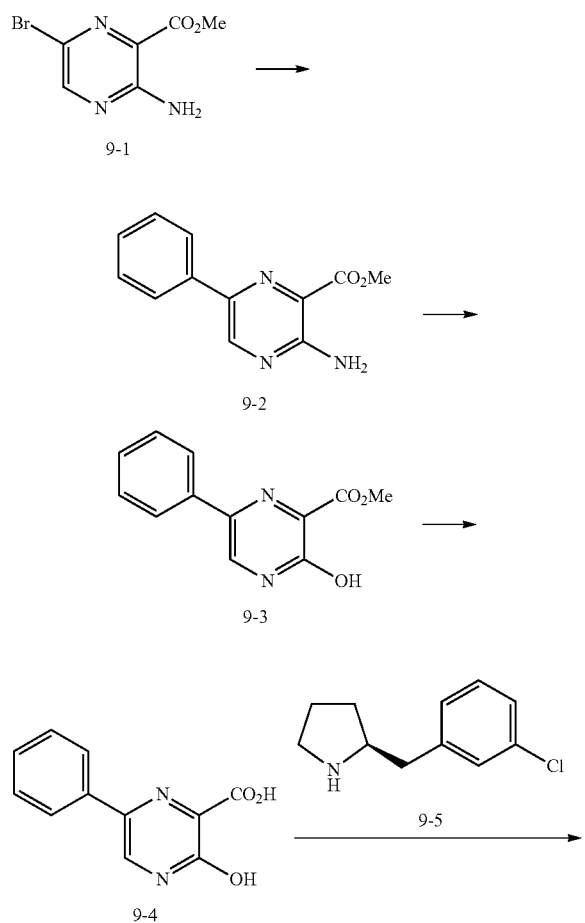

144

-continued

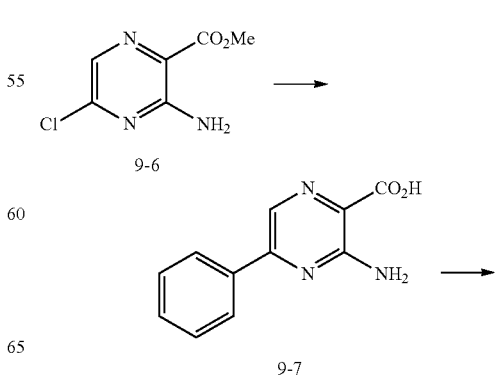

9-6

Step 1: Methyl 3-amino-6-bromopyrazine-2-carboxylate 9-1 (0.85 g, 3.68 mmol), phenylboronic acid (0.56 g, 3.68 mmol) and 2M aqueous sodium carbonate (7.4 mL) were mixed with toluene (8 mL) and methanol (2 mL). Palladium tetrakis(triphenylphosphine) (427 mg, 0.37 mmol) was added. The mixture was degassed and heated under nitrogen at 85° C. for 4 h. The reaction mixture was cooled to room temperature and filtered through a pad of Celite. The filtrate was concentrated and residue was separated by column chromatography (silica gel, gradient elution with DCM to 5% MeOH-DCM), to give desired product 9-2 as a yellow solid.

Step 2: Compound 9-2 (0.3 g, 1.2 mmol) was dissolved in THF (15 mL), $CH_3CN$ (2 mL) and 50% $H_2SO_4$ (0.7 mL) at 0° C. t-Butylnitrile (0.73 mL, 6.1 mmol) was added. The resulting solution was stirred at room temperature for 2 h. 5 N NaOH was added carefully to bring the mixture to basic. The aqueous layer was separated and extracted with DCM. The organic extracts were combined and the residue was purified with preparative TLC (silica gel, eluted with MeOH/DCM, 1:20, v/v) to give the desired product 9-3 as a yellow solid.

Step 3: Compound 9-3 (0.18 g, 0.78 mmol) and LiOH (98 mg, 4.1 mmol) were dissolved in THF (2 mL) and $H_2O$ (1 mL). The mixture was stirred at room temperature for 2 h, then treated with 1 N HCl. The aqueous layer was separated and extracted with DCM to give the desired product 9-4.

Step 4: Compound 9-5 was prepared using Step 1 replacing (3,5-dichlorophenyl)magnesium bromide with (3-chlorophenyl)magnesium bromide through Step 3 in General Method 8. Compound 9-6 was prepared using Step 4 in General Method 8 as described above.

Preparation of (S)-(2-(3-chlorobenzyl)pyrrolidin-1-yl)(3-hydroxy-5-phenylpyrazin-2-yl)methanone (9-10)

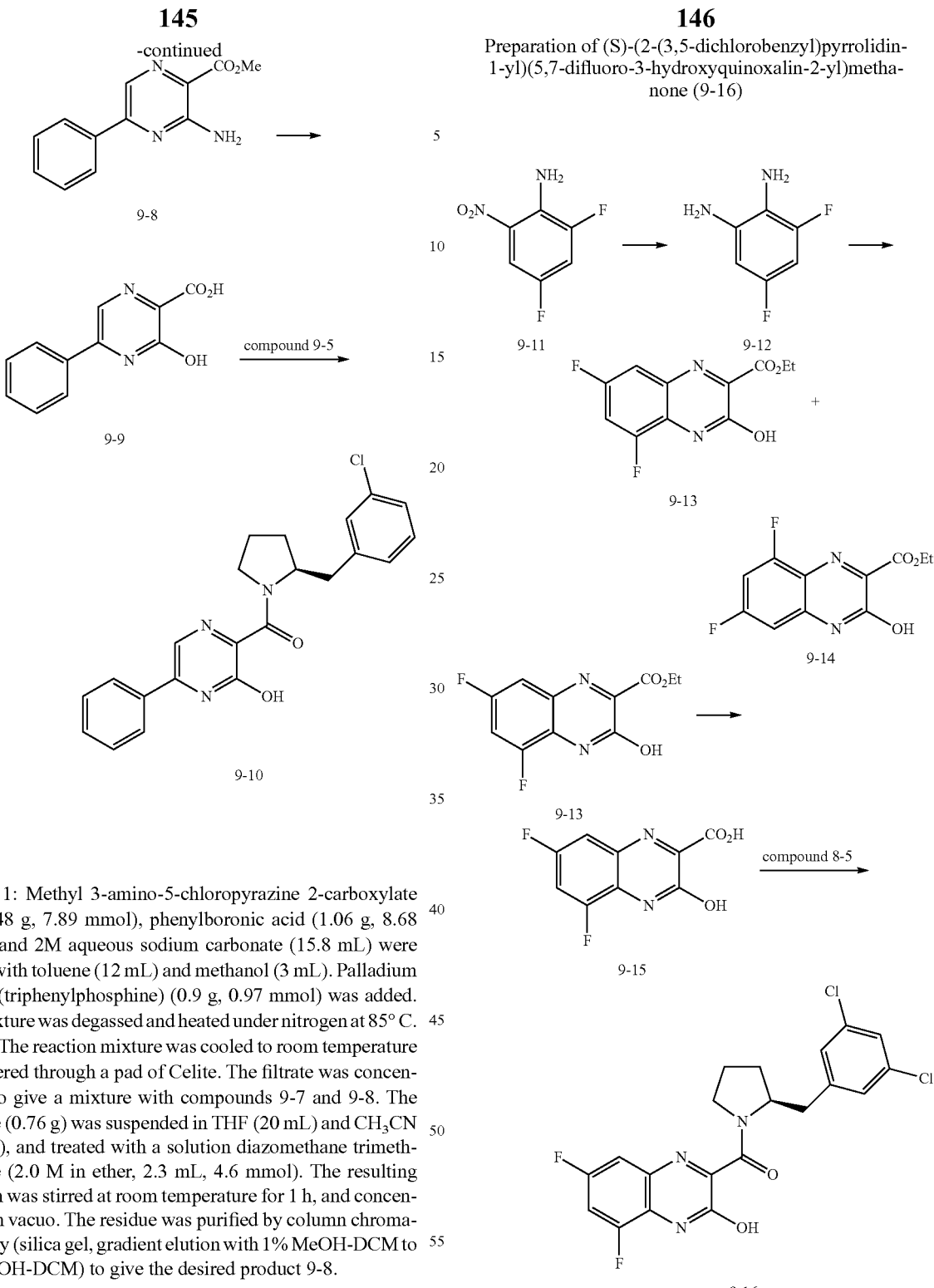

Step 1: Methyl 3-amino-5-chloropyrazine 2-carboxylate 9-6 (1.48 g, 7.89 mmol), phenylboronic acid (1.06 g, 8.68 mmol) and 2M aqueous sodium carbonate (15.8 mL) were mixed with toluene (12 mL) and methanol (3 mL). Palladium tetrakis(triphenylphosphine) (0.9 g, 0.97 mmol) was added. The mixture was degassed and heated under nitrogen at 85° C. for 4 h. The reaction mixture was cooled to room temperature and filtered through a pad of Celite. The filtrate was concentrated to give a mixture with compounds 9-7 and 9-8. The mixture (0.76 g) was suspended in THF (20 mL) and CH$_3$CN (20 mL), and treated with a solution diazomethane trimethylsilane (2.0 M in ether, 2.3 mL, 4.6 mmol). The resulting solution was stirred at room temperature for 1 h, and concentrated in vacuo. The residue was purified by column chromatography (silica gel, gradient elution with 1% MeOH-DCM to 2% MeOH-DCM) to give the desired product 9-8.

Step 2: Compound 9-8 (0.68 g, 2.97 mmol) was dissolved in THF (30 mL), CH$_3$CN (4 mL) and 50% H$_2$SO$_4$ (1.7 mL) at 0° C. t-Butylnitrile (1.53 g, 14.8 mmol) was added. The resulting solution was stirred at room temperature for 2 h. 5 N NaOH was added carefully to bring the mixture to basic. Aqueous layer was separated and washed with DCM. The aqueous layer was brought to acidic by treating with 1N HCl, and extracted with DCM to give the desired product 9-9.

Step 3: Compound 9-10 was prepared using Step 4 in General Method 8 as described above.

Preparation of (S)-(2-(3,5-dichlorobenzyl)pyrrolidin-1-yl)(5,7-difluoro-3-hydroxyquinoxalin-2-yl)methanone (9-16)

Step 1: 10% Pd/C (100 mg) was added a solution in compound 9-11 (500 mg, 2.87 mmol) in EtOH (50 mL). The resulting suspension was stirred under a H$_2$ balloon at room temperature for 2 h. The mixture was filtered through Celite and the filtrate was concentrated in vacuo to give desired product 9-12.

Step 2: Compound 9-12 (0.35 g, 2.43 mmol) and diethyl ketomalonate (0.39 mL, 2.55 mmol) were mixed in EtOH (7 mL). The resulting solution was heated to reflux for 5 h. The mixture was cooled to room temperature and concentrated. The residue was purified by column chromatography (silica gel, eluted with 5% EtOAc/hexanes, 20% EtOAc/hexanes, 30% EtOAc/hexanes) to give the desired compound 9-13 and 9-14.

Step 3: Compound 9-13 (190 mg, 0.75 mmol) was dissolved in THF (4 mL) and water (2 mL), and LiOH (125 mg, 2.99 mmol) was added. The resulting solution was stirred at 50° C. for 30 min. The mixture was cooled to 0° C. and 12 N $HCl_{(aq.)}$ was added. The precipitate was collected by filtration to give the desired product 9-15 as a yellow solid.

Step 4: Compound 9-16 was prepared using Step 4 in General Method 8 as described above.

Preparation of (S)-(2-(3,5-dichlorobenzyl)pyrrolidin-1-yl)(6,8-difluoro-3-hydroxyquinoxalin-2-yl)methanone (9-18)

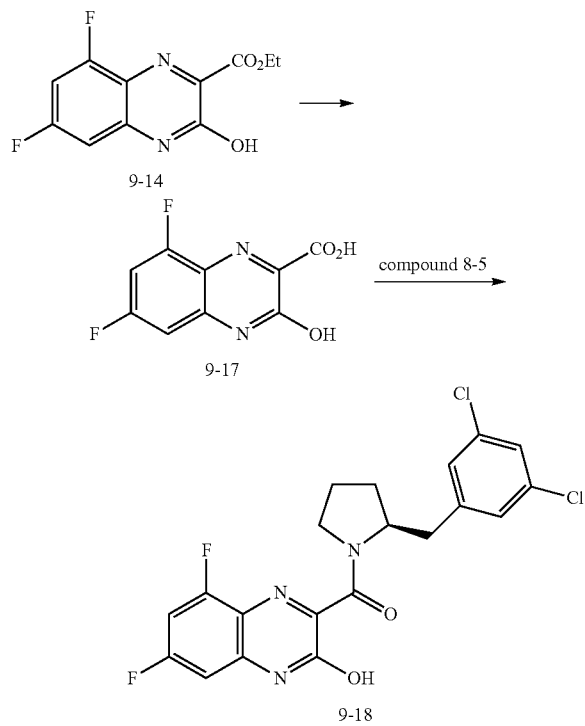

Compound 9-18 was prepared using the procedures as described above.

Preparation of (S)-(3-amino-6-phenylpyrazin-2-yl)(2-(3-chlorobenzyl)pyrrolidin-1-yl)methanone (9-19)

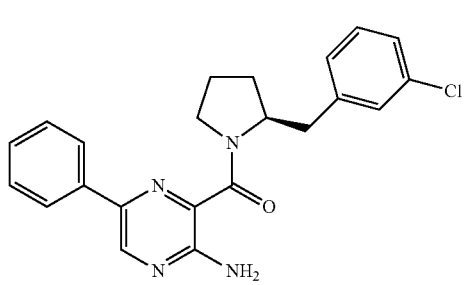

Compound 9-19 was prepared from the hydrolysis of 9-2 followed by the amide coupling of 9-5.

| ID | Structure | MW | FABP4 TdF Kd uM |
|---|---|---|---|
| 9-16 | 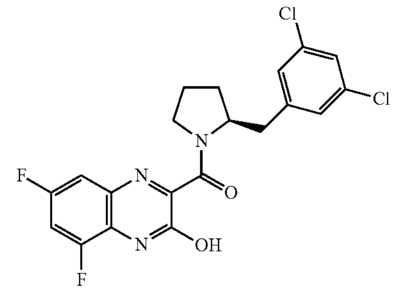 [SMILES: O=C(c1nc2cc(F)cc(F)c2nc1O)N1CCC[C@H]1Cc1cc(Cl)cc(Cl)c1] | 438.25 | 0.007 |
| 9-18 | 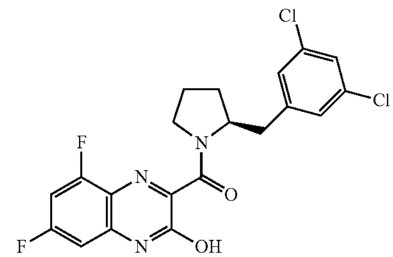 [SMILES: O=C(c1nc2c(F)cc(F)cc2nc1O)N1CCC[C@H]1Cc1cc(Cl)cc(Cl)c1] | 438.25 | 0.05 |

Assay

An assay to demonstrate FABP inhibitory activity of the inventive compounds is described below:

Theoretical basis for TdF-based ligand binding affinity constant

The derivation of TdF-based ligand binding affinity constant ($K_d$) followed closely those previously formulated by Brandts and Lin, *Biochemistry* 29 (1990) 6927-6940. In brief, the binding constant of the ligand at the $T_m$ is expressed as below:

$$K_L(T_m) = \frac{\left\{ \exp\left\{ -\left(\frac{\Delta H_u(T_0)}{R}\right)\left(\frac{1}{\frac{T_m-1}{T_0}}\right) + \left(\frac{\Delta Cp_u}{R}\right)\left[\ln\left(\frac{T_m}{T_0}\right) + \left(\frac{T_0}{T_m}\right) - 1\right]\right\} - 1\right\}}{[L_{Tm}]}$$

where $T_0$ is the midpoint of unfolding for unliganded protein and $T_m$ is the midpoint of unfolding in presence of ligand. $[L_{Tm}]$ is free ligand at $T_m$. The $\Delta H_u$ and $\Delta Cp_u$ are the enthalpy of unfolding and heat capacity change of unfolding for the protein respectively. The $\Delta C_{Pu}$ is proportional to the size of protein and is an approximate quantity in the above equation (empirically, $\Delta Cp_u$=(MW of protein/115)*14 cal/mol*K). Following algorithm derived by Mayhood et al, (*Analytical Biochemistry* 345 (2005) 187-197), the $T_0$ and $\Delta H_u$ can be determined separately from nonlinear regression fitting the temperature dependent protein alone curve to the following equation:

$$F(T) = \frac{(Y_n + m_n(T)) + (Y_u + m_u(T))\exp\left\{-\left(\frac{\Delta H_u}{RT}\right)\left(1 - \frac{T}{T_0}\right)\right\}}{1 + \exp\left\{-\left(\frac{\Delta H_u}{RT}\right)\left(1 - \frac{T}{T_0}\right)\right\}}$$

Where F(T) is the observed fluorescence intensity at any temperature T, $Y_n$ and $Y_u$ are the predicted fluorescence intensities for fully folded and unfolded protein, respectively; $m_n$ and $m_u$ are slope correction for changes in $Y_n$ and $Y_u$ with respect to changes in temperature (analogously replace $T_0$ with $T_m$ in the above equation for liganded protein to yield $T_m$). The nonlinear regression fitting in general readily reaches convergence by properly constraining the initial values for the fitting parameters (e.g. the initial "guess" for the $\Delta H_u$ was constrained to 120 kcal/mol; initial $Y_n$ and $m_r$, were set to 1 and zero to best represent the melting curve along the low temperature region; negative slope of –0.5 was initially chosen for $m_u$; initial $T_m$ was also constrained to 50° C.).

Finally, the ligand binding affinity constant at any temperature T (i.e. 25° C.) can be thermodynamically connected to the preceding $K_L(T_m)$ via $$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

(see Brandts et al and Mayhood et al, shown above) where $\Delta H_L$ (T) is the van't Hoff enthalpy of ligand binding at temperature T and $\Delta Cp_L$ is the heat capacity upon ligand binding. For simplicity, the $\Delta Cp_L$ and $\Delta H_L$ (T) were set to zero and –7 kcal/mol respectively. (The $\Delta Cp_L$ accounts for minimal portion of total protein-ligand binding energetics and is therefore set to zero (For example, see Hossein Naghibi et al, *Proc. Natl. Acad. Sci.* 92, 5597-5599 (1995), where $\Delta Cp_L$ was estimated to ~2% of $\Delta H_L$ at 25° C. obtained from calorimetric study of binding RNase A and 2'-CMP)). Data are provided for the compounds that are disclosed.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound of the formula I:

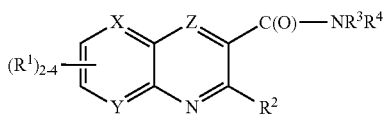

I or a pharmaceutically acceptable salt thereof, wherein:
wherein X and Y represent carbon atoms and Z represents a nitrogen atom;
each $R^1$ is H or is selected from the group consisting of: halo, CN, OH, $C_{1-6}$alkyl, $OC_{1-6}$alkyl, halo$C_{1-6}$alkyl, $OC_{1-6}$haloalkyl, $S(O)_xC_{1-6}$alkyl, and $S(O)_xC_{1-6}$haloalkyl, wherein x is 0, 1 or 2;
$R^2$ represents OH, halo, $C_{1-6}$alkyl, $OC_{1-6}$alkyl, $C_{1-6}$haloalkyl, $OC_{1-6}$haloalkyl, $NH_2$, $NHC_{1-6}$alkyl and $N(C_{1-6}$alkyl$)_2$, the alkyl portions of $NHC_{1-6}$alkyl and $N(C_{1-6}$alkyl$)_2$ being optionally substituted with 1-3 halo atoms;
$R^3$ and $R^4$ taken together with the N atom to which they are attached represent a 4-7 membered ring consisting of carbon atoms and 1 N atom, wherein the 4-7 membered ring is substituted with 1-3 groups selected from $R^b$;
each $R^b$ is selected from the group consisting of:
a) $C_{1-6}$alkyl optionally substituted with 1-2 Aryl, Heteroaryl, Heterocyclyl, Cycloalkyl, O—$C_{1-6}$Alkyl, O-Aryl, O-Heteroaryl, NH—$C_{1-6}$Alkyl, NH-Aryl, and NH-Heteroaryl groups, the Aryl, Heteroaryl, Heterocyclyl and Alkyl portions being further optionally substituted with 1-3 $C_{1-3}$alkyl, halo, $OC_{1-6}$alkyl, $C_{1-6}$haloalkyl and $OC_{1-6}$haloalkyl groups;
b) $CO_2C_{1-6}$Alkyl, $CO_2$-Aryl, $CO_2$-Heteroaryl, and $CO_2C_{3-6}$Cycloalkyl, each being optionally substituted with 1-2 $C_{1-3}$ alkyl, halo, Aryl, Heteroaryl, Heterocyclyl, Cycloalkyl, O—$C_{1-6}$Alkyl, NH—$C_{1-6}$Alkyl, and NH-Aryl groups, the Aryl, Heteroaryl, and Heterocyclyl portions, and the alkyl portions of O—$C_{1-6}$Alkyl and NH—$C_{1-6}$Alkyl being further optionally substituted with 1-3 $C_{1-6}$alkyl, halo, $OC_{1-6}$alkyl, halo$C_{1-6}$alkyl and $OC_{1-6}$haloalkyl groups;
c) Aryl, Heteroaryl, Heterocyclyl, Cycloalkyl, O—$C_{1-6}$Alkyl, NH—$C_{1-6}$Alkyl, and NH-Aryl, each being optionally substituted with 1-3 alkyl, halo, $OC_{1-6}$alkyl, halo$C_{1-6}$alkyl and $OC_{1-6}$haloalkyl groups;
or 2 $R^b$ groups are taken together and represent a fused phenyl ring, optionally substituted with 1-3 halo atoms or $C_{1-6}$alkyl groups.

2. The compound of claim 1 or a pharmaceutically acceptable salt thereof wherein each $R^1$ is selected from H, F, Cl and I.

3. The compound of claim 1 or a pharmaceutically acceptable salt thereof wherein 1-2 $R^1$ groups are selected from F and Cl, and the remainder of the $R^1$ groups are selected from H, F, Cl, Br, I, CN, $C_{1-3}$alkyl, halo$C_{1-3}$alkyl, $OC_{1-3}$alkyl, $OC_{1-3}$haloalkyl, $SC_{1-3}$alkyl, $SC_{1-3}$haloalkyl, $SO_2C_{1-3}$alkyl and $SO_2C_{1-3}$haloalkyl.

4. The compound of claim 1 or a pharmaceutically acceptable salt thereof wherein $R^2$ is selected from OH, $NH_2$, $C_1$, $C_{1-3}$alkyl and $C_{1-3}$haloalkyl.

5. The compound of claim 1 or a pharmaceutically acceptable salt thereof, wherein $R^3$ and $R^4$ are taken together with the N atom to which they are attached represent a 4, 5, or 6 membered ring consisting of carbon atoms and 1 N atom, wherein the 4, 5 or 6 membered ring is substituted with 1-2 groups selected from $R^b$;
and each $R^b$ is selected from the group consisting of:
a) $C_{1-3}$alkyl optionally substituted with 1 Aryl, Heteroaryl, Heterocyclyl, Cycloalkyl, NH—$C_{1-3}$Alkyl, NH-Aryl, or NH-Heteroaryl groups, the Aryl, Heteroaryl, Heterocyclyl and Alkyl portions being further optionally substituted with 1-3 $C_{1-3}$alkyl, halo, $OC_{1-3}$alkyl, $C_{1-3}$haloalkyl and $OC_{1-}$3haloalkyl groups;
b) $CO_2C_{1-3}$Alkyl, $CO_2$-Aryl, $CO_2$-Heteroaryl, and $CO_2C_{3-6}$Cycloalkyl, each being optionally substituted with 1 $C_{1-3}$Alkyl, halo, Aryl, Heteroaryl, Heterocyclyl, Cycloalkyl, O—$C_{1-3}$Alkyl, NH—$C_{1-3}$Alkyl, and NH-Aryl group, the Aryl, Heteroaryl, and Heterocyclyl portions, and the Alkyl portions of O—$C_{1-3}$Alkyl and NH—$C_{1-3}$Alkyl being further optionally substituted with 1-3 $C_{1-3}$alkyl, halo, $OC_{1-3}$alkyl, halo$C_{1-3}$alkyl and $OC_{1-3}$haloalkyl groups;

and c) Aryl, Heteroaryl, Heterocyclyl, Cycloalkyl, O—$C_{1-3}$ Alkyl, NH—$C_{1-3}$Alkyl, and NH-Aryl, each being optionally substituted with 1-3 alkyl, halo, $OC_{1-3}$alkyl, halo$C_{1-3}$alkyl and $OC_{1-3}$haloalkyl groups;

or 2 $R^b$ groups are taken together and represent a fused phenyl ring, optionally substituted with 1-3 halo atoms.

6. The compound of claim 1 or a pharmaceutically acceptable salt thereof wherein:

each $R^1$ is selected from H, F, Cl and I, or 1-2 $R^1$ groups are selected from F and Cl, and the remainder of the $R^1$ groups are selected from H, F, Cl, Br, I, CN, $C_{1-3}$alkyl, halo$C_{1-3}$alkyl, $OC_{1-3}$alkyl, $OC_{1-3}$haloalkyl, $SC_{1-3}$alkyl, $SC_{1-3}$haloalkyl, $SO_2C_{1-3}$alkyl and $SO_2C_{1-3}$haloalkyl;

$R^2$ is selected from OH, $NH_2$, $C_1$, $C_{1-3}$alkyl and $C_{1-3}$haloalkyl;

$R^3$ and $R^4$ considered together with the N atom to which they are attached represent a 4, 5, or 6 membered ring consisting of carbon atoms and 1 N atom, wherein the 4, 5 or 6 membered ring is substituted with 1-2 groups selected from $R^b$;

each $R^b$ is selected from the group consisting of:

a) $C_{1-3}$alkyl optionally substituted with 1 Aryl, Heteroaryl, Heterocyclyl, Cycloalkyl, NH—$C_{1-3}$Alkyl, NH-Aryl, or NH-Heteroaryl groups, the Aryl, Heteroaryl, Heterocyclyl and Alkyl portions being further optionally substituted with 1-3 $C_{1-3}$alkyl, halo, $OC_{1-3}$alkyl, $C_{1-3}$haloalkyl and $OC_{1-3}$ haloalkyl groups;

b) $CO_2C_{1-3}$Alkyl, $CO_2$-Aryl, $CO_2$-Heteroaryl, and $CO_2$ $C_{3-6}$Cycloalkyl, each being optionally substituted with 1 $C_{1-3}$Alkyl, halo, Aryl, Heteroaryl, Heterocyclyl, Cycloalkyl, O—$C_{1-3}$Alkyl, NH—$C_{1-3}$Alkyl, and NH-Aryl group, the Aryl, Heteroaryl, and Heterocyclyl portions, and the Alkyl portions of O—$C_{1-3}$Alkyl and NH—$C_{1-3}$Alkyl being further optionally substituted with 1-3 $C_{1-3}$alkyl, halo, $OC_{1-3}$alkyl, halo$C_{1-3}$alkyl and $OC_{1-3}$haloalkyl groups;

and c) Aryl, Heteroaryl, Heterocyclyl, Cycloalkyl, O—$C_{1-3}$ Alkyl, NH—$C_{1-3}$Alkyl, and NH-Aryl, each being optionally substituted with 1-3 alkyl, halo, $OC_{1-3}$alkyl, halo$C_{1-3}$alkyl and $OC_{1-3}$haloalkyl groups;

or 2 $R^b$ groups are taken together and represent a fused phenyl ring, optionally substituted with 1-3 halo atoms.

7. The compound of claim 1 selected from the compounds in Table A, Table B and Table C:

TABLE A

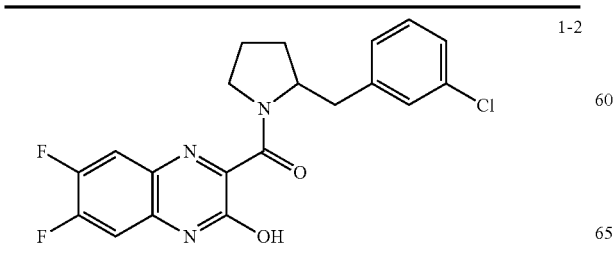

1-2

TABLE A-continued

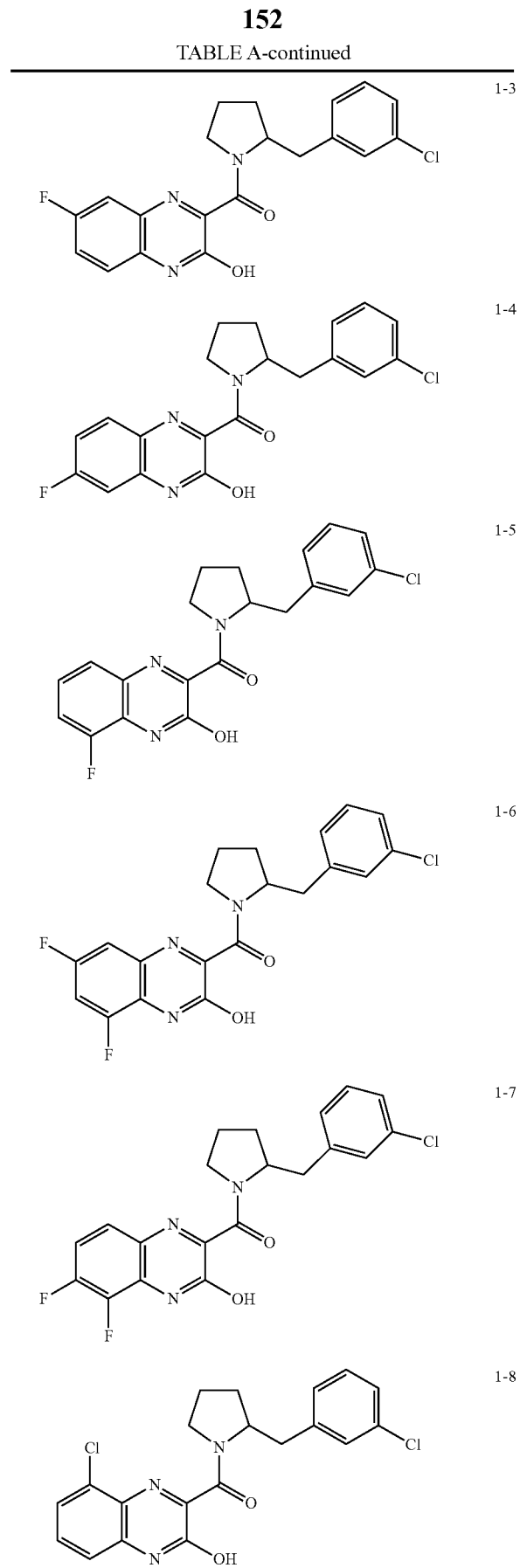

TABLE A-continued
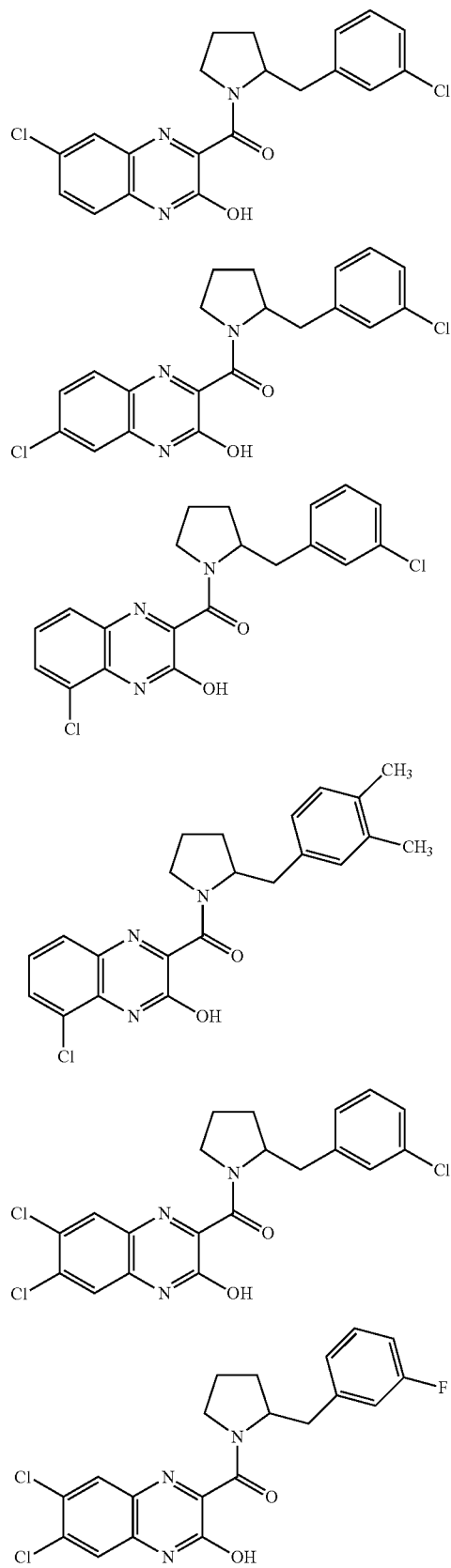
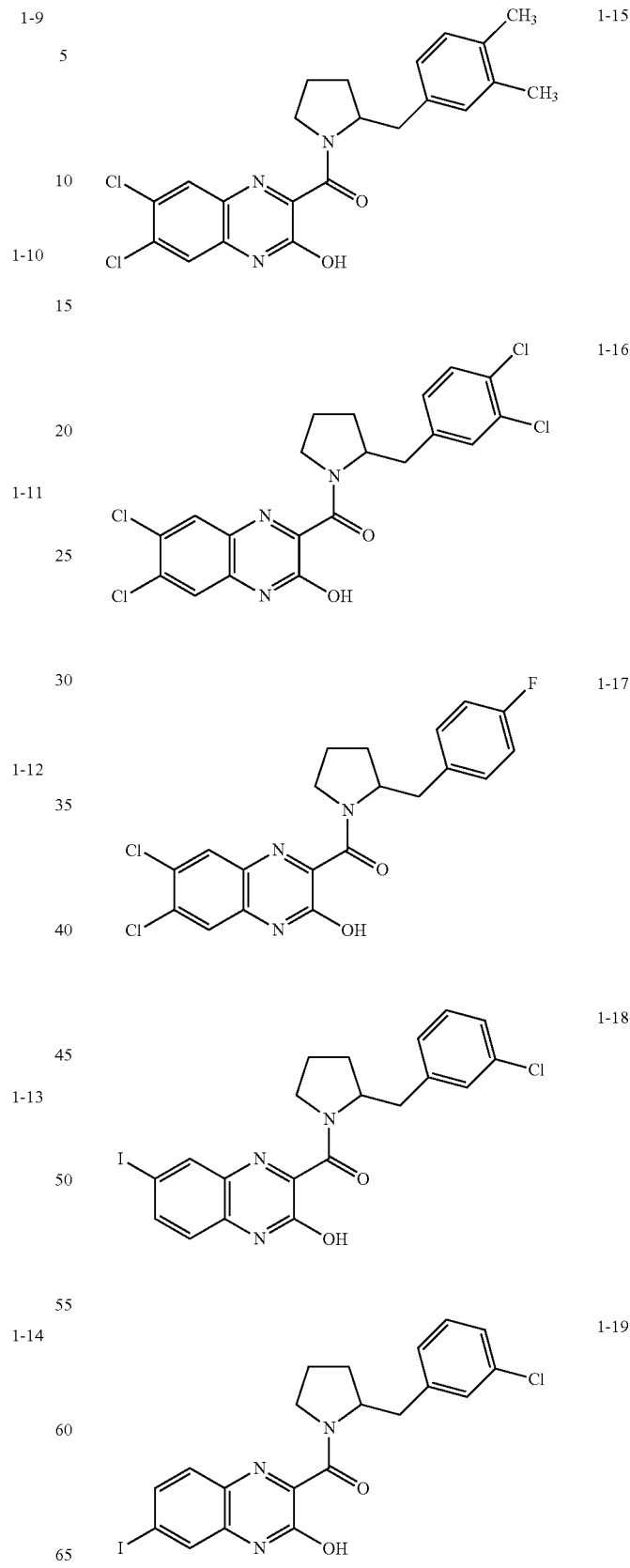

TABLE A-continued
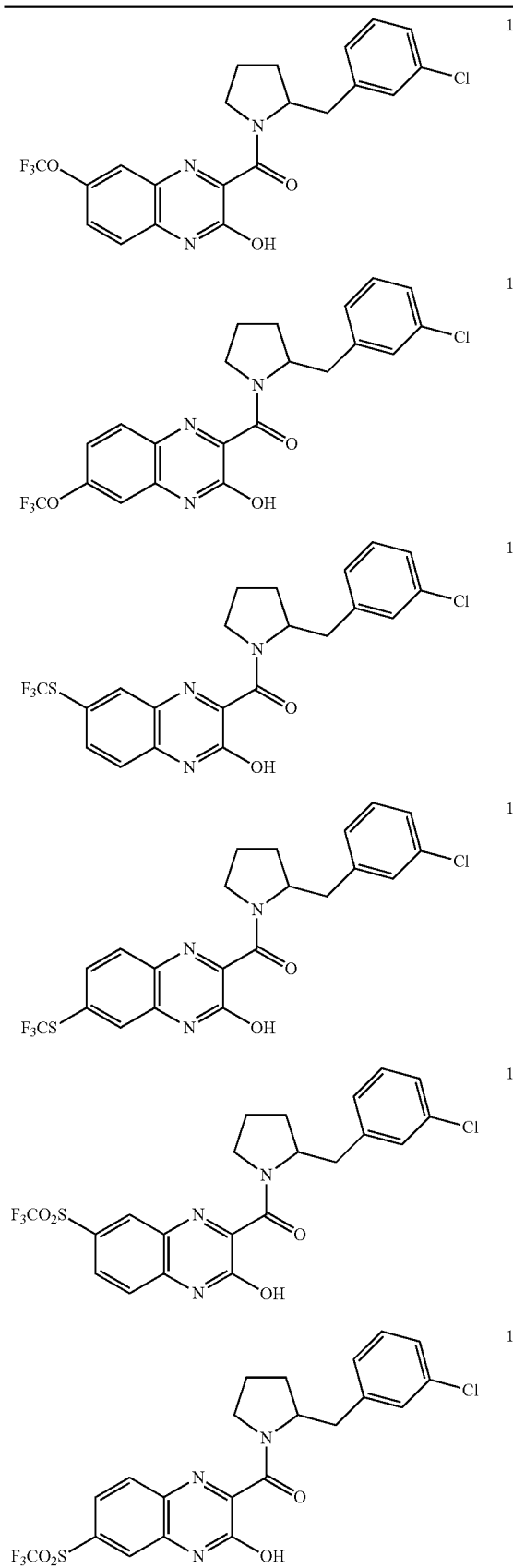
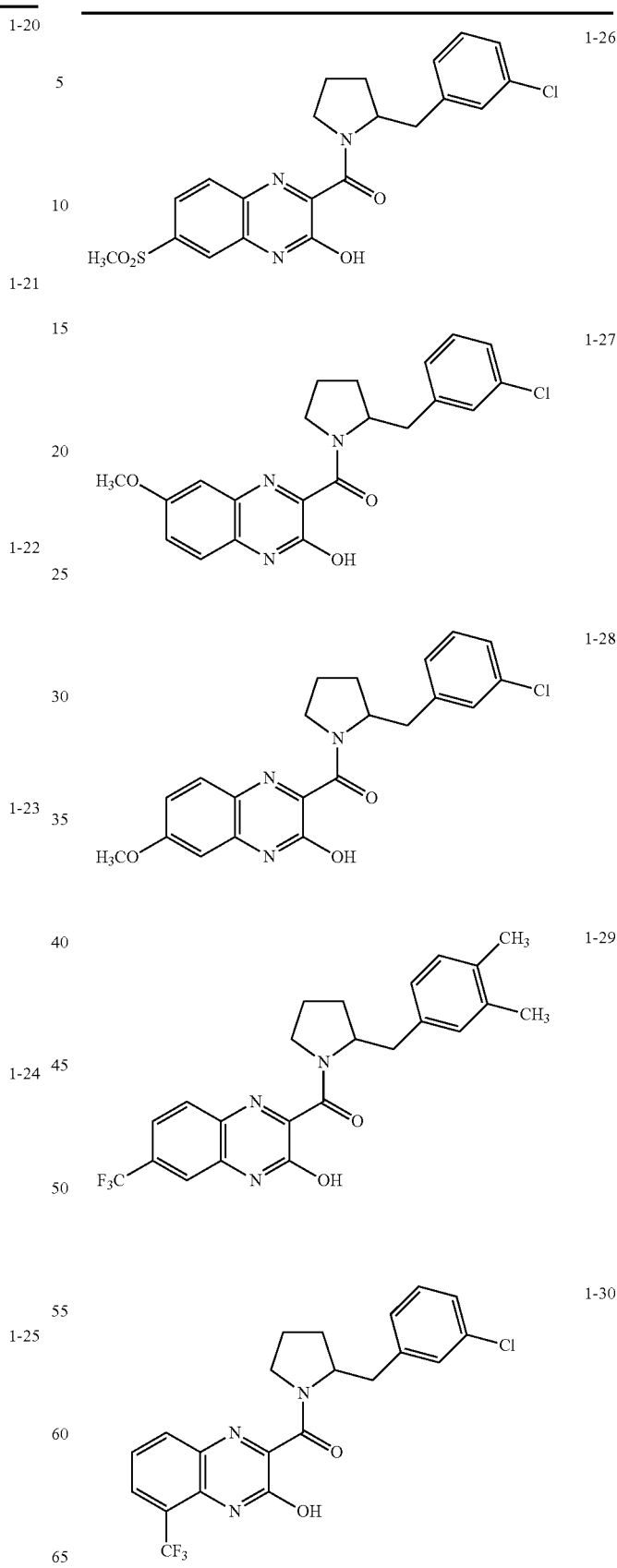

TABLE A-continued
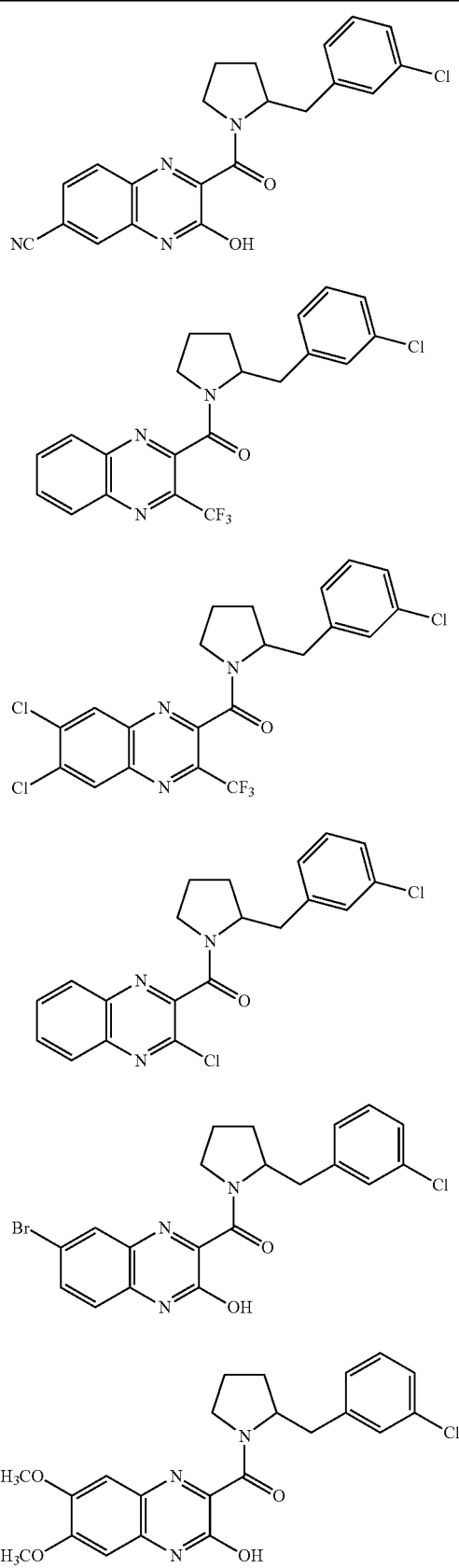
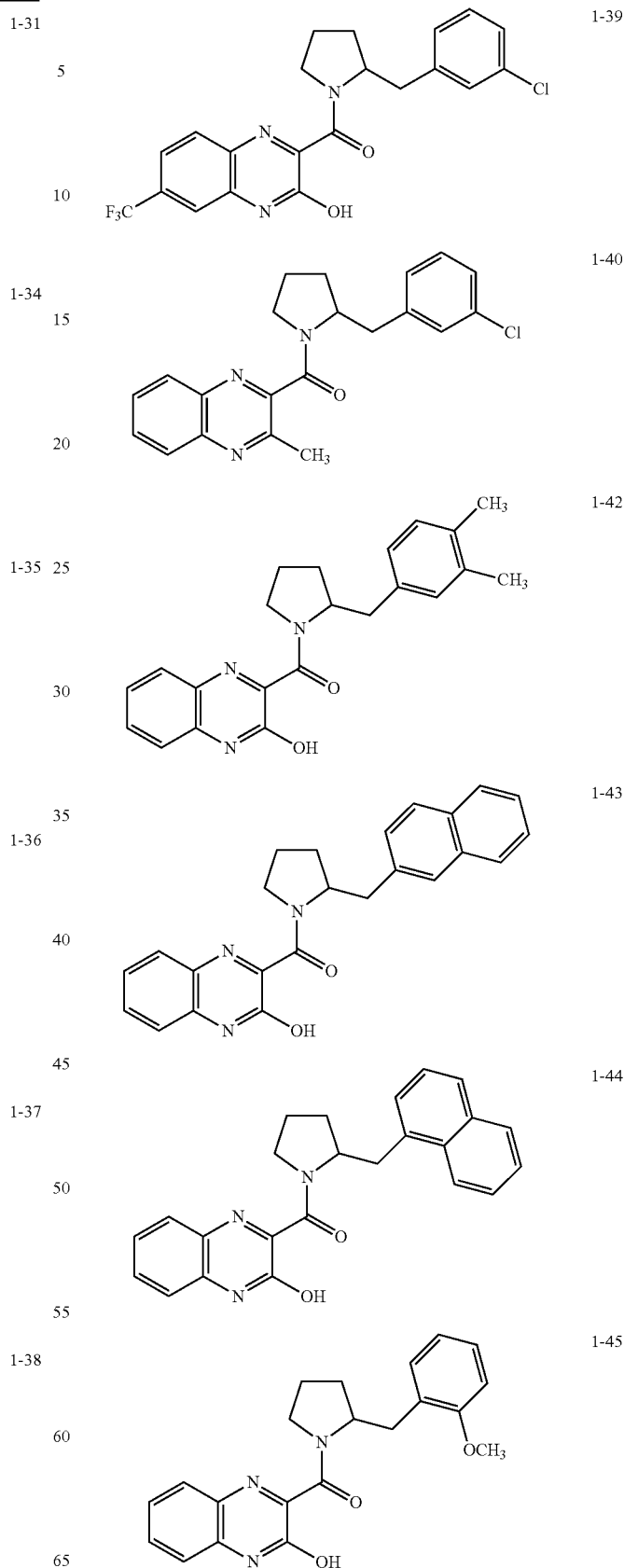

TABLE A-continued
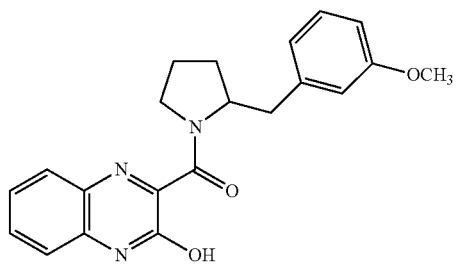 [SMILES: COc1cccc(CC2CCCN2C(=O)c2nc3ccccc3nc2O)c1] 1-46
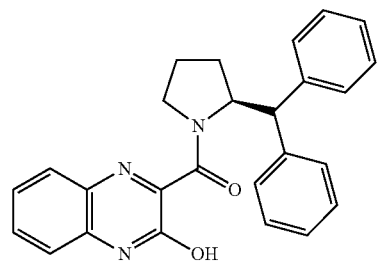 [SMILES: O=C(c1nc2ccccc2nc1O)N1CCC[C@H]1C(c1ccccc1)c1ccccc1] 1-47
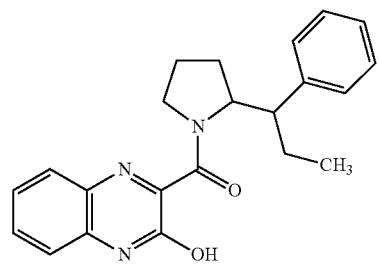 [SMILES: CCC(c1ccccc1)C1CCCN1C(=O)c1nc2ccccc2nc1O] 1-48
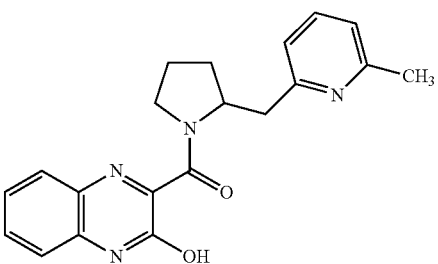 [SMILES: Cc1cccc(CC2CCCN2C(=O)c2nc3ccccc3nc2O)n1] 1-49
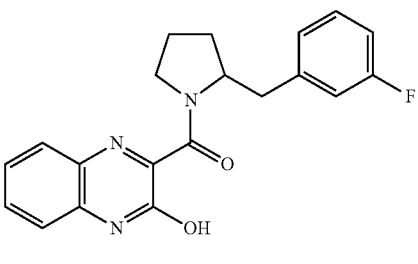 [SMILES: O=C(c1nc2ccccc2nc1O)N1CCCC1Cc1cccc(F)c1] 1-51
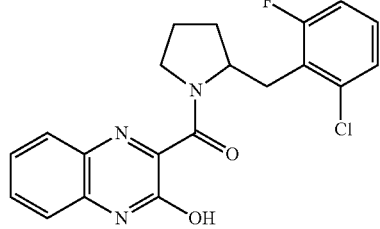 1-52
TABLE A-continued
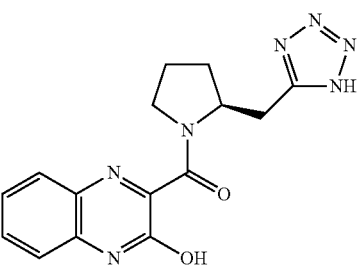 [SMILES: O=C(c1nc2ccccc2nc1O)N1CCC[C@H]1Cc1nnn[nH]1] 1-53
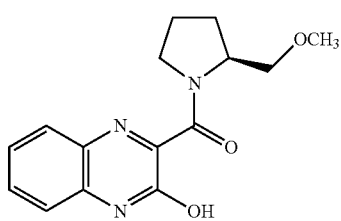 [SMILES: COC[C@@H]1CCCN1C(=O)c1nc2ccccc2nc1O] 1-54
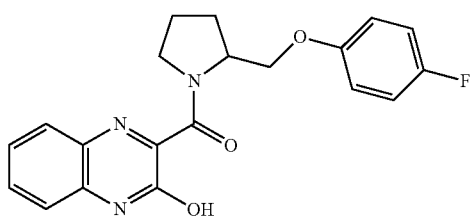 [SMILES: O=C(c1nc2ccccc2nc1O)N1CCCC1COc1ccc(F)cc1] 1-55
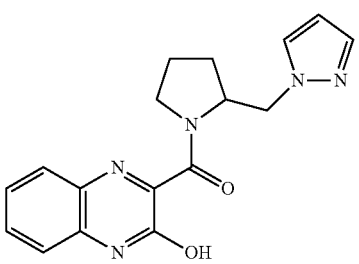 [SMILES: O=C(c1nc2ccccc2nc1O)N1CCCC1Cn1cccn1] 1-56
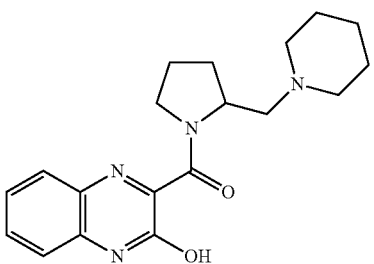 1-57
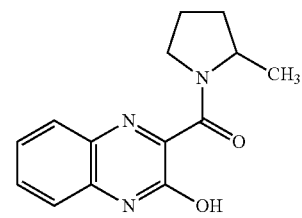 [SMILES: CC1CCCN1C(=O)c1nc2ccccc2nc1O] 1-58

TABLE A-continued
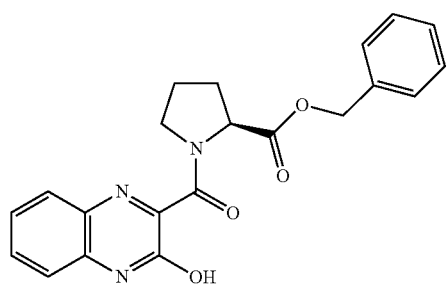 [SMILES: O=C(OCc1ccccc1)[C@@H]1CCCN1C(=O)c1nc2ccccc2nc1O]
1-59
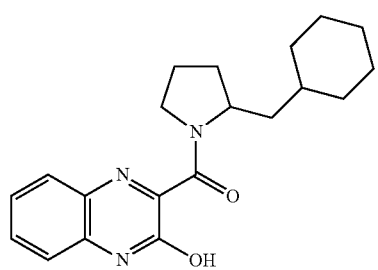
1-60
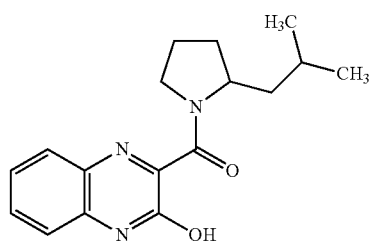 [SMILES: CC(C)CC1CCCN1C(=O)c1nc2ccccc2nc1O]
1-61
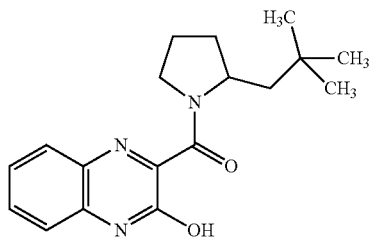 [SMILES: CC(C)(C)CC1CCCN1C(=O)c1nc2ccccc2nc1O]
1-62
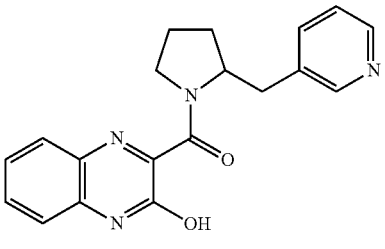
1-63
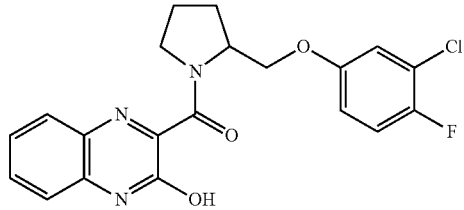 [SMILES: O=C(c1nc2ccccc2nc1O)N1CCCC1COc1ccc(F)c(Cl)c1]
1-64
TABLE A-continued
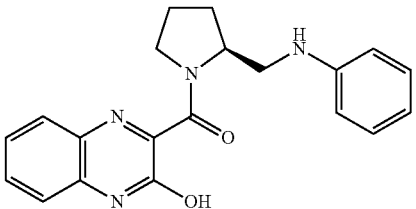 [SMILES: O=C(c1nc2ccccc2nc1O)N1CCC[C@H]1CNc1ccccc1]
1-65
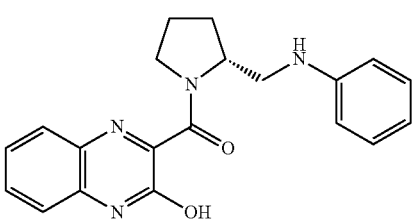 [SMILES: O=C(c1nc2ccccc2nc1O)N1CCC[C@@H]1CNc1ccccc1]
1-66
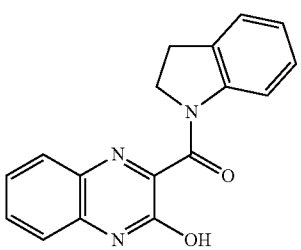 [SMILES: O=C(c1nc2ccccc2nc1O)N1CCc2ccccc21]
1-67
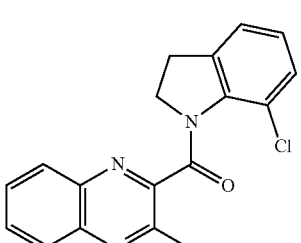
1-68
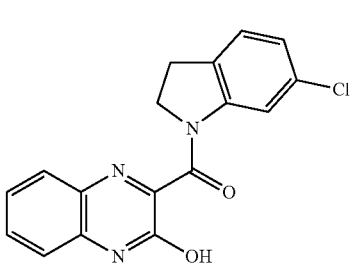 [SMILES: O=C(c1nc2ccccc2nc1O)N1CCc2ccc(Cl)cc21]
1-69
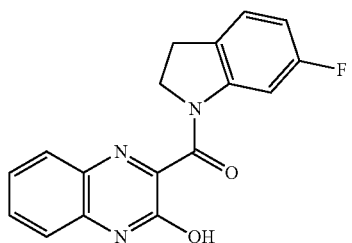 [SMILES: O=C(c1nc2ccccc2nc1O)N1CCc2ccc(F)cc21]
1-70

TABLE A-continued
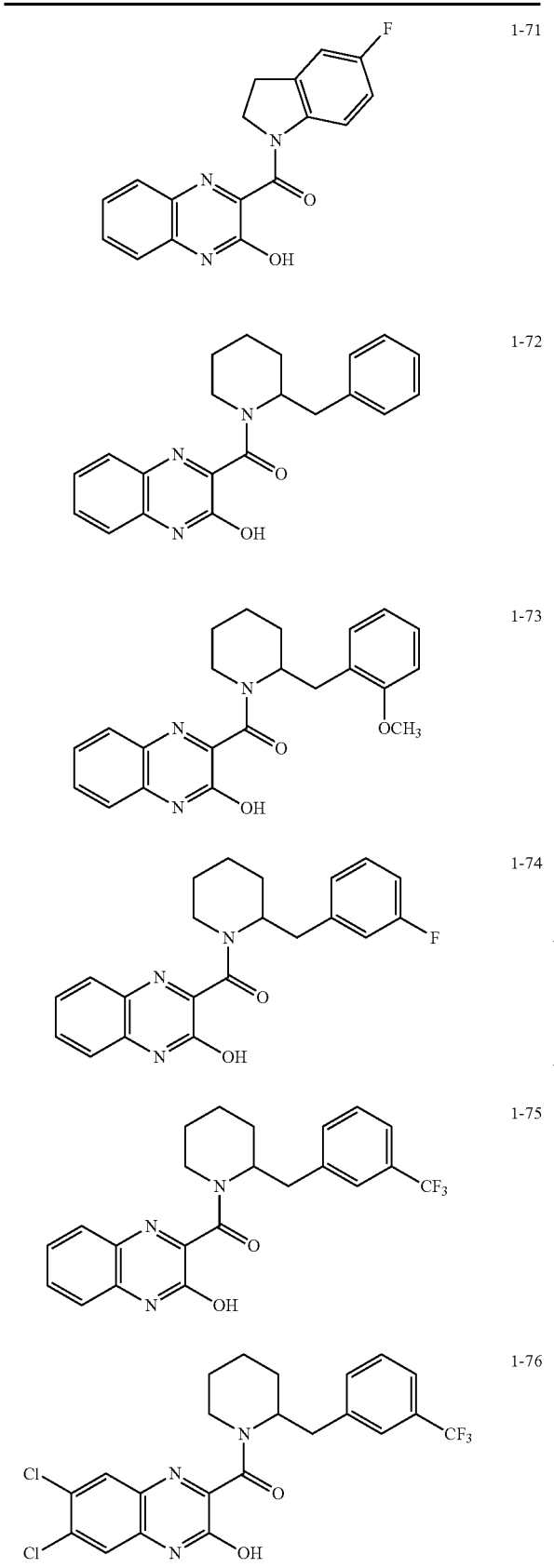
1-71
1-72
1-73
1-74
1-75
1-76
TABLE A-continued
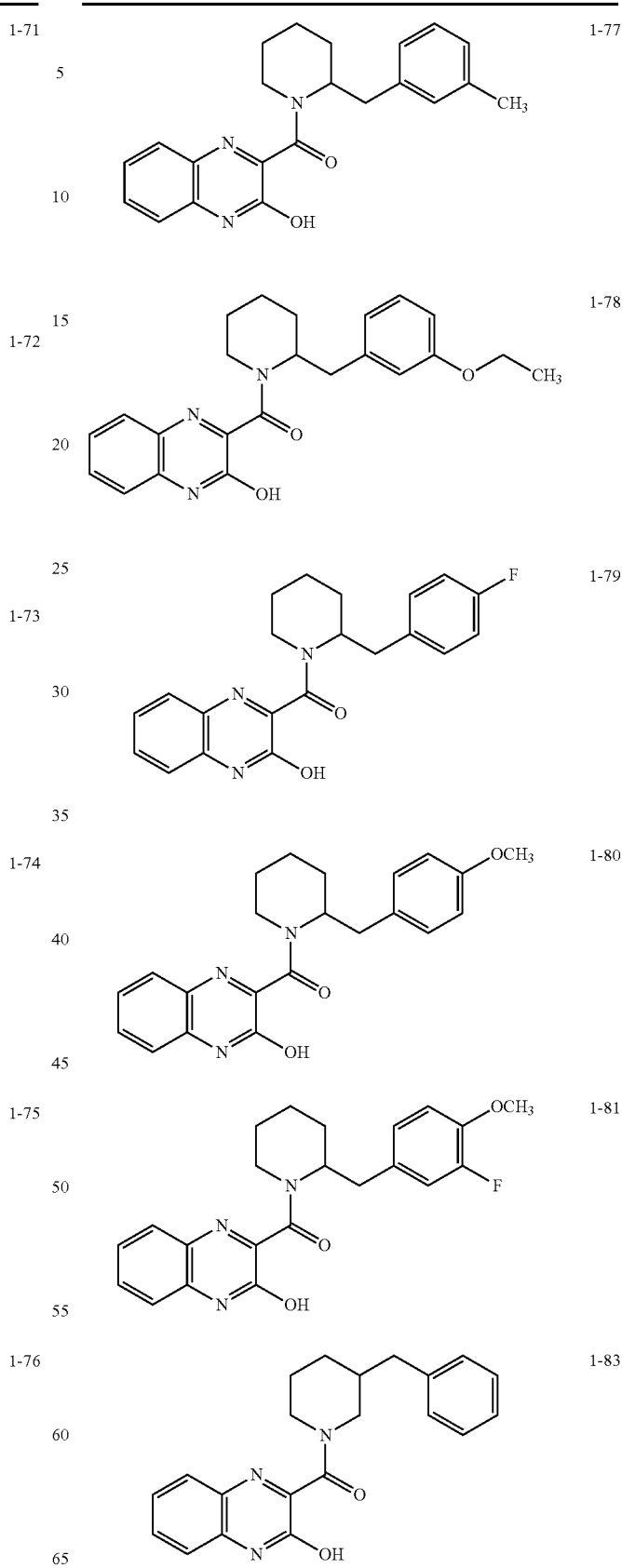
1-77
1-78
1-79
1-80
1-81
1-83

TABLE A-continued
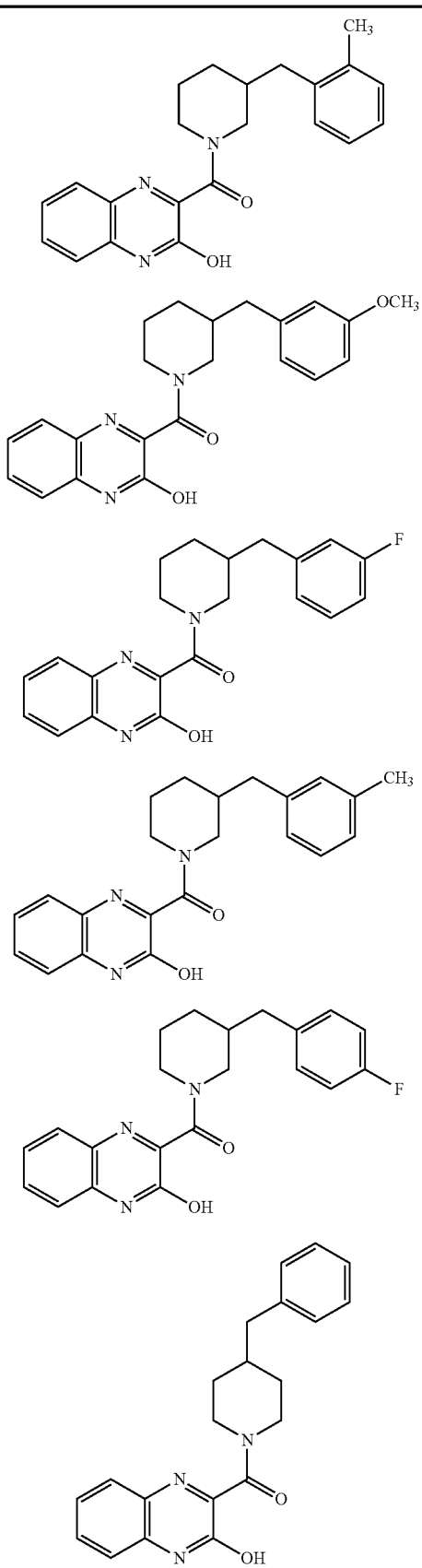
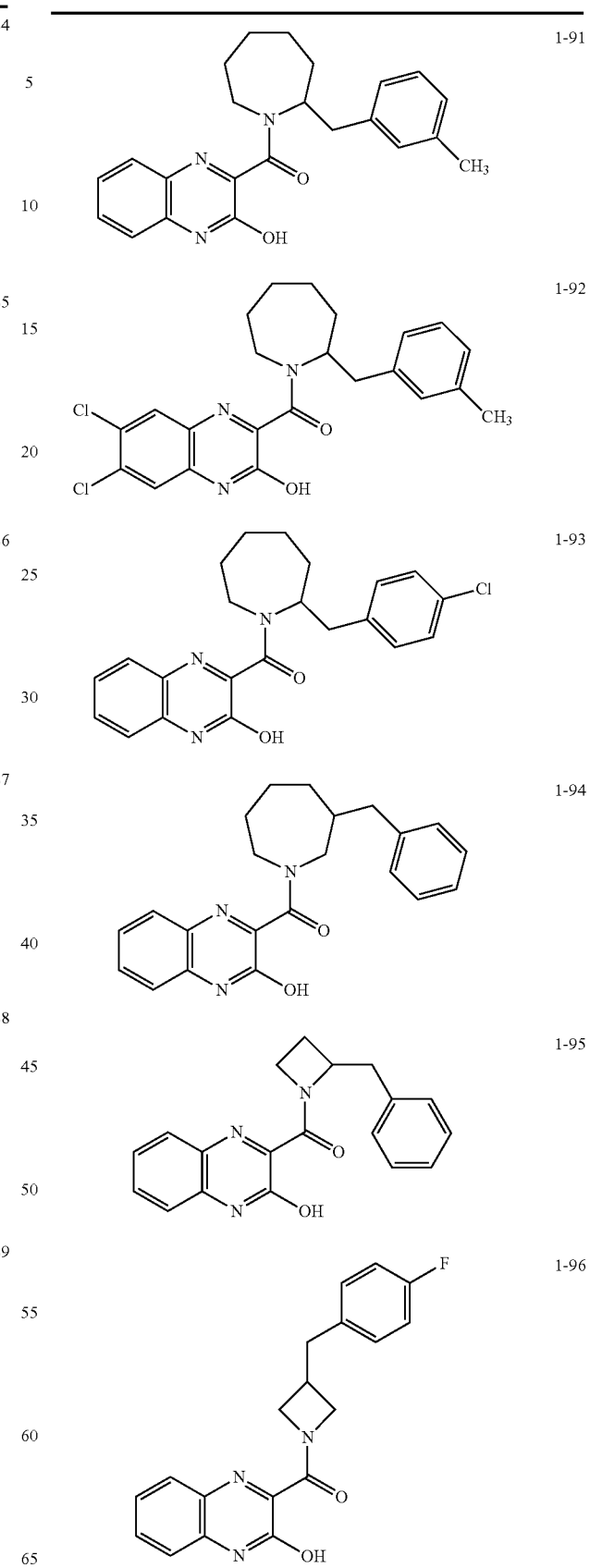

TABLE B
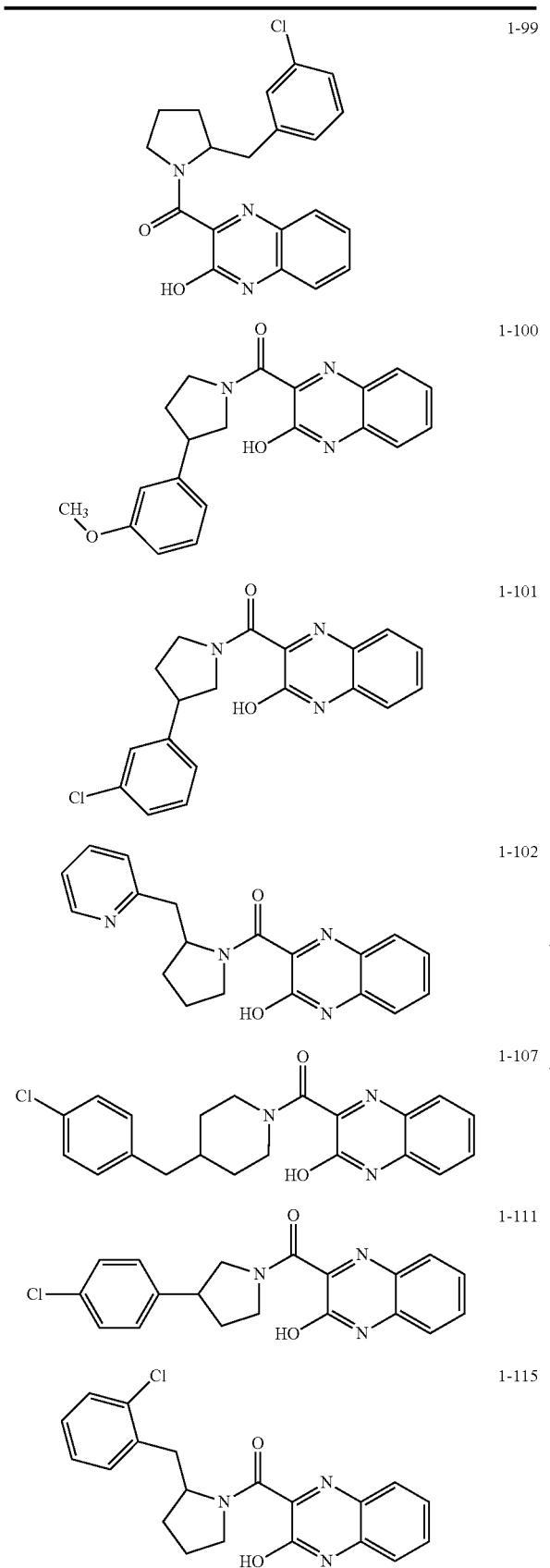
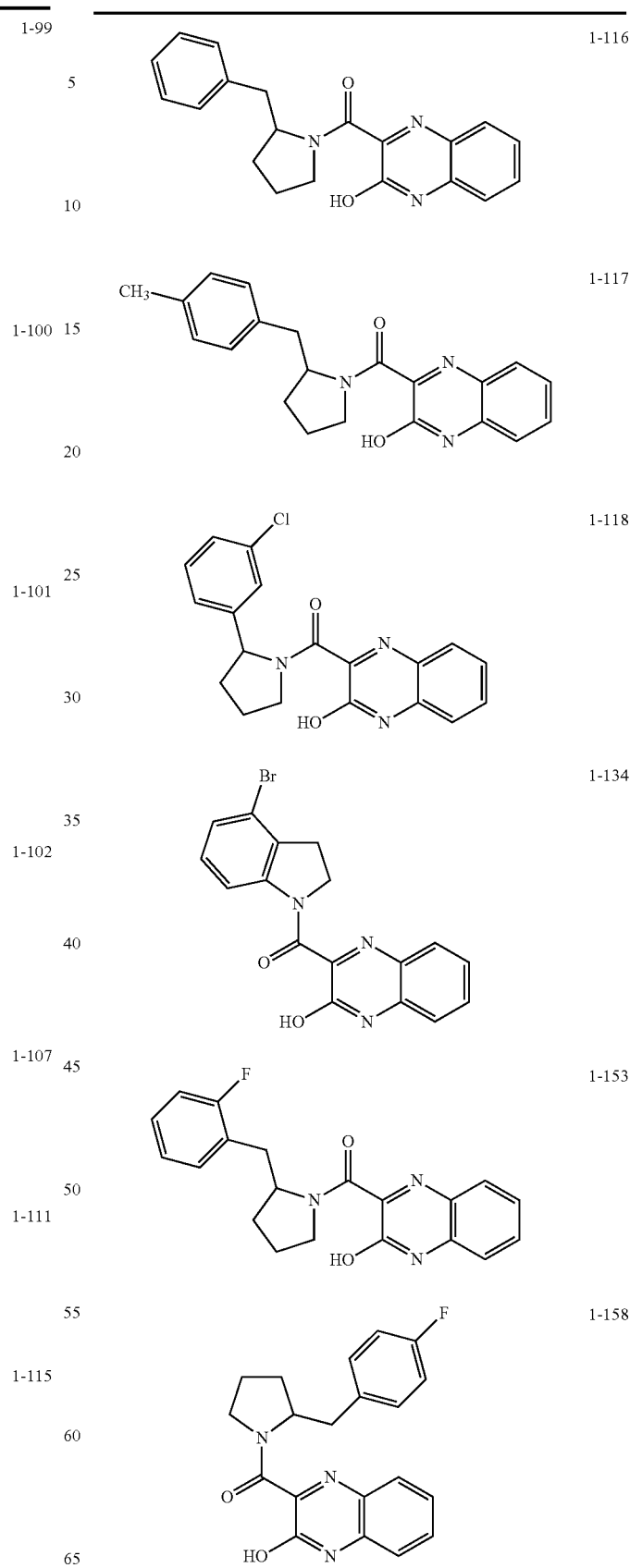

TABLE B-continued
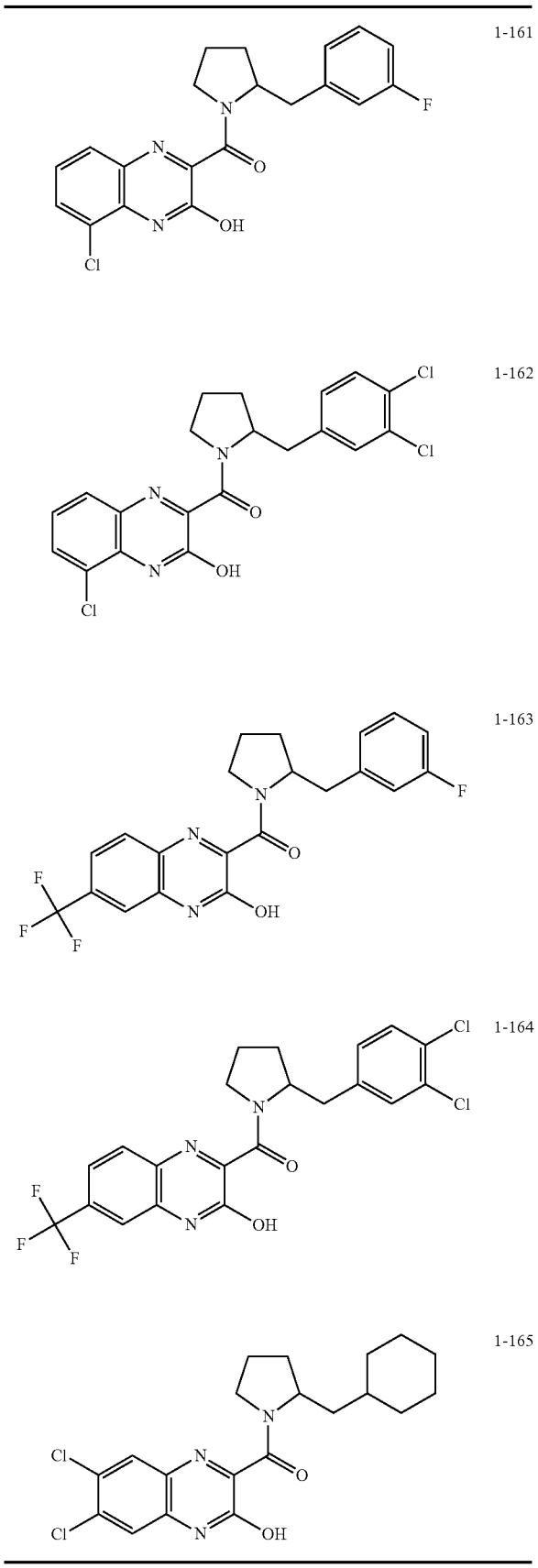
TABLE C
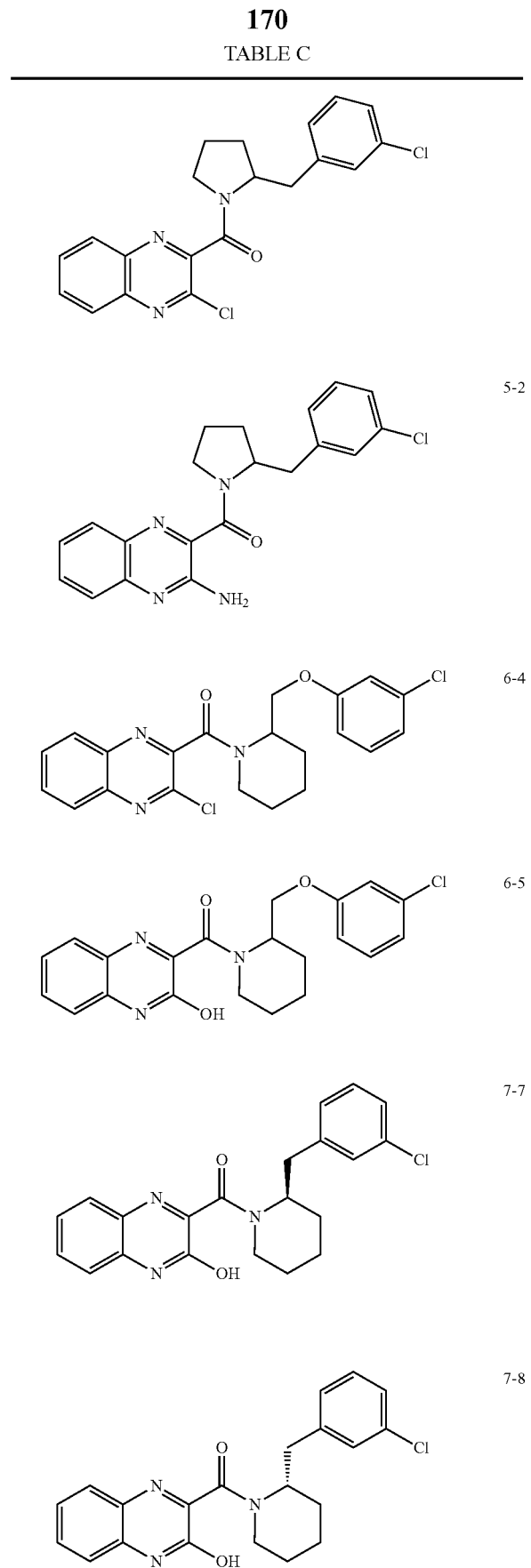

TABLE C-continued
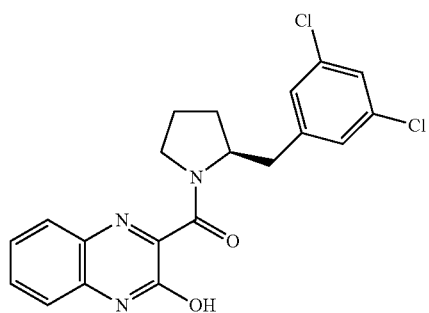 [SMILES: O=C(c1nc2ccccc2nc1O)N1CCC[C@H]1Cc1cc(Cl)cc(Cl)c1]
8-6
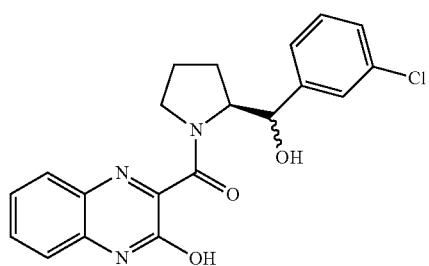 [SMILES: O=C(c1nc2ccccc2nc1O)N1CCC[C@H]1C(O)c1cccc(Cl)c1]
8-7
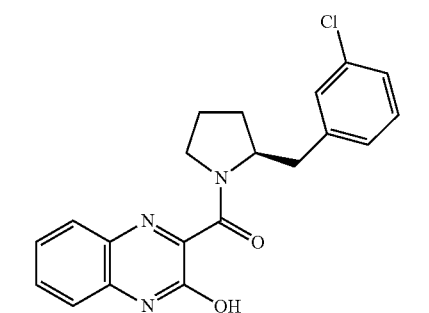 [SMILES: O=C(c1nc2ccccc2nc1O)N1CCC[C@H]1Cc1cccc(Cl)c1]
8-8
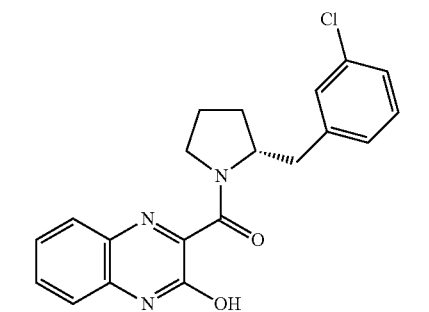 [SMILES: O=C(c1nc2ccccc2nc1O)N1CCC[C@@H]1Cc1cccc(Cl)c1]
8-9
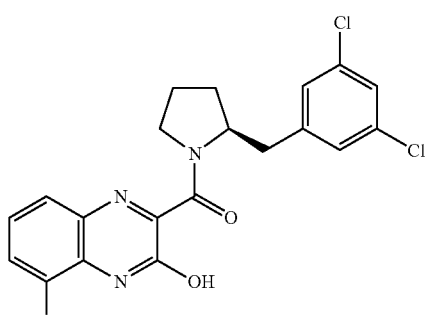
8-10
TABLE C-continued
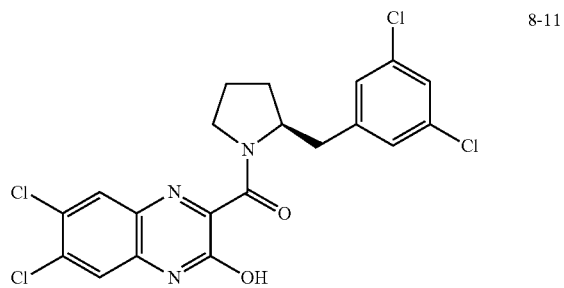
8-11
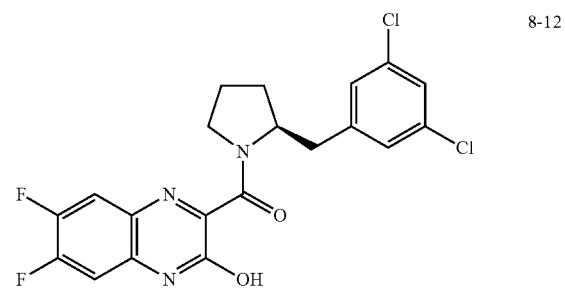
8-12
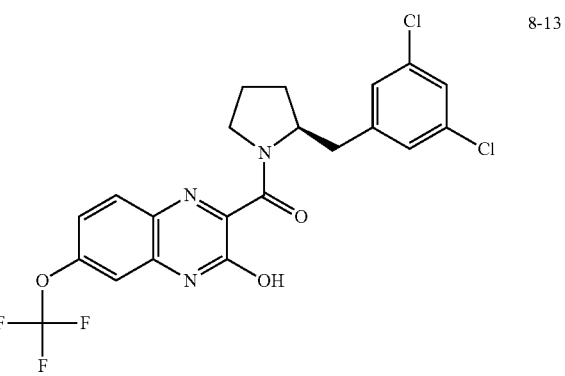
8-13
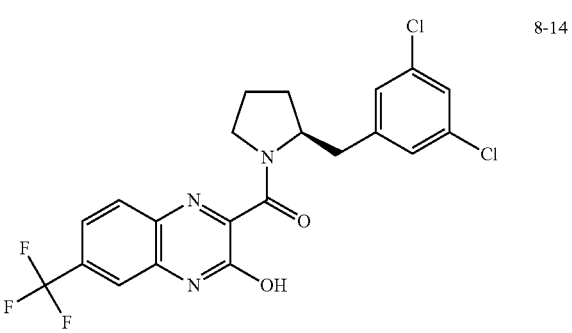
8-14
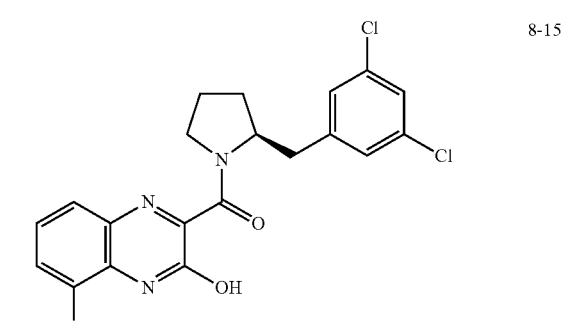
8-15

TABLE C-continued
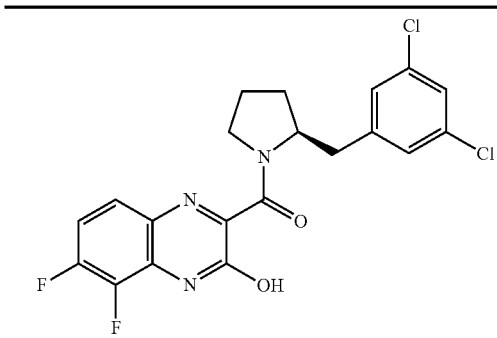
8-17
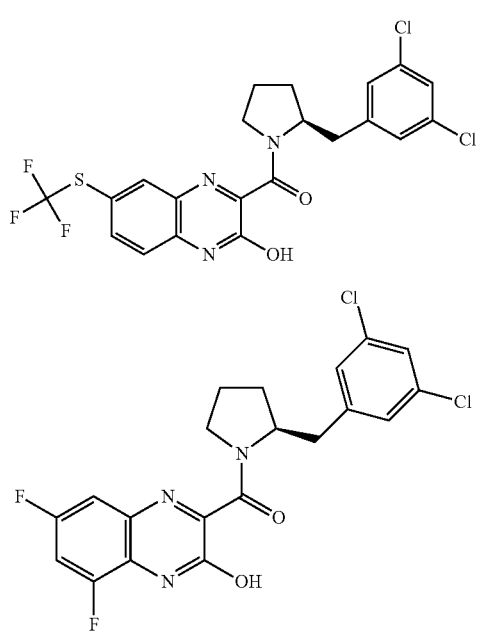
8-18
9-16
TABLE C-continued
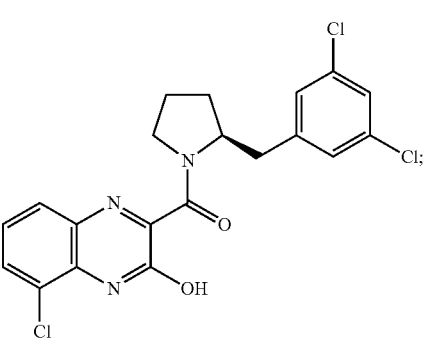
9-18
or a pharmaceutically acceptable salt thereof.
8. The compound of claim 1 which is:
8-10
or a pharmaceutically acceptable salt thereof.
9. A pharmaceutical composition comprising the compound of claim 1, or a pharmaceutically acceptable salt thereof, in combination with a pharmaceutically acceptable carrier.
* * * * *